United States Patent
Suzuki et al.

(10) Patent No.: US 9,388,123 B2
(45) Date of Patent: Jul. 12, 2016

(54) LSD1-SELECTIVE INHIBITOR HAVING LYSINE STRUCTURE

(71) Applicant: KYOTO UNIVERSITY, Kyoto-shi, Kyoto (JP)

(72) Inventors: Takayoshi Suzuki, Kyoto (JP); Yukihiro Itoh, Kyoto (JP); Daisuke Ogasawara, Kyoto (JP); Naoki Miyata, Nagoya (JP); Tamio Mizukami, Nagahama (JP); Ryuzo Sasaki, Nagahama (JP); Akifumi Takaori, Kyoto (JP); Masahiro Kawahara, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/648,109

(22) PCT Filed: Nov. 28, 2013

(86) PCT No.: PCT/JP2013/082011
§ 371 (c)(1),
(2) Date: Aug. 31, 2015

(87) PCT Pub. No.: WO2014/084298
PCT Pub. Date: Jun. 5, 2014

(65) Prior Publication Data
US 2016/0039748 A1   Feb. 11, 2016

(30) Foreign Application Priority Data
Nov. 28, 2012 (JP) ................... 2012-260222

(51) Int. Cl.
| | | |
|---|---|---|
| *C07C 237/06* | (2006.01) | |
| *C07C 271/20* | (2006.01) | |
| *C07D 295/192* | (2006.01) | |
| *A61K 31/165* | (2006.01) | |
| *A61K 31/166* | (2006.01) | |
| *A61K 31/27* | (2006.01) | |
| *A61K 31/495* | (2006.01) | |

(52) U.S. Cl.
CPC ............ *C07C 237/06* (2013.01); *A61K 31/165* (2013.01); *A61K 31/166* (2013.01); *A61K 31/27* (2013.01); *A61K 31/495* (2013.01); *C07C 271/20* (2013.01); *C07D 295/192* (2013.01); *C07C 2101/02* (2013.01)

(58) Field of Classification Search
CPC   C07C 237/06; C07C 271/20; C07C 2101/02; C07D 295/192; A61K 31/27; A61K 31/165; A61K 31/166; A61K 31/495
See application file for complete search history.

(56) References Cited

U.S. PATENT DOCUMENTS

2011/0263604 A1* 10/2011 Guibourt ............... C07C 229/14
                                                              514/237.5

FOREIGN PATENT DOCUMENTS

WO    WO 2010/043721 A1    4/2010
WO    WO 2010/143582 A1    12/2010

OTHER PUBLICATIONS

Metzger et al., *Nature*, 437(7057): 436-439 (Sep. 2005).
Ogasawara et al., *Angewandte Chem. Int. Ed.*, 52(33): 8620-8624 (2013).
Schmidt et al., *Biochemistry*, 46: 4408-4416 (2007).
Ueda et al., *Journal of the American Chemical Society*, 131(48): 17536-17537 (2009).
Japanese Patent Office, International Search Report in International Patent Application No. PCT/JP2013/082011 (Feb. 10, 2014).

* cited by examiner

*Primary Examiner* — Shailendra Kumar
(74) *Attorney, Agent, or Firm* — Leydig, Voit & Mayer, Ltd.

(57) ABSTRACT

Provided is a compound represented by the following formula (I) or a pharmaceutically acceptable salt thereof:

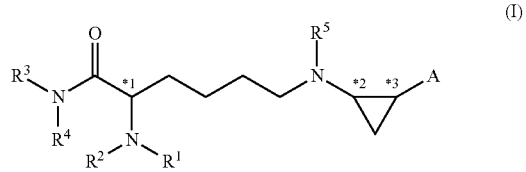

[in the formula, $R^1$ to $R^5$, A, and *1 to *3 are as defined in Description].

9 Claims, 1 Drawing Sheet

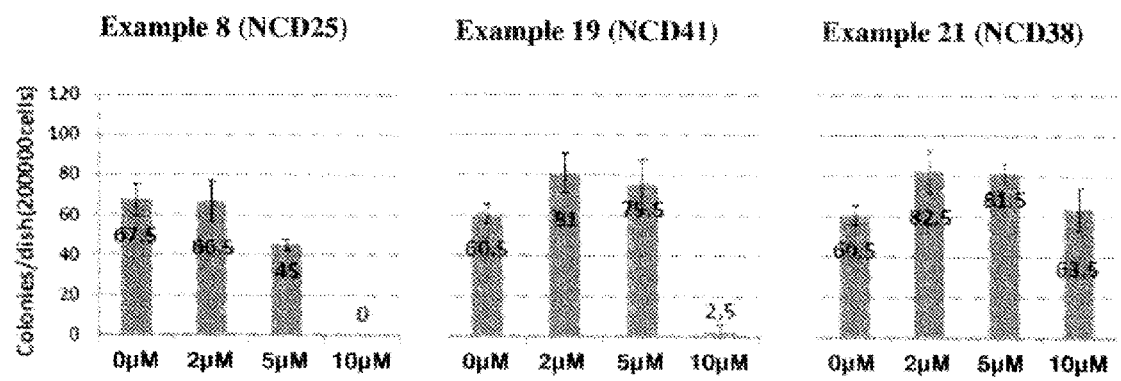

LSD1-SELECTIVE INHIBITOR HAVING LYSINE STRUCTURE

CROSS-REFERENCE TO RELATED APPLICATION

The present application is the U.S. national phase of International Patent Application No. PCT/JP2013/082011, filed Nov. 28, 2013, which claims priority based on Japanese Patent Application No. 2012-260222, filed on Nov. 28, 2012, the disclosure of which is incorporated herein by reference in its entirety.

The present application claims priority based on Japanese Patent Application No. 2012-260222, filed on Nov. 28, 2012, the disclosure of which is incorporated herein by reference in its entirety.

TECHNICAL FIELD

The present invention primarily relates to a compound or a salt thereof having lysine-specific histone demethylase 1 (LSD1)-selective inhibitory activity. The present invention also relates to a pharmaceutical composition including as an active ingredient the compound or the like.

BACKGROUND ART

In recent years, it has been revealed that modification such as methylation or acetylation of a specific amino acid residue in a core histone protein causes a change in chromosomal chromatin structure, which plays an important role in gene regulation. Lysine-specific histone demethylase 1 (LSD1) is a histone demethylase that catalyses demethylation reactions of monomethylated lysine 4 (H3K4me1) and dimethylated lysine 4 (H3K4me2) of a core histone protein histone H3 (Non Patent Literature 1).

It has been reported that cell growth of cancer cells is suppressed by suppressing a function of LSD1 with RNAi. It has also been reported that use of trans-2-phenylcyclopropylamine to be described later as an LSD1 inhibitor is effective for treatment of leukemia.

trans-2-Phenylcyclopropylamine (tranylcypromine) and nialamide are known as compounds capable of inhibiting a function of LSD1 (Non Patent Literatures 1 and 2). However, each of those compounds is a compound that has low inhibitory activity against LSD1 and also inhibits monoamine oxidases (MAOs), which have high homology to LSD1, and hence is not an LSD1-selective inhibitor. MAOs (MAO-A and MAO-B in humans) are important in adjustment of a neurotransmitter, and hence it is difficult to clinically apply tranylcypromine or nialamide as the LSD1 inhibitor because of a high risk of side effects.

In Patent Literature 1 and Non Patent Literature 3, there is a disclosure of a phenylcyclopropylamine derivative capable of selectively inhibiting a function of LSD1. However, the compound has high selectivity for LSD1 but is insufficient in LSD1 inhibitory activity and in suppressing activity against cell growth of cancer cells, in particular, activity against human cancer cells.

CITATION LIST

Patent Literature

[PTL 1] WO 2010/143582 A1

Non Patent Literature

[NPL 1] Biochemistry 2007, 46, pp 4408-4416
[NPL 2] Nature 2005, 437, pp 436-439
[NPL 3] J. Am. Chem. Soc, 2009, 131, pp 17536-17537

SUMMARY OF INVENTION

Technical Problem

A primary object of the present invention is to provide a novel compound having LSD1-selective inhibitory activity and having an antitumor/anticancer action, an antiviral action, and the like.

Solution to Problem

The inventors of the present invention have made extensive investigations, and as a result, have found that a novel compound represented by the general formula (I) has LSD1-selective inhibitory activity and can suppress the cell growth of various cancer cells. The inventors of the present invention have made further investigations and thus completed the present invention.

The present invention encompasses the following embodiments.

Item 1. A compound represented by the following formula (I) or a pharmaceutically acceptable salt thereof.

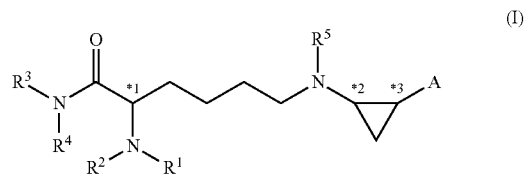

[In the formula:

$R^1$ and $R^2$ are identical to or different from each other, and each represent a hydrogen atom, an alkyl group that may have a substituent, a cycloalkyl group that may have a substituent, an alkylcarbonyl group that may have a substituent, a cycloalkylcarbonyl group that may have a substituent, an arylcarbonyl group that may have a substituent, a heteroarylcarbonyl group that may have a substituent, an alkyloxycarbonyl group that may have a substituent, a cycloalkyloxycarbonyl group that may have a substituent, an aryloxycarbonyl group that may have a substituent, or a heteroaryloxycarbonyl group that may have a substituent;

$R^3$ and $R^4$ are identical to or different from each other, and each represent a hydrogen atom, an alkyl group that may have a substituent, a cycloalkyl group that may have a substituent, an aryl group that may have a substituent, a heteroaryl group that may have a substituent, or an aralkyl group that may have a substituent, or $R^3$ and $R^4$ may form a nitrogen-containing heterocycle together with a nitrogen atom to which $R^3$ and $R^4$ are bonded, provided that $R^3$ and $R^4$ do not simultaneously represent a hydrogen atom;

$R^5$ represents a hydrogen atom, an alkyl group that may have a substituent, a cycloalkyl group that may have a substituent, an aryl group that may have a substituent, a heteroaryl group that may have a substituent, or an aralkyl group that may have a substituent;

A represents an aryl group that may have a substituent or a heteroaryl group that may have a substituent; and

*1 to *3 each represent asymmetric carbon.]

Item 2. A compound represented by the following formula (II) or a pharmaceutically acceptable salt thereof.

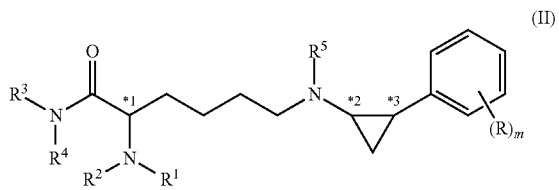

(II)

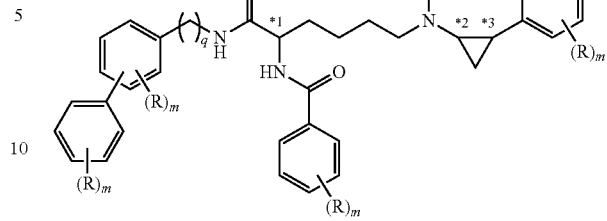

(IV)

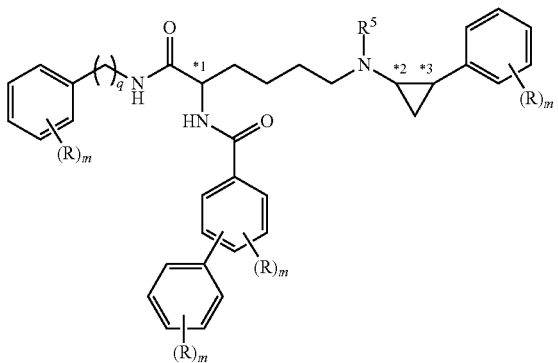

(V)

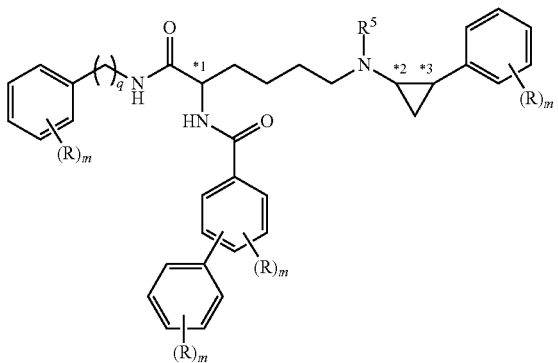

(VI)

[In the formula:

R¹ and R² are identical to or different from each other, and each represent a hydrogen atom, an alkyl group that may have a substituent, a cycloalkyl group that may have a substituent, an alkylcarbonyl group that may have a substituent, a cycloalkylcarbonyl group that may have a substituent, an arylcarbonyl group that may have a substituent, a heteroarylcarbonyl group that may have a substituent, an aralkylcarbonyl group that may have a substituent, an alkyloxycarbonyl group that may have a substituent, a cycloalkyloxycarbonyl group that may have a substituent, an aryloxycarbonyl group that may have a substituent, or a heteroaryloxycarbonyl group that may have a substituent;

R³ and R⁴ are identical to or different from each other, and each represent a hydrogen atom, an alkyl group that may have a substituent, a cycloalkyl group that may have a substituent, an aryl group that may have a substituent, a heteroaryl group that may have a substituent, or an aralkyl group that may have a substituent, or R³ and R⁴ may form a nitrogen-containing heterocycle together with a nitrogen atom to which R³ and R⁴ are bonded, provided that R³ and R⁴ do not simultaneously represent a hydrogen atom;

R⁵ represents a hydrogen atom, an alkyl group that may have a substituent, a cycloalkyl group that may have a substituent, an aryl group that may have a substituent, a heteroaryl group that may have a substituent, or an aralkyl group that may have a substituent;

R represents a hydrogen atom or a substituent;

m represents an integer of from 0 to 5; and

*1 to *3 each represent asymmetric carbon.]

Item 3. A compound represented by any one of the following formulae (III) to (VI) or a pharmaceutically acceptable salt thereof.

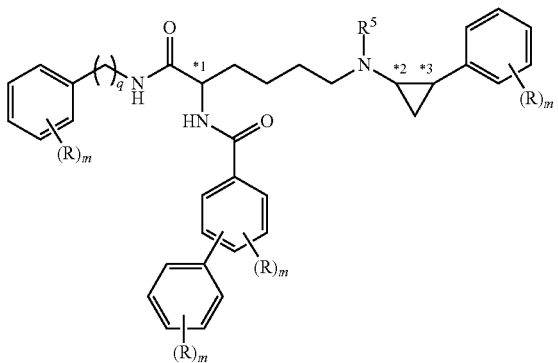

(III)

[In the formulae:

R⁵ represents a hydrogen atom, an alkyl group that may have a substituent, a cycloalkyl group that may have a substituent, an aryl group that may have a substituent, a heteroaryl group that may have a substituent, or an aralkyl group that may have a substituent;

R's each represent a hydrogen atom or a substituent;

m's are identical to or different from each other, and each represent an integer of from 0 to 5;

q represents an integer of from 0 to 5;

R's are identical to or different from each other, and each represent a hydrogen atom or a substituent; and

*1 to *3 each represent asymmetric carbon.]

Item 4. Any one of the following compounds or a pharmaceutically acceptable salt thereof:

2-(N-benzenecarbonyl)amino-6-(trans-2-phenylcyclopropan-1-amino)-N-benzylhexanamide;

2-(N-tert-butoxycarbonyl)amino-6-(trans-2-phenylcyclopropan-1-amino)-N-benzylhexanamide;

2-amino-6-(trans-2-phenylcyclopropan-1-amino)-N-benzylhexanamide;

2-[N-(4-methylbenzenecarbonyl)]amino-6-(trans-2-phenylcyclopropan-1-amino)-N-benzylhexanamide;

2-[N-(4-tert-butylbenzenecarbonyl)]amino-6-(trans-phenyl-cyclopropan-1-amino)-N-benzylhexanamide;

2-[N-(4-chlorobenzenecarbonyl)]amino-6-(trans-2-phenyl-cyclopropan-1-amino)-N-benzylhexanamide;

2-[N-(4-fluorobenzenecarbonyl)]amino-6-(trans-2-phenyl-cyclopropan-1-amino)-N-benzylhexanamide;

2-[N-(4-phenylbenzenecarbonyl)]amino-6-(trans-2-phenyl-cyclopropan-1-amino)-N-benzylhexanamide;

2-[N-(4-trifluoromethylbenzenecarbonyl)]amino-6-(trans-2-phenylcyclopropan-1-amino)-N-benzylhexanamide;

2-{3-[(2-amino)ethylcarbamoyl]benzenecarbonylamino}-6-(trans-2-phenylcyclopropan-1-amino)-N-benzylhexanamide;

2-[3-(piperazine-1-carbonyl)benzenecarbonylamino]-6-(trans-2-phenylcyclopropan-1-amino)-N-benzylhexanamide;

2-[N-(4-phenylbenzenecarbonyl)]amino-6-(trans-2-phenyl-cyclopropan-1-amino)-N-(4-methylbenzyl)hexanamide;

2-[N-(4-phenylbenzenecarbonyl)]amino-6-(trans-2-phenyl-cyclopropan-1-amino)-N-(4-fluorobenzyl)hexanamide;

2-[N-(4-phenylbenzenecarbonyl)]amino-6-(trans-2-phenyl-cyclopropan-1-amino)-N-(4-phenylbenzyl)hexanamide;

2-[N-(4-phenylbenzenecarbonyl)]amino-6-(trans-2-phenyl-cyclopropan-1-amino)-N-(4-tert-butylbenzyl)hexanamide;

2-[N-(4-phenylbenzenecarbonyl)]amino-6-(trans-2-phenyl-cyclopropan-1-amino)-N-(3-methylbenzyl)hexanamide;

2-[N-(4-phenylbenzenecarbonyl)]amino-6-(trans-2-phenyl-cyclopropan-1-amino)-N-(3-fluorobenzyl)hexanamide;

2-[N-(4-phenylbenzenecarbonyl)]amino-6-(trans-2-phenyl-cyclopropan-1-amino)-N-(3-phenylbenzyl)hexanamide;

2-[N-(4-phenylbenzenecarbonyl)]amino-6-(trans-2-phenyl-cyclopropan-1-amino)-N-(3-trifluoromethylbenzyl)hexanamide;

2-[N-(4-phenylbenzenecarbonyl)]amino-6-(trans-2-phenyl-cyclopropan-1-amino)-N-(4-chlorobenzyl)hexanamide; and 2-[N-(4-phenylbenzenecarbonyl)]amino-6-(trans-2-phenyl-cyclopropan-1-amino)-N-(3-chlorobenzyl)hexanamide.

Item 5. A pharmaceutical composition, including the compound or the pharmaceutically acceptable salt thereof of any one of Items 1 to 4.

Item 6. An anticancer agent, including as an active ingredient the compound or the pharmaceutically acceptable salt thereof of any one of Items 1 to 4.

Item 7. An antiviral drug, including as an active ingredient the compound or the pharmaceutically acceptable salt thereof of any one of Items 1 to 4.

Item 8. A therapeutic drug for hemoglobinopathy, including as an active ingredient the compound or the pharmaceutically acceptable salt thereof of any one of Items 1 to 4.

Item 9. A lysine-specific demethylase 1 (LSD1) inhibitor, including as an active ingredient the compound or the pharmaceutically acceptable salt thereof of any one of Items 1 to 4.

Advantageous Effects of Invention

According to each of the embodiments of the present invention, the compound having LSD1-selective inhibitory activity is provided. Further, the compound of the present invention has a high antitumor/anticancer action, antiviral action, and the like, and hence may be suitably used as an antitumor agent/anticancer agent, an antiviral drug, or the like.

BRIEF DESCRIPTION OF DRAWINGS

FIG. 1 is a graph for showing evaluation results of compounds of Example 8 (NCD25), Example 19 (NCD41), and Example 21 (NCD38) for their growth suppressing effects on human normal cells.

DESCRIPTION OF EMBODIMENTS

1. Compound

A compound of the present invention is a compound represented by the following general formula (I) or a pharmacologically acceptable salt thereof.

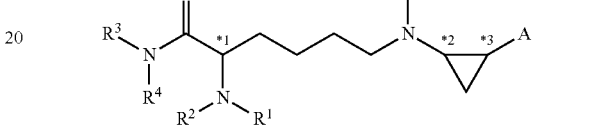

[In the formula: $R^1$ and $R^2$ are identical to or different from each other, and each represent a hydrogen atom, an alkyl group that may have a substituent, a cycloalkyl group that may have a substituent, an alkylcarbonyl group that may have a substituent, a cycloalkylcarbonyl group that may have a substituent, an arylcarbonyl group that may have a substituent, a heteroarylcarbonyl group that may have a substituent, an aralkylcarbonyl group that may have a substituent, an alkyloxycarbonyl group that may have a substituent, a cycloalkyloxycarbonyl group that may have a substituent, an aryloxycarbonyl group that may have a substituent, or a heteroaryloxycarbonyl group that may have a substituent; $R^3$ and $R^4$ are identical to or different from each other, and each represent a hydrogen atom, an alkyl group that may have a substituent, a cycloalkyl group that may have a substituent, an aryl group that may have a substituent, a heteroaryl group that may have a substituent, or an aralkyl group that may have a substituent, or $R^3$ and $R^4$ may form a nitrogen-containing heterocycle together with a nitrogen atom to which $R^3$ and $R^4$ are bonded, provided that $R^3$ and $R^4$ do not simultaneously represent a hydrogen atom; $R^5$ represents a hydrogen atom, an alkyl group that may have a substituent, a cycloalkyl group that may have a substituent, an aryl group that may have a substituent, a heteroaryl group that may have a substituent, or an aralkyl group that may have a substituent; A represents an aryl group that may have a substituent or a heteroaryl group that may have a substituent; and *1 to *3 each represent asymmetric carbon.]

The compound represented by the formula (I) has a lysine structure, and hence may also be called a lysine derivative.

Examples of the "alkyl group" include linear or branched alkyl groups including alkyl groups each having 1 to 6 carbon atoms, such as methyl, ethyl, n-propyl, isopropyl, n-butyl, isobutyl, tert-butyl, n-pentyl, isopentyl, and n-hexyl.

Examples of the "cycloalkyl group" include cycloalkyl groups each having 3 to 7 carbon atoms, such as cyclopropyl, cyclobutyl, cyclopentyl, cyclohexyl, and cycloheptyl.

The "aryl group" means a monocyclic or polycyclic group formed mainly of a six-membered aromatic hydrocarbon ring. Specific examples thereof include phenyl, naphthyl, fluorenyl, anthryl, biphenylyl, tetrahydronaphthyl, and phenanthryl.

The "heteroaryl group" means a monocyclic or polycyclic group formed of a five- or six-membered aromatic ring including 1 to 3 heteroatoms selected from a nitrogen atom, an oxygen atom, and a sulfur atom, and in the case of the polycyclic group, it is only necessary that at least one ring be an aromatic ring. Specific examples thereof include furyl, thienyl, pyrrolyl, imidazolyl, pyrazolyl, oxazolyl, thiazolyl, isoxazolyl, isothiazolyl, pyridyl, pyrazinyl, pyrimidinyl, pyridazinyl, indolyl, quinolyl, isoquinolyl, benzo[b]thienyl, benzimidazolyl, benzothiazolyl, and benzoxazolyl.

Examples of the "aralkyl group" include alkyl groups each having 1 to 6 carbon atoms substituted with about 1 to 3 aryl groups. Specific examples thereof include benzyl, phenethyl, naphthylmethyl, and phenylbenzyl (—CH$_2$-Ph-Ph, where Ph represents phenyl and the position of Ph may be any of ortho, meta, and para positions).

Examples of the "nitrogen-containing heterocycle" include nitrogen-containing heterocycles each having a five- or six-membered ring, such as pyrrolidino, piperidino, piperazinyl, morpholino, and thiomorpholino.

An example of the "alkylcarbonyl group" is an alkylcarbonyl group whose alkyl moiety is the above-mentioned alkyl group. Specific examples thereof include alkylcarbonyls whose alkyl moiety has 1 to 6 carbon atoms, such as methylcarbonyl (acetyl), ethylcarbonyl (propionyl), n-propylcarbonyl (butyryl), isopropylcarbonyl (isobutyryl), n-butylcarbonyl (valeryl), isobutylcarbonyl (isovaleryl), tert-butylcarbonyl, n-pentylcarbonyl, isopentylcarbonyl, and n-hexylcarbonyl.

An example of the "cycloalkylcarbonyl group" is a cycloalkylcarbonyl group whose cycloalkyl moiety is the above-mentioned cycloalkyl group. Specific examples thereof include cycloalkylcarbonyl groups whose cycloalkyl moiety has 3 to 7 carbon atoms, such as cyclopropylcarbonyl, cyclobutylcarbonyl, cyclopentylcarbonyl, cyclohexylcarbonyl, and cycloheptylcarbonyl.

An example of the "arylcarbonyl group" is an arylcarbonyl group whose aryl moiety is the above-mentioned aryl group. Specific examples thereof include phenylcarbonyl, naphthylcarbonyl, fluorenylcarbonyl, anthrylcarbonyl, biphenylylcarbonyl, tetrahydronaphthylcarbonyl, and phenanthrylcarbonyl.

An example of the "heteroarylcarbonyl group" is an arylcarbonyl group whose heteroaryl moiety is the above-mentioned heteroaryl group. Specific examples thereof include furylcarbonyl, thienylcarbonyl, imidazolylcarbonyl, thiazolylcarbonyl, pyridylcarbonyl, and quinolylcarbonyl.

An example of the "aralkylcarbonyl group" is an aralkylcarbonyl group whose aralkyl moiety is the above-mentioned aralkyl group. Specific examples thereof include aralkylcarbonyl groups whose alkyl moiety has 1 to 6 carbon atoms, substituted with about 1 to 3 aryl groups, such as benzylcarbonyl, phenethylcarbonyl, and naphthylmethylcarbonyl.

An example of the "alkyloxycarbonyl group" (sometimes referred to as "alkoxycarbonyl group") is an alkyloxycarbonyl group whose alkyl moiety is the above-mentioned alkyl group. Specific examples thereof include alkyloxycarbonyl groups whose alkyl moiety has 1 to 6 carbon atoms, such as methyloxycarbonyl (methoxycarbonyl), ethyloxycarbonyl (ethoxycarbonyl), n-propyloxycarbonyl (n-propoxycarbonyl), isopropyloxycarbonyl (isopropoxycarbonyl), n-butyloxycarbonyl (n-butoxycarbonyl), isobutyloxycarbonyl (isobutoxycarbonyl), tert-butyloxycarbonyl (tert-butoxycarbonyl), n-pentyloxycarbonyl, isopentyloxycarbonyl, and n-hexyloxycarbonyl.

An example of the "cycloalkyloxycarbonyl group" (sometimes referred to as "cycloalkoxycarbonyl group") is a cycloalkyloxycarbonyl group whose cycloalkyl moiety is the above-mentioned cycloalkyl group. Specific examples thereof include cycloalkyloxycarbonyl groups whose cycloalkyl moiety has 3 to 7 carbon atoms, such as cyclopropyloxycarbonyl (cyclopropoxycarbonyl), cyclobutyloxycarbonyl (cyclobutoxycarbonyl), cyclopentyloxycarbonyl, cyclohexyloxycarbonyl, and cycloheptyloxycarbonyl.

An example of the "aryloxycarbonyl group" is an aryloxycarbonyl group whose aryl moiety is the above-mentioned aryl group. Specific examples thereof include phenyloxycarbonyl, naphthyloxycarbonyl, fluorenyloxycarbonyl, anthryloxycarbonyl, biphenylyloxycarbonyl, tetrahydronaphthyloxycarbonyl, and phenanthryloxycarbonyl.

An example of the "heteroaryloxycarbonyl group" is a heteroaryloxycarbonyl group whose heteroaryl moiety is the above-mentioned heteroaryl group. Specific examples thereof include furyloxycarbonyl, thienyloxycarbonyl, imidazolyloxycarbonyl, thiazolyloxycarbonyl, pyridyloxycarbonyl, and quinolyloxycarbonyl.

The alkyl group, the cycloalkyl group, the aryl group, the heteroaryl group, and the aralkyl group may each have, for example, 1 to 5, preferably 1 to 3, more preferably 1 or 2 substituents.

Herein, the phrase "that may have a substituent" encompasses "substituted" and "unsubstituted".

Herein, examples of the "substituent" include a halogen atom, an alkyl group, an alkoxy group (e.g., methoxy or ethoxy), hydroxy, a perfluoroalkyl group (e.g., trifluoromethyl), a perfluoroalkoxy group (e.g., trifluoromethoxy), cyano, nitro, amino, a mono- or dialkylamino group, an alkoxycarbonylamino group, and an acyl group (e.g., formyl, an alkylcarbonyl group, carbamoyl, a mono- or dialkylcarbamoyl group, an aminoalkylcarbamoyl group, or a nitrogen-containing heterocycle-carbonyl group).

Herein, the "halogen" refers to fluorine, chlorine, bromine, or iodine. The "halogen" is preferably fluorine, chlorine, or bromine.

The "acyl group" means a group represented by —COR$^x$.

Examples of the "mono- or dialkylamino group" include mono- or dialkylamino groups each having 1 to 6 carbon atoms, such as methylamino, ethylamino, propylamino, isopropylamino, dimethylamino, diethylamino, dipropylamino, diisopropylamino, and methylethylamino.

Examples of the "aminoalkylcarbamoyl group" (—CONH-(alkyl)-NH$_2$) include aminoalkylamino groups each having 1 to 6 carbon atoms, such as aminomethylcarbamoyl, aminoethylcarbamoyl, and aminopropylcarbamoyl.

Examples of the "nitrogen-containing heterocycle-carbonyl group" include groups each having a nitrogen-containing heterocycle bonded to a carbonyl group through a nitrogen atom, such as a 1-piperidinocarbonyl group, a 1-piperazinylcarbonyl group, and a 4-morpholinocarbonyl group.

Examples of the "alkoxycarbonylamino group" include alkoxycarbonylamino groups each having 1 to 6 carbon atoms, such as methoxycarbonylamino, ethoxycarbonylamino, propoxycarbonylamino, isopropoxycarbonylamino, butoxycarbonylamino, isobutoxycarbonylamino, and tert-butoxycarbonylamino.

Examples of the "mono- or dialkylcarbamoyl group" include mono- or dialkylcarbamoyl groups each having 1 to 6 carbon atoms, such as methylcarbamoyl, ethylcarbamoyl, propylcarbamoyl, isopropylcarbamoyl, dimethylcarbamoyl, diethylcarbamoyl, dipropylcarbamoyl, diisopropylcarbamoyl, and methylethylcarbamoyl.

It is preferred that $R^1$ and $R^2$ both represent a hydrogen atom, or that one of $R^1$ and $R^2$ represent a hydrogen atom and the other represent an alkyloxycarbonyl group that may have a substituent, an arylcarbonyl group that may have a substituent, or an aralkylcarbonyl group that may have a substituent. It is more preferred that one of $R^1$ and $R^2$ represent a hydrogen atom and the other represent an arylcarbonyl group that may have a substituent. The arylcarbonyl group that may have a substituent is particularly preferably a phenylcarbonyl group that may have a substituent or a biphenylcarbonyl group that may have a substituent.

The following formulae are given as preferred modes of the phenylcarbonyl group that may have a substituent and the biphenylcarbonyl group that may have a substituent.

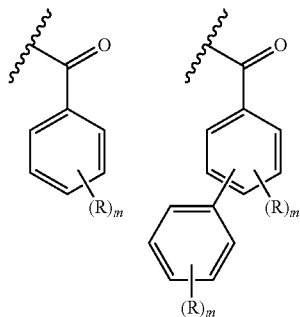

[In the formulae: R's each represent a hydrogen atom or a substituent; and m's each represent an integer of from 0 to 5.]

m represents the number of substituents. m represents preferably an integer of from 0 to 3, more preferably 0 or 1. The substituent is preferably a halogen atom or an alkyl group, more preferably a fluorine atom, a chlorine atom, methyl, or tert-butyl. The position of the substituent is not particularly limited. In the case of m=1, the position of the substituent may be any of ortho, meta, and para positions.

The following formula is given as a particularly preferred mode of the biphenylcarbonyl group that may have a substituent.

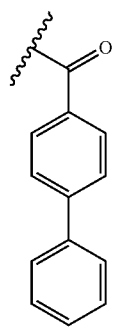

It is preferred that one of $R^3$ and $R^4$ represent a hydrogen atom and the other represent an aryl group that may have a substituent or an aralkyl group that may have a substituent. The other of $R^3$ and $R^4$ not representing the hydrogen atom represents more preferably an aralkyl group that may have a substituent, particularly preferably a benzyl group that may have a substituent or a phenylbenzyl group that may have a substituent.

The following formulae are given as preferred modes of the benzyl group that may have a substituent and the phenylbenzyl group that may have a substituent.

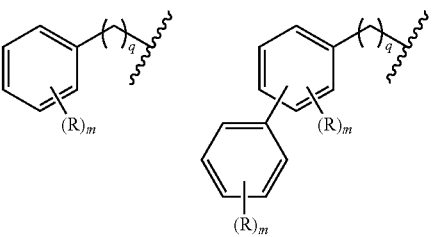

[In the formulae: m's are identical to or different from each other, and each represent an integer of from 0 to 5; R's are identical to or different from each other, and each represent a hydrogen atom or a substituent; and q represents an integer of from 0 to 5.]

The following formula is given as a particularly preferred mode of the benzyl group that may have a substituent.

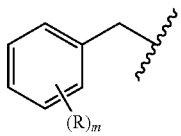

[In the formula, R and m are the same as those described above.]

m represents the number of substituents. m represents preferably an integer of from 0 to 3, more preferably 0 or 1. The substituent is preferably a halogen atom, an alkyl group, or a perfluoroalkyl group, more preferably a fluorine atom, a chlorine atom, methyl, tert-butyl, or trifluoromethyl. The position of the substituent is not particularly limited. In the case of m=1, the position of the substituent may be any of ortho, meta, and para positions.

q represents preferably an integer of from 0 to 3, more preferably 0 or 1, particularly preferably 1.

$R^5$ represents preferably a hydrogen atom or an alkyl group that may have a substituent, more preferably a hydrogen atom or a methyl group.

A represents preferably an aryl group that may have a substituent, more preferably a phenyl group that may have a substituent. A phenyl group that may have a substituent represented by the following formula is given as a preferred mode of A.

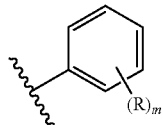

[In the formula: R represents a hydrogen atom or a substituent; and m represents an integer of from 0 to 5.]

m represents the number of substituents. m represents preferably an integer of from 0 to 3, more preferably 0 or 1. The substituent is preferably a halogen atom, an alkyl group, an alkoxy group, a perfluoroalkyl group, or nitro, more preferably a fluorine atom, a chlorine atom, methyl, tert-butyl, methoxy, trifluoromethyl, or nitro. The position of the substituent is not particularly limited. In the case of m=1, the position of the substituent may be any of ortho, meta, and para positions.

The compound of the present invention has asymmetric carbon, and the configuration (R configuration/S configuration or L configuration/D configuration) of each asymmetric carbon may be any of one of the configurations and a mixture (including a racemic mixture) thereof.

In particular, in the general formula (I), *1 to *3 each represent asymmetric carbon. The configuration of C*1 may be any of the following L configuration:

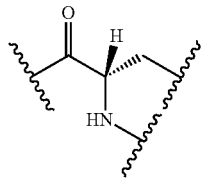

and the following D configuration:

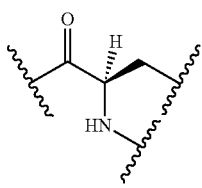 [SMILES: *C[C@@H](N*)C(*)=O]

and the L configuration is preferred.

The relative configuration of a nitrogen atom bonded to C*2 and an A site bonded to C*3 with respect to a cyclopropane ring formed of C*2 and C*3 may be any of the following trans configuration:

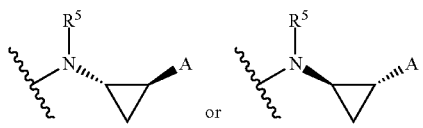

[in the formula, R5 and A are the same as those described above.] and the following cis configuration:

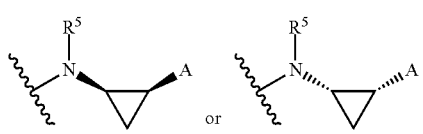

[in the formula, R5 and A are the same as those described above] and the trans configuration is preferred.

A compound represented by the following general formula (II) is given as a preferred mode of the compound of the present invention.

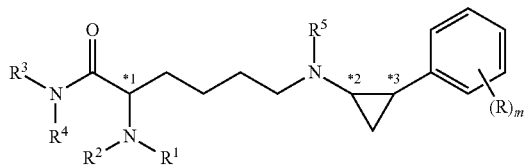

(II)

[In the formula: R1, R2, R3, R4, R5, and *1 to *3 are the same as those described above; R represents a hydrogen atom or a substituent; and m represents an integer of from 0 to 5.]

Compounds represented by the following general formulae (III) to (VI) or pharmaceutically acceptable salts thereof are given as more preferred modes of the compound of the present invention.

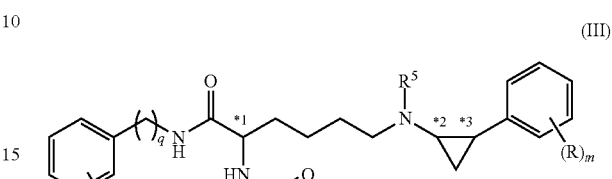

(III)

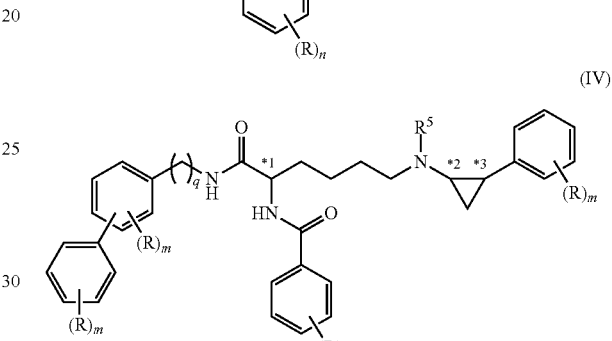

(IV)

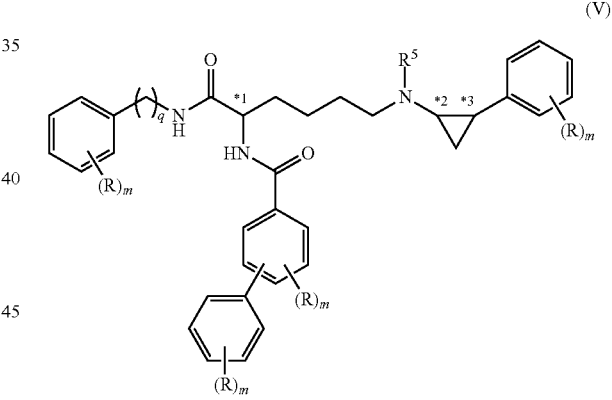

(V)

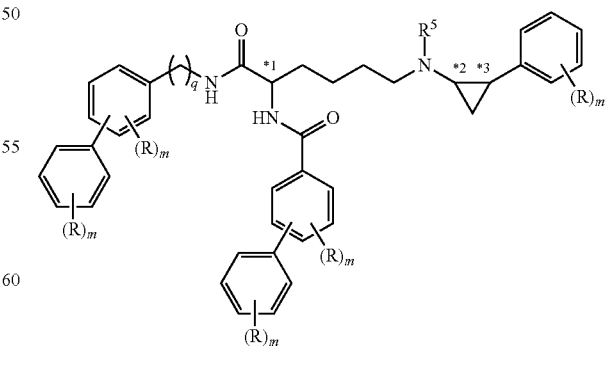

(VI)

[In the formulae: R5 and *1 to *3 are the same as those described above; m's are identical to or different from each other, and each represent an integer of from 0 to 5; R's are identical to or different from each other, and each represent a hydrogen atom or a substituent; and q represents an integer of from 0 to 5.]

In the general formulae (III) to (VI), m represents the number of substituents. m represents preferably an integer of from 0 to 3, more preferably 0 or 1. The substituent is preferably a halogen atom, an alkyl group, or an acyl group, more preferably a fluorine atom, a chlorine atom, methyl, or tert-butyl.

q represents preferably an integer of from 0 to 3, more preferably 0 or 1.

Compounds described in Examples may be given as particularly preferred modes of the compound of the present invention.

The following compounds may be given as other modes of the compound of the present invention: 2-[N-(4-phenylbenzenecarbonyl)]amino-6-(trans-2-p-tolylcyclopropan-1-amino)-N-(3-chlorobenzyl)hexanamide;

2-[N-(4-phenylbenzenecarbonyl)]amino-6-(trans-2-m-tolylcyclopropan-1-amino)-N-(3-chlorobenzyl)hexanamide;

2-[N-(4-phenylbenzenecarbonyl)]amino-6-(trans-2-o-tolylcyclopropan-1-amino)-N-(3-chlorobenzyl)hexanamide;

2-[N-(4-phenylbenzenecarbonyl)]amino-6-(trans-2-p-methoxyphenylcyclopropan-1-amino)-N-(3-chlorobenzyl)hexanamide;

2-[N-(4-phenylbenzenecarbonyl)]amino-6-(trans-2-m-methoxyphenylcyclopropan-1-amino)-N-(3-chlorobenzyl)hexanamide;

2-[N-(4-phenylbenzenecarbonyl)]amino-6-(trans-2-o-methoxyphenylcyclopropan-1-amino)-N-(3-chlorobenzyl)hexanamide;

2-[N-(4-phenylbenzenecarbonyl)]amino-6-(trans-2-p-trifluoromethylphenylcyclopropan-1-amino)-N-(3-chlorobenzyl)hexanamide;

2-[N-(4-phenylbenzenecarbonyl)]amino-6-(trans-2-p trifluoromethylphenylcyclopropan-1-amino)-N-(3-chlorobenzyl)hexanamide;

2-[N-(4-phenylbenzenecarbonyl)]amino-6-(trans-2-o trifluoromethylphenylcyclopropan-1-amino)-N-(3-chlorobenzyl)hexanamide;

2-[N-(4-phenylbenzenecarbonyl)]amino-6-(trans-2-p nitrophenylcyclopropan-1-amino)-N-(3-chlorobenzyl)hexamide;

2-[N-(4-phenylbenzenecarbonyl)]amino-6-(trans-2-m nitrophenylcyclopropan-1-amino)-N-(3-chlorobenzyl)hexanamide;

2-[N-(4-phenylbenzenecarbonyl)]amino-6-(trans-2-o nitrophenylcyclopropan-1-amino)-N-(3-chlorobenzyl)hexanamide;

2-[N-(4-phenylbenzenecarbonyl)]amino-6-(trans-2-p-tert-butylphenylcyclopropan-1-amino)-N-(3-chlorobenzyl)hexanamide;

2-[N-(4-phenylbenzenecarbonyl)]amino-6-(trans-2-m-tert-butylphenylcyclopropan-1-amino)-N-(3-chlorobenzyl)hexanamide;

2-[N-(4-phenylbenzenecarbonyl)]amino-6-(trans-2-o-tert-butylphenylcyclopropan-1-amino)-N-(3-chlorobenzyl)hexamide;

2-[N-(4-phenylbenzenecarbonyl)]amino-6-(trans-2-(naphthalenyl)cyclopropan-1-amino)-N-(3-chlorobenzyl)hexanamide;

2-[N-(4-phenylbenzenecarbonyl)]amino-6-(trans-2-(2-(naphthalenyl)cyclopropan-1-amino)-N-(3-chlorobenzyl)hexanamide;

2-[N-(4-phenylbenzenecarbonyl)]amino-6-(trans-2-(2-quinolinyl)cyclopropan-1-amino)-N-(3-chlorobenzyl)hexanamide;

2-[N-(4-phenylbenzenecarbonyl)]amino-6-(trans-2-(3-quinolinyl)cyclopropan-1-amino)-N-(3-chlorobenzyl)hexanamide;

2-[N-(4-phenylbenzenecarbonyl)]amino-6-(trans-2-(4-quinolinyl)cyclopropan-1-amino)-N-(3-chlorobenzyl)hexamide;

2-[N-(4-phenylbenzenecarbonyl)]amino-6-(trans-2-(2-pyridinyl)cyclopropan-1-amino)-N-(3-chlorobenzyl)hexanamide;

2-[N-(4-phenylbenzenecarbonyl)]amino-6-(trans-2-(3-pyridinyl)cyclopropan-1-amino)-N-(3-chlorobenzyl)hexanamide;

2-[N-(4-phenylbenzenecarbonyl)]amino-6-(trans-2-(4-pyridinyl)cyclopropan-1-amino)-N-(3-chlorobenzyl)hexanamide;

2-[N-(4-phenylbenzenecarbonyl)]amino-6-(trans-2-(thiophen-2-yl)cyclopropan-1-amino)-N-(3-chlorobenzyl)hexanamide;

2-[N-(4-phenylbenzenecarbonyl)]amino-6-(trans-2-(thiophen-3-yl)cyclopropan-1-amino)-N-(3-chlorobenzyl)hexanamide;

2-[N-(4-phenylbenzenecarbonyl)]amino-6-(trans-2-(2-thiazolyl)cyclopropan-1-amino)-N-(3-chlorobenzyl)hexanamide;

2-[N-(4-phenylbenzenecarbonyl)]amino-6-(trans-2-(5-thiazolyl)cyclopropan-1-amino)-N-(3-chlorobenzyl)hexanamide;

2-[N-(4-phenylbenzenecarbonyl)]amino-6-(trans-2-(4-thiazolyl)cyclopropan-1-amino)-N-(3-chlorobenzyl)hexanamide;

2-[N-(4-phenylbenzenecarbonyl)]amino-6-(trans-2-(2-benzothiazolyl)cyclopropan-1-amino)-N-(3-chlorobenzyl)hexanamide; and 2-[N-(4-phenylbenzenecarbonyl)]amino-6-(trans-2-(2-benzoxazolyl)cyclopropan-1-amino)-N-(3-chlorobenzyl)hexanamide.

The compound of the present invention may form a salt with a pharmaceutically acceptable acid. Examples of such acid include: inorganic acids such as hydrochloric acid, hydrobromic acid, nitric acid, sulfuric acid, and phosphoric acid; and organic acids such as oxalic acid, malonic acid, succinic acid, maleic acid, fumaric acid, lactic acid, malic acid, citric acid, tartaric acid, benzoic acid, trifluoroacetic acid, acetic acid, methanesulfonic acid, and p-toluenesulfonic acid.

The compound of the present invention may be a solvate such as a hydrate. The solvent is not particularly limited as long as the solvent is pharmaceutically acceptable.

The compound of the present invention may be in the form of a pharmacologically acceptable prodrug of the compound represented by the general formula (I). The prodrug refers to a compound that generates the compound represented by the general formula (I) through an in vivo metabolism action.

The compound of the present invention may be suitably used as a pharmaceutical composition or LSD1 inhibitor to be described later.

Production Method

The compound represented by the general formula (I) may be produced, for example, by a synthesis method in conformity with the following reaction scheme (A) or reaction scheme (B).

Reaction Scheme A
Reaction steps of the reaction scheme A are described below.
Step (a-1)

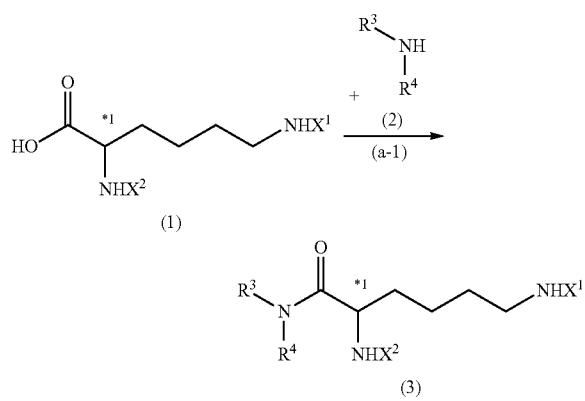

[In the formulae: $R^3$, $R^4$, and *1 are the same as those described above; and $X^1$ and $X^2$ each represent a protective group.]

A compound (1) is a lysine derivative obtained by introducing a protective group into each of amino groups of lysine. The introduction of the protective groups $X^1$ and $X^2$ may be performed by a conventional method. The protective groups $X^1$ and $X^2$ may be identical to or different from each other and are preferably different protective groups, particularly preferably protective groups having different deprotection conditions.

Examples of such protective group include a tert-butoxycarbonyl group (Boc group), a benzyloxycarbonyl group (Cbz group), and a 9-fluorenylmethoxycarbonyl group (Fmoc group). From such a viewpoint that a protective group to be deprotected later is stable under conditions for deprotecting a protective group to be deprotected first, as preferred combinations of the protective group to be deprotected first and the protective group to be deprotected later, there are given, for example, a combination of the Cbz group and the Boc group, a combination of the Boc group and the Cbz group, and a combination of the Fmoc group and the Boc group. In the reaction scheme A, $X^2$ is deprotected first and $X^1$ is deprotected later.

A carboxyl group of the compound (1) is subjected to a condensation reaction with an amino group of a compound (2). Thus, a compound (3) having an amide bond is obtained. For example, 1 mol of the compound (1) may be subjected to a reaction with about 0.1 mol to 10 mol, preferably about 0.5 mol to 2 mol of the compound (2).

It should be noted that when $R^3$ and/or $R^4$ of the compound (2) has a reactive functional group such as an amino group, a carboxyl group, or a hydroxy group, it is preferred to protect the reactive functional group with an appropriate protective group. The protective group is deprotected at an appropriate timing in the scheme.

Specific reaction conditions are not particularly limited as long as the conditions are generally used in peptide synthesis. For example, the compound (1) may be subjected to a reaction with the compound (2) in the presence of a coupling reagent such as: N,N'-dicyclohexylcarbodiimide (DCC); a water-soluble carbodiimide such as 1-ethyl-3-(3-dimethylaminopropyl)carbodiimide hydrochloride (EDCI.HCl); or a BOP reagent such as a benzotriazol-1-yloxy-trisdimethylamino- phosphonium salt (BOP) or (benzotriazol-1-yloxy) tripyrrolidinophosphonium hexafluorophosphate (PyBOP). When the water-soluble carbodiimide is used as the coupling reagent, it is preferred to add 1-hydroxybenzotriazole (HOBt), 1-hydroxy-7-azabenzotriazole (HOAt), or the like because the reaction advantageously proceeds. As necessary, 0.1 mol to an excess, preferably about 0.5 mol to 10 mol of a basic compound such as pyridine, triethylamine, or 4-(dimethylamino)pyridine (DMAP) may be further added.

A reaction temperature, a reaction time, and the amount of each reagent to be used may each be appropriately set by a person skilled in the art. For example, the reaction temperature may be set to from about 10° C. to 40° C. The reaction time may be set to from about 30 minutes to 24 hours. The amount of each reagent to be used may be set to from 0.1 mol to an excess, preferably from about 0.5 mol to 10 mol with respect to 1 mol of the compound (1).

When the reaction is performed in an appropriate solvent, the reaction advantageously proceeds. Examples of the solvent include, but are not limited to, organic solvents such as ethyl acetate, N,N-dimethylformamide (DMF), dimethyl sulfoxide (DMSO), 1,4-dioxane, tetrahydrofuran (THF), acetonitrile, and dichloromethane. The solvent may be any of a single solvent and a mixed solvent of two or more solvents.

Step (a-2)

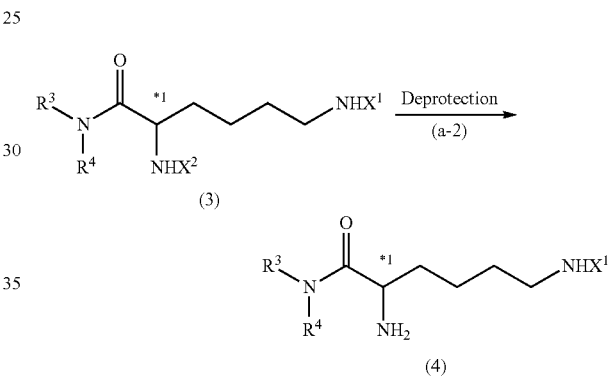

[In the formulae, $R^3$, $R^4$, $X^1$, $X^2$, and *1 are the same as those described above.]

The protective group $X^2$ of the compound (3) is deprotected. Thus, a compound (4) is obtained. A deprotection reaction may be appropriately selected depending on the protective group. For example, when the protective group is a Boc group, the deprotection may be performed by using 0.1 mol to an excess, preferably about 0.5 mol to 10 mol of an acid catalyst such as trifluoroacetic acid (TFA) with respect to 1 mol of a raw material compound. When the protective group is a Cbz group, the deprotection may be performed by using 0.1 mol to an excess, preferably about 0.5 mol to 10 mol of piperidine as well, or by hydrogenation in the presence of 0.1 mol to an excess, preferably about 0.5 mol to 10 mol of a catalyst (e.g., a palladium catalyst). When the protective group is an Fmoc group, the deprotection may be performed by using 0.1 mol to an excess, preferably about 0.5 mol to 10 mol of a secondary amine such as piperidine or morpholine.

A reaction temperature and a reaction time may each be appropriately set by a person skilled in the art. For example, the reaction temperature may be set to from about 10° C. to 40° C. The reaction time may be set to from about 30 minutes to 24 hours.

When the reaction is performed in an appropriate solvent, the reaction advantageously proceeds. Examples of the solvent include, but are not limited to, organic solvents such as ethyl acetate, N,N-dimethylformamide (DMF), dimethyl sulfoxide (DMSO), 1,4-dioxane, tetrahydrofuran (THF), acetonitrile, and dichloromethane. The solvent may be any of a single solvent and a mixed solvent of two or more solvents.

Step (a-3)

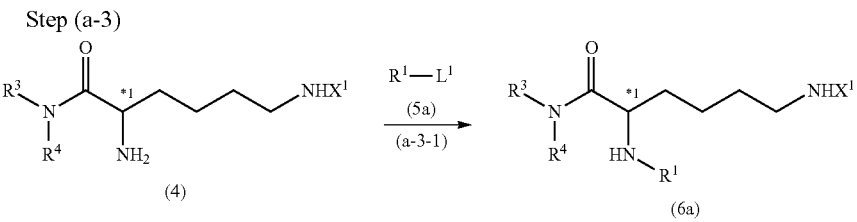

[In the formulae: $R^3$ and $R^4$, $X^1$, and *1 are the same as those described above; $R^1$ and $R^2$ are the same as those described above (provided that none of $R^1$ and $R^2$ represents a hydrogen atom in this step); and $L^1$ and $L^2$ each represent a leaving group.]

The compound (4) is subjected to a reaction with a compound (5a). Thus, a compound (6a) is obtained (Step (a-3-1)). Then, the compound (6a) is subjected to a reaction with a compound (5b). Thus, a compound (6b) is obtained (Step (a-3-2)). Specific examples of the leaving groups $L^1$ and $L^2$ include halogens (e.g., iodine, bromine, and chlorine), p-toluenesulfonyloxy (tosyloxy), and methylsulfonyloxy (mesyloxy).

A reaction temperature, a reaction time, and the amount of each reagent to be used may each be appropriately set by a person skilled in the art. For example, the reaction temperature may be set to fall within a range of from 0° C. to a temperature at which the solvent boils (e.g., about 100° C.). The reaction time may be set to from about 30 minutes to 24 hours. The amount of each reagent to be used may be set to 0.5 mol to an excess, preferably about 1 mol to 10 mol of each of the compound (5a) and the compound (5b) with respect to 1 mol of the compound (4). As necessary, the reaction may be performed in the presence of a base such as an alkali metal carbonate or an alkali metal hydrogen carbonate.

When the reaction is performed in an appropriate solvent, the reaction advantageously proceeds. Examples of the solvent include, but are not limited to, organic solvents such as ethyl acetate, N,N-dimethylformamide (DMF), dimethyl sulfoxide (DMSO), 1,4-dioxane, tetrahydrofuran (THF), acetonitrile, and dichloromethane. The solvent may be any of a single solvent and a mixed solvent of two or more solvents.

Step (a-4)

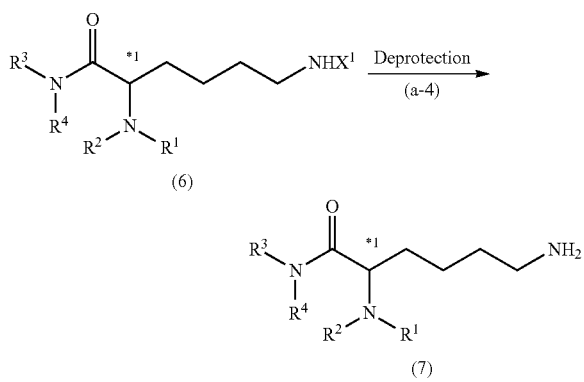

[In the formulae, $R^1$ to $R^4$, $X^1$, and *1 are the same as those described above.]

The protective group $X^1$ of the compound (6) is deprotected. Thus, a compound (7) is obtained. The compound (4), the compound (6a), or the compound (6b) may be used as the compound (6). A deprotection reaction may be appropriately selected depending on the protective group. Specific examples thereof are the same as those described in Step (a-1) above.

Step (a-5)

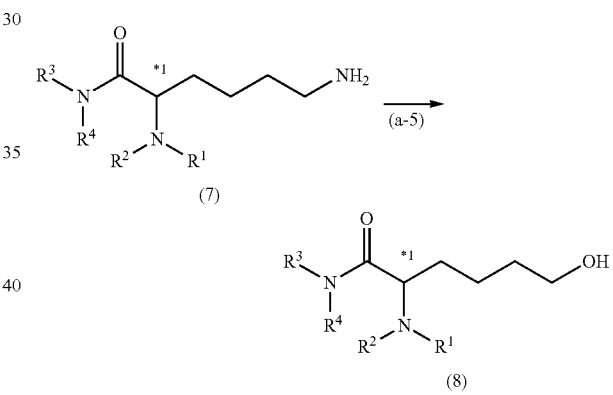

[In the formulae, $R^1$ to $R^4$ and *1 are the same as those described above.]

An amino group of the compound (7) is converted to a hydroxy group. Thus, a compound (8) is obtained. For example, the compound (8) may be obtained by subjecting a diazonium salt obtained by the diazotization of the amino group of the compound (7) to pyrolysis in an acidic aqueous solution. A diazotization reaction may be typically performed in the presence of 0.1 mol to an excess, preferably about 0.5 mol to 10 mol of a diazotization reagent (e.g., a nitrite such as sodium nitrite) with respect to 1 mol of the compound (7). As the acidic aqueous solution, for example, acetic acid may be used.

A reaction temperature and a reaction time may each be appropriately set by a person skilled in the art. The reaction temperature of the diazotization reaction may be set to from about 0° C. to 40° C., and it is particularly preferred to perform the reaction at low temperature (e.g., 5° C. or less). A pyrolysis reaction may be performed at from about 50° C. to 100° C., and as necessary, a temperature equal to or less than the boiling point of a solvent to be used. The reaction time may be set to from about 5 minutes to 12 hours for each of the diazotization reaction and the pyrolysis reaction.

Step (a-6)

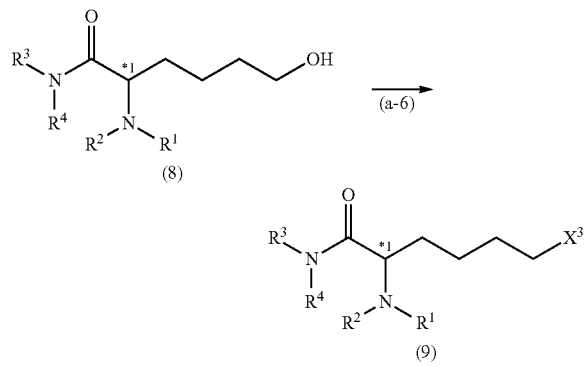

[In the formulae: $R^1$ to $R^4$ and *1 are the same as those described above; and $X^3$ represents a leaving group.]

A leaving group is introduced into a hydroxy group of the compound (8). Thus, a compound (9) is obtained. Specific examples of the leaving group $X^3$ include halogens (e.g., iodine, bromine, and chlorine), p-toluenesulfonyloxy (tosyloxy), and methylsulfonyloxy (mesyloxy).

When the leaving group is a halogen, for example, 1 mol of the compound (8) may be subjected to a reaction with about 0.1 mol to an excess mol, preferably about 0.5 mol to 10 mol of a halogen source such as a halogen molecule or N-halogenated succinimide in the presence of about 0.1 mol to an excess mol, preferably about 0.5 mol to 10 mol of triphenylphosphine.

When the leaving group is p-toluenesulfonyloxy or methylsulfonyloxy for example, 1 mol of the compound (8) may be subjected to a reaction with about 0.1 mol to an excess mol, preferably about 0.5 mol to 10 mol of p-toluenesulfonyl chloride or methylsulfonyl chloride. As necessary, 0.1 mol to an excess, preferably about 0.5 mol to 10 mol of a basic compound such as pyridine, triethylamine, or 4-(dimethylamino)pyridine (DMAP) may be further added.

A reaction temperature and a reaction time may each be appropriately set by a person skilled in the art. For example, the reaction temperature may be set to from about 10° C. to 40° C. The reaction time may be set to from about 30 minutes to 24 hours.

When the reaction is performed in an appropriate solvent, the reaction advantageously proceeds. Examples of the solvent include, but are not limited to, organic solvents such as pyridine, ethyl acetate, N,N-dimethylformamide (DMF), dimethyl sulfoxide (DMSO), 1,4-dioxane, tetrahydrofuran (THF), acetonitrile, and dichloromethane. The solvent may be any of a single solvent and a mixed solvent of two or more solvents.

Step (a-7)

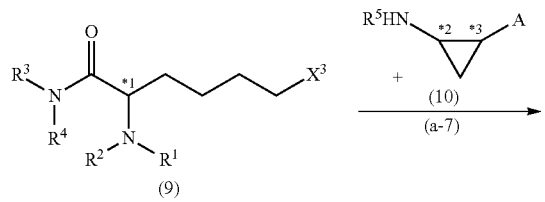

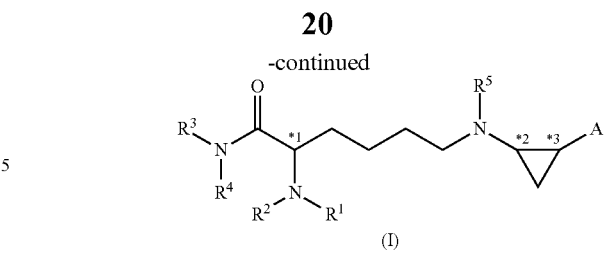

[In the formulae, $R^1$ to $R^5$, A, $X^3$, and *1 to *3 are the same as those described above.]

The compound (9) is subjected to a reaction with a compound (10) or a salt thereof. Thus, a compound (I) or a salt thereof is obtained. For example, 1 mol of the compound (9) may be subjected to a reaction with about 0.1 mol to 10 mol, preferably about 0.5 mol to 2 mol of the compound (10). The reaction advantageously proceeds in the presence of about 0.1 mol to an excess mol, preferably about 0.5 mol to 10 mol of a base such as an alkali metal carbonate or an alkali metal hydrogen carbonate (e.g., potassium carbonate or lithium carbonate) as necessary.

The compound (9) may be produced, for example, by a general organic synthesis technology in accordance with or in conformity with a known production method for trans-2-phenylcyclopropylamine (tranylcypromine).

A reaction temperature and a reaction time may each be appropriately set by a person skilled in the art. For example, the reaction temperature may be set to from about 10° C. to 40° C. The reaction time may be set to from about 30 minutes to 24 hours.

When the reaction is performed in an appropriate solvent, the reaction advantageously proceeds. Examples of the solvent include, but are not limited to, organic solvents such as ethyl acetate, N,N-dimethylformamide (DMF), dimethyl sulfoxide (DMSO), 1,4-dioxane, tetrahydrofuran (THF), acetonitrile, and dichloromethane. The solvent may be any of a single solvent and a mixed solvent of two or more solvents.

Reaction Scheme B

In the reaction scheme B, steps corresponding to Steps (a-4) to (a-7) are performed prior to steps corresponding to Steps (a-2) and (a-3) in the reaction scheme A. That is, Step (b-1) of the reaction scheme B is performed in conformity with Step (a-1) of the reaction scheme A, Steps (b-2) to (b-5) of the reaction scheme B are performed in conformity with Steps (a-4) to (a-7) of the reaction scheme A, respectively, and Steps (b-6) and (b-7) of the reaction scheme B are performed in conformity with Steps (a-2) and (a-3) of the reaction scheme A, respectively.

In the reaction scheme B, $X^1$ is deprotected first and $X^2$ is deprotected later.

Steps of the reaction scheme B are shown below.

Step (b-1)

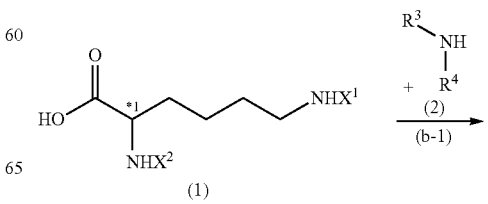

-continued

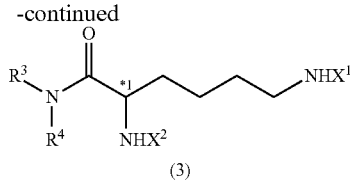

[In the formulae, $R^3$, $R^4$, $X^1$, $X^2$, and *1 are the same as those described above.]

Step (b-2)

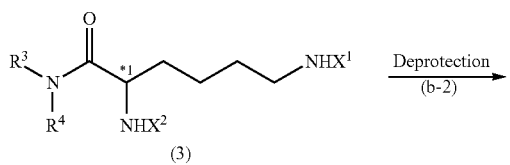

[In the formulae, $R^3$, $R^4$, $X^1$, $X^2$, and *1 are the same as those described above.]

Step (b-3)

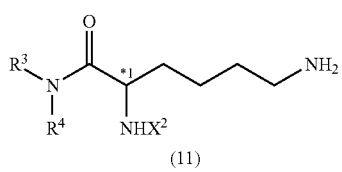

[In the formulae, $R^3$, $R^4$, $X^2$, and *1 are the same as those described above.]

Step (b-4)

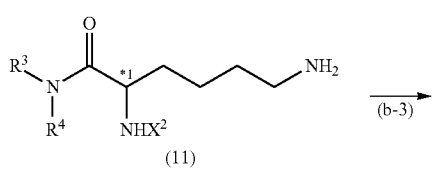

[In the formulae, $R^3$, $R^4$, $X^2$, and *1 are the same as those described above.]

Step (b-5)

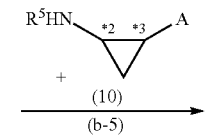

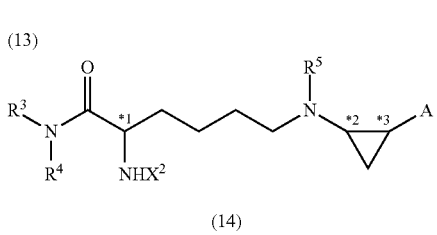

[In the formulae, $R^3$ to $R^5$, A, $X^2$, and *1 to *3 are the same as those described above.]

Step (b-6)

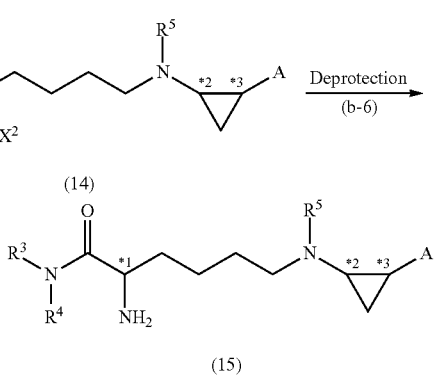

[In the formulae, $R^3$ to $R^5$, A, $X^2$, and *1 to *3 are the same as those described above.]

Step (b-7)

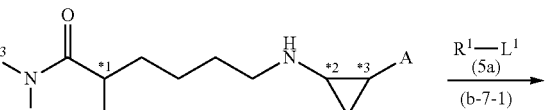

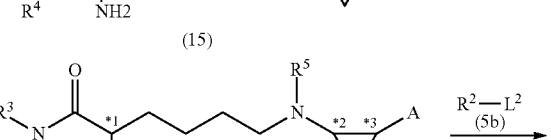

[In the formulae: $R^3$ to $R^5$, A, *1 to *3, $L^1$ and $L^2$ are the same as those described above; and $R^1$ and $R^2$ are the same as those described above (provided that none of $R^1$ and $R^2$ represents a hydrogen atom in this step).]

In the reaction scheme B, a compound (14), a compound (15), a compound (16), or a compound (17) may be used as the compound represented by the general formula (I).

In the above-mentioned production method, a compound of interest may be obtained, as necessary, via an isolation step involving filtration, concentration, extraction, and the like and/or a purification step involving column chromatography, recrystallization, and the like.

Thus, the compound of the present invention is produced. The synthesis of the compound may be confirmed, for example, by known means such as $^1$H-NMR measurement, $^{13}$C-NMR measurement, or mass spectrometry.

2. Pharmaceutical Composition and LSD1 Inhibitor

The compound or the salt thereof of the present invention has high and selective inhibitory activity against lysine-specific histone demethylase 1 (LSD1) as demonstrated in Examples to be described later. Therefore, the present invention provides an LSD1 inhibitor including as an active ingredient a compound represented by the general formula (I) or a salt thereof. The LSD1 inhibitor may be specifically used as a pharmaceutical composition (pharmaceutical or pharmaceutical preparation) or a reagent for a biological test.

The administration target of a pharmaceutical composition of the present invention is not particularly limited. Suitable examples of the administration target include mammals including humans. The race, sex, and age of the humans are not particularly limited. As mammals other than the humans, there are given pet animals such as dogs and cats.

A pharmaceutical composition according to one embodiment of the present invention is provided as a pharmaceutical composition for treating malignant tumor or cancer (antitumor agent or anticancer agent). The kind of malignant tumor or cancer to be treated is not particularly limited as long as the compound of the present invention is sensitive thereto. Specific examples thereof include: solid cancers in the stomach, large intestine, lung, liver, prostate gland, pancreas, esophagus, bladder, gallbladder/bile duct, breast, uterus, thyroid, and ovary; and leukemia including acute myeloid leukemia, acute lymphoid leukemia, chronic myeloid leukemia, and chronic lymphoid leukemia. As a preferred treatment target, there is given acute myeloid leukemia including acute myeloid leukemia, acute promyelocytic leukemia, acute monocytic leukemia, acute erythroid leukemia, and myelodysplastic syndromes, which progress to leukemia. In this case, the pharmaceutical composition of the present invention is a therapeutic drug for acute myeloid leukemia.

As demonstrated in Examples of the present application, the compound or the salt thereof of the present invention can inhibit the cell growth of various cancer cells. In addition, the pharmaceutical composition of the present invention may also be verified for its effectiveness by being administered to disease animal models such as mice. In addition, in Schenk T et al: Nature Medicine 18, 605-11 (2012), there is a disclosure that the compound having LSD1 inhibitory activity may be used as a therapeutic drug for acute myeloid leukemia. The compound or the salt thereof of the present invention has LSD1-selective inhibitory activity, and hence is considered to be a preferred pharmaceutical composition with little side effects.

A pharmaceutical composition according to another embodiment of the present invention is provided as a pharmaceutical composition for treating a viral disease (antiviral drug). The pathogenic virus of the viral disease is not particularly limited and may be any of a DNA virus and an RNA virus.

Examples of the DNA virus include: viruses of the family Herpesviridae such as herpes simplex virus type 1 (HSV-1), herpes simplex virus type 2 (HSV-2), varicella-zoster virus (VZV), human cytomegalovirus (HCMV), and EB virus (EBV); viruses of the family Adenoviridae; viruses of the family Papovaviridae such as papillomavirus; viruses of the family Parvoviridae; and viruses of the family Hepadnaviridae such as hepatitis B virus (HBV).

Examples of the RNA virus include: viruses of the family Reoviridae such as rotavirus; viruses of the family Paramyxoviridae such as measles virus; viruses of the family Orthomyxoviridae such as influenza viruses (type A, type B, and type C); viruses of the family Picornaviridae such as hepatitis A virus (HAV) and poliovirus; viruses of the family Flaviviridae such as hepatitis C virus (HCV); and viruses of the family Retroviridae such as HTLV-1 and human immunodeficiency virus (HIV).

In Liang Y et al.: Nature Medicine 15, 1312-1317 (2009), there is a disclosure that the compound having LSD1 inhibitory activity has an antiviral action. The antiviral action is probably due to the suppression of transcription of a virus-derived gene via the inhibition of LSD1, although the present invention is not restricted thereto. The compound or the salt thereof of the present invention has LSD1-selective inhibitory activity, and hence is considered to be a preferred pharmaceutical composition with little side effects.

A pharmaceutical composition according to another embodiment of the present invention is provided as a pharmaceutical composition for treating hemoglobinopathy (therapeutic drug for hemoglobinopathy).

Examples of the hemoglobinopathy include sickle cell disease and thalassemia ($\alpha$-thalassemia and $\beta$-thalassemia; in particular, $\beta$-thalassemia).

In Shi L, et al: Nat Medicine 19, 291-294 (2013), there is a disclosure that the compound having LSD1 inhibitory activity is effective for the treatment of hemoglobinopathy. It is considered that the inhibition of LSD1 enhances the expression amount of fetal hemoglobin ($\gamma$-globin), which replaces $\alpha$- or $\beta$-hemoglobin whose expression is suppressed owing to a genetic abnormality, and thus contributes to the alleviation of a symptom, although the present invention is not restricted thereto.

The pharmaceutical composition of the present invention is obtained by using a pharmaceutically acceptable additive, for example, a generally used diluent or excipient such as a filler, an extender, a binder, a wetting agent, a disintegrant, a surfactant, or a lubricant to blend the compound of the present invention into a general pharmaceutical preparation.

The administration route of the pharmaceutical composition according to the present invention is not limited, and this preparation may be administered by a method depending on the form of the preparation, the age and sex of a patient, a pathological condition, and other conditions. For example, a tablet, a pill, a solution, a suspension, an emulsion, a granule, and a capsule are orally administered. An injection is intravenously, intramuscularly, intracutaneously, subcutaneously, or intraperitoneally administered. A suppository is intrarectally administered.

The dosage of the pharmaceutical composition of the present invention is not particularly limited as long as the dosage is such an effective amount that drug efficacy is expressed. In general, however, in terms of the weight of the compound represented by the general formula (I) or the salt thereof, which is an active ingredient, usually in the case of oral administration, the dosage is from 0.1 mg to 1,000 mg per day, preferably from 0.5 mg to 50 mg per day in adult humans, and in the case of parenteral administration, the dosage is from 0.01 mg to 100 mg per day, preferably from 0.1 mg to 10 mg per day. The daily dosage is preferably administered in one portion or two or three divided portions, and may be appropriately increased or decreased depending on age, a pathological condition, and a symptom.

The pharmaceutical composition of the present invention may be applied in combination with any other pharmaceutical depending on a treatment target. When the treatment target is malignant tumor or cancer, examples of the pharmaceutical that may be used in combination with the pharmaceutical composition of the present invention include a known antitumor agent and anticancer agent. When the treatment target is acute myeloid leukemia such as acute myeloid leukemia, an example of the pharmaceutical that may be used in combination with the pharmaceutical composition of the present invention is all-trans retinoic acid (tretinoin).

The present invention also provides: a use of a compound represented by the general formula (I) or a pharmaceutically acceptable salt thereof, for treating the above-mentioned treatment target or the like; a use of a compound represented by the general formula (I) or a pharmaceutically acceptable salt thereof, for producing a pharmaceutical for treating the above-mentioned treatment target or the like; and a compound represented by the general formula (I) or a pharmaceutically acceptable salt thereof, for treating the above-mentioned treatment target or the like to be described later.

EXAMPLES

Now, Examples for embodying the present invention are described in detail.
<Conditions (1) for HPLC>
Conditions for HPLC used mainly for the fractionation of a compound are shown below.
Column: Inertsil ODS-3 (250 mm×φ20 mm)
Measuring wavelength: 254 nm
Flow rate: 10.0 mL/min
[i] Solvent A: water (0.1% TFA)
Solvent B: MeCN (0.1% TFA)
Gradient conditions
Gradient (I): 0 min (30% B)-2 min (30% B)-25 min (70% B)-30 min (70% B)-35 min (30% B)-40 min (30% B)
[ii] Solvent A: water (0.1% TFA)
Solvent B: MeOH (0.1% TFA)
Gradient (II): 0 min (30% B)-2 min (30% B)-25 min (70% B)-35 min (70% B)-40 min (30% B)-45 min (30% B)
Gradient (III): 0 min (25% B)-2 min (25% B)-20 min (70% B)-25 min (70% B)-28 min (25% B)-30 min (25% B)
Gradient (IV): 0 min (35% B)-30 min (100% B)-37 min (100% B)-40 min (35% B)-45 min (35% B).
<Conditions (2) for HPLC>
Conditions for HPLC used mainly for the analysis of a compound are shown below.
Column: ODS-3 (150 mm×φ4.6 mm)
Measuring wavelength: 213 nm
Injection volume: 20 μL
Flow rate: 1.0 mL/min
[i] Solvent A: water (0.1% TFA)
Solvent B: MeCN (0.1% TFA)
Gradient conditions
Gradient (I): 0 min (30% B)-2 min (30% B)-20 min (70% B)-30 min (70% B)-35 min (30% B)-40 min (30% B)
Gradient (VI): 0 min (35% B)-25 min (95% B)-30 min (95% B)-35 min (35% B)-40 min (35% B)
Gradient (VII): 0 min (35% B)-30 min (95% B)-35 min (95% B)-37 min (35% B)-45 min (35% B)
[ii] Solvent A: water (0.1% TFA)
Solvent B: MeOH (0.1% TFA)
Gradient (II): 0 min (35% B)-2 min (35% B)-15 min (75% B)-25 min (75% B)-30 min (35% B)-35 min (35% B)
Gradient (III): 0 min (20% B)-2 min (20% B)-20 min (65% B)-30 min (65% B)-35 min (20% B)-40 min (20% B)
Gradient (IV): 0 min (25% B)-2 min (25% B)-20 min (70% B)-25 min (70% B)-28 min (25% B)-30 min (25% B)
Gradient (V): 0 min (35% B)-25 min (100% B)-30 min (100% B)-35 min (35% B)-40 min (35% B).

[Synthesis of Compound]

Phenylcyclopropylamine derivatives shown below were synthesized in Examples 1 to 21. Details thereof are described below.

Example 1

NCD18

Example 2

NCD29

Example 3

NCD30

Example 4

NCD21

Example 5
NCD22
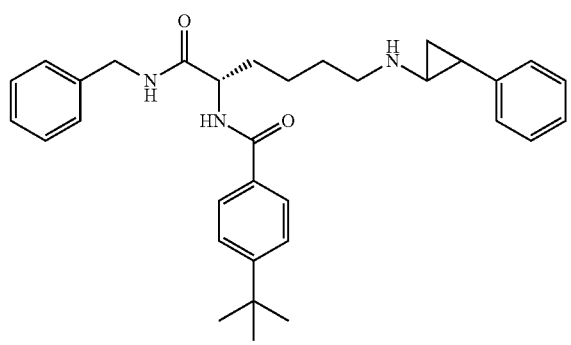
Example 6
NCD23
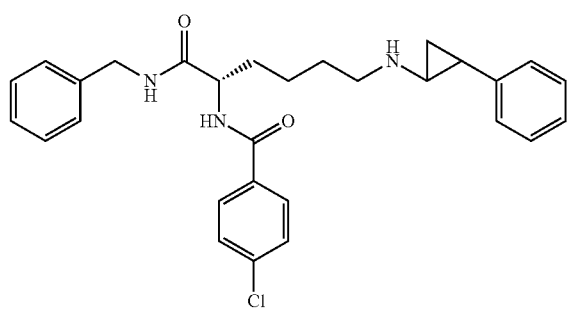
Example 7
NCD24
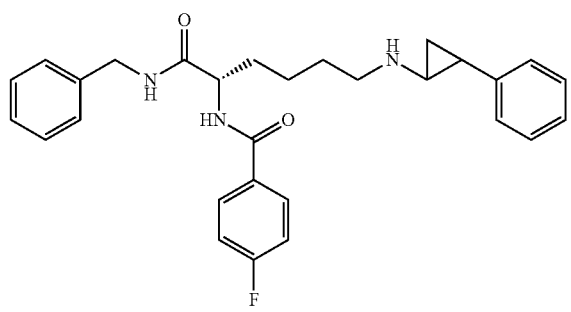
Example 8
NCD25
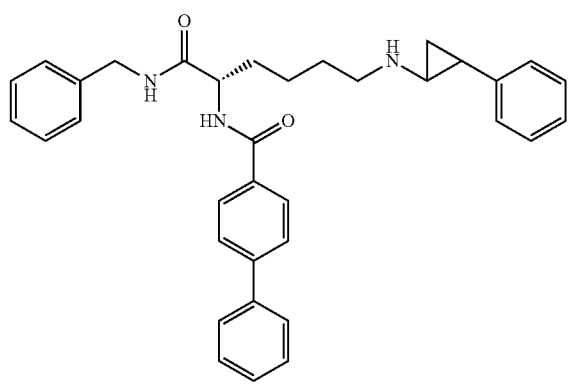
Example 9
NCD26
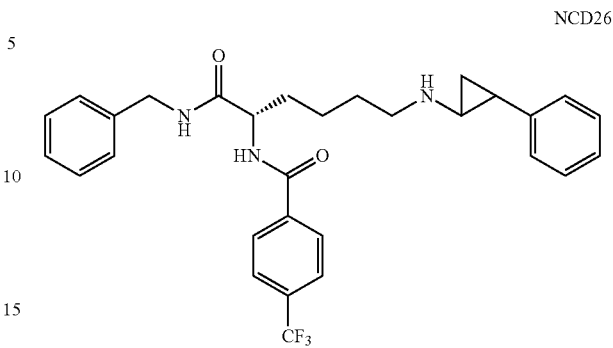
Example 10
NCD27
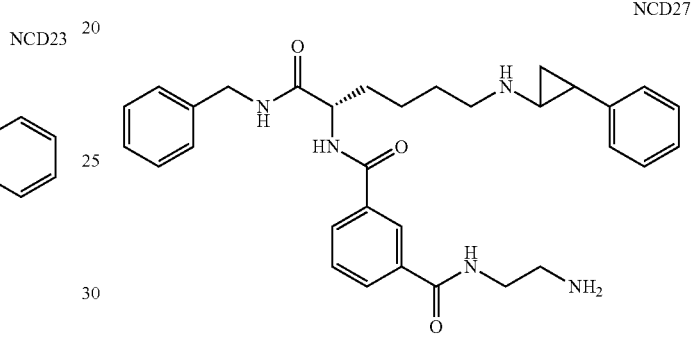
Example 11
NCD28
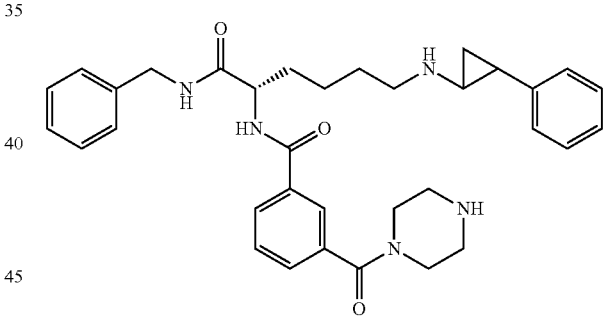
Example 12
NCD31
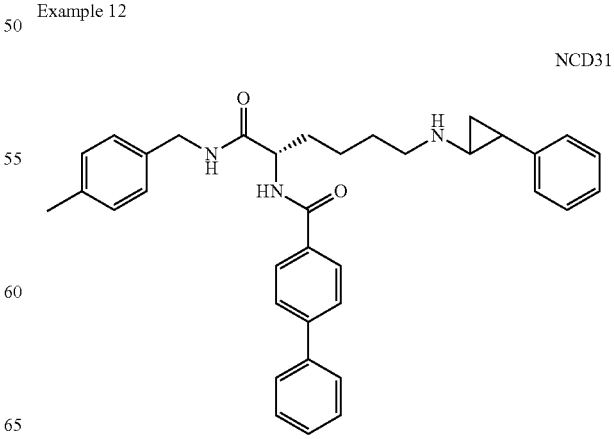

Example 13
NCD32
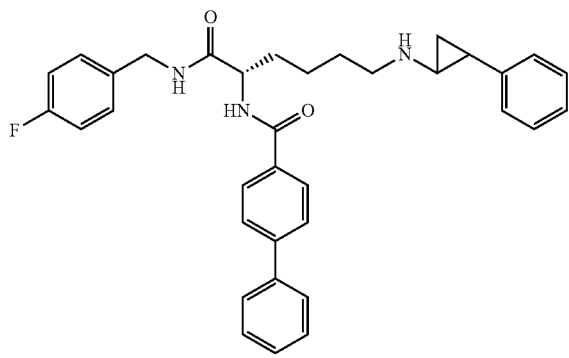
Example 14
NCD34
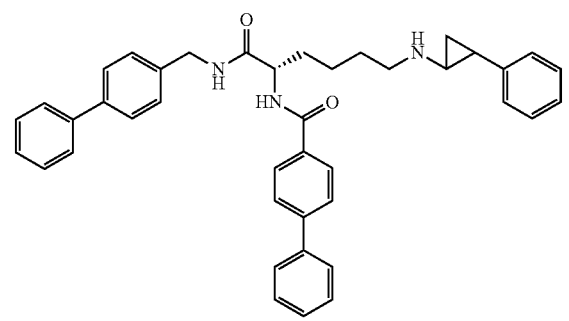
Example 15
NCD35
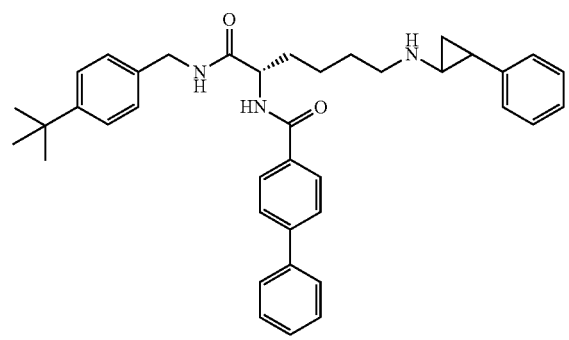
Example 16
NCD36
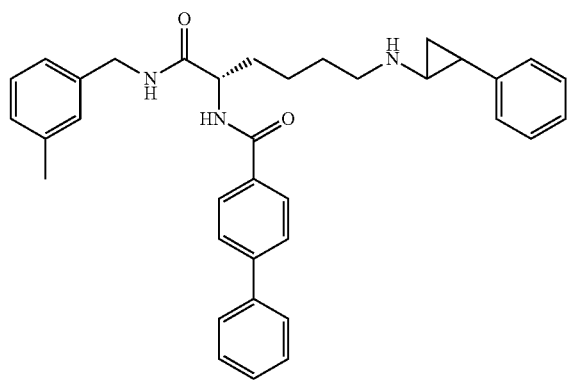
Example 17
NCD37
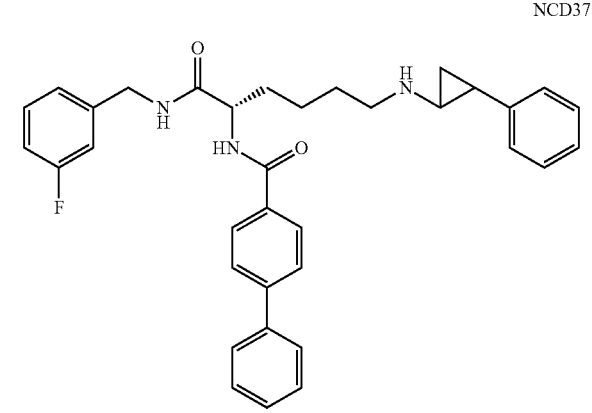
Example 18
NCD39
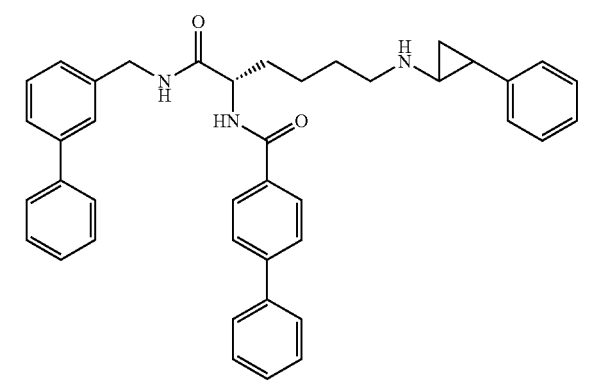
Example 19
NCD41
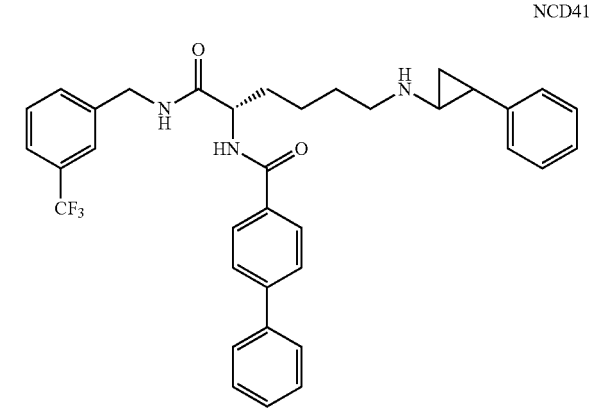

Example 20

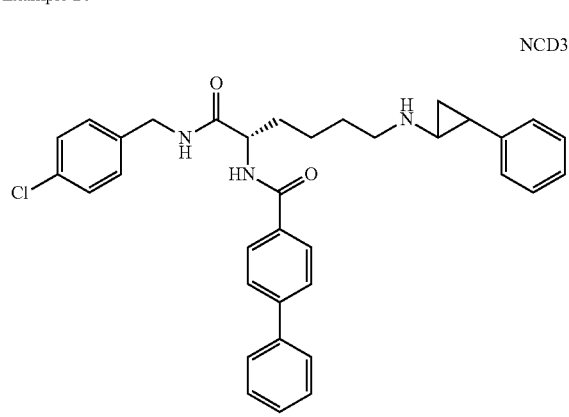

NCD33

Example 21

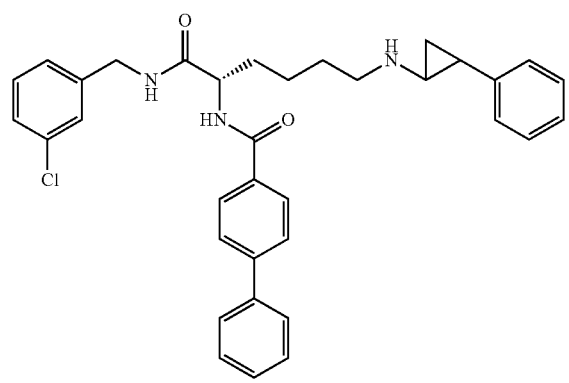

NCD38

Synthesis of Phenylcyclopropylamine Derivative of Example 1

2-(Benzenecarbonyl)amino-N-benzyl-6-(trans-2-phenyl-cyclopropan-1-amino)hexanamide (Example 1, NCD18) was synthesized in accordance with the following synthesis route.

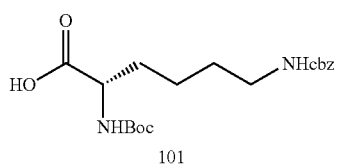

101 benzylamine, Et₃N
———————→
EDCI, HOBt, DMF

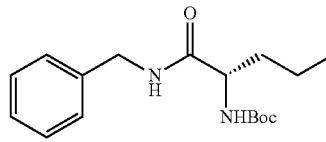

102

HCl
———————→
1,4-dioxane, CH₂Cl₂

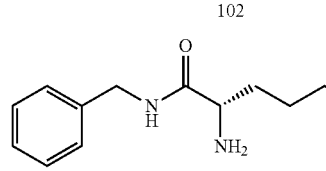

103 benzoic acid, Et₃N
———————→
EDCI, HOBt, DMF

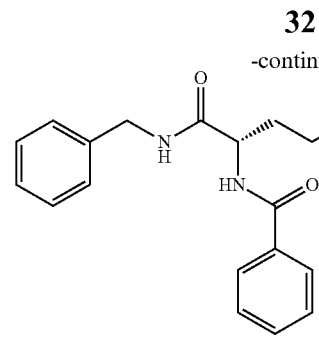

104

H₂, Pd/C
———————→
MeOH

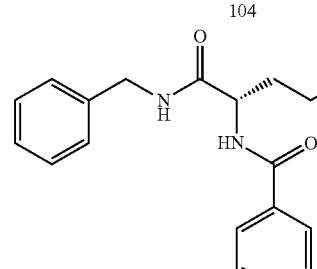

105

NaNO₂, acetic acid
———————→
H₂O, MeCN

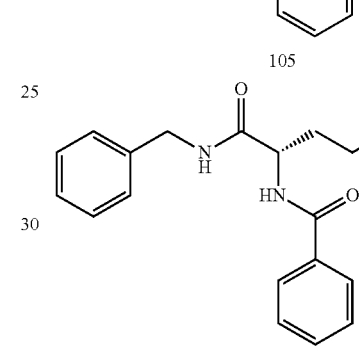

106

MsCl, DMAP, Et₃N
———————→
CH₂Cl₂

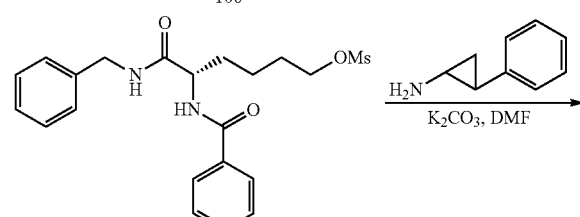

107

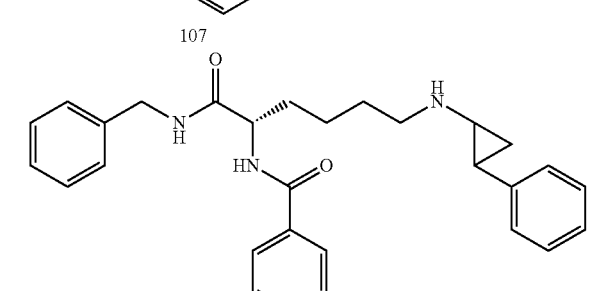

NCD18
Example 1

Step 1-1: Synthesis of 6-(N-Benzyloxycarbonyl)amino-2-(N-tert-butoxycarbonyl)amino-N-benzyl-hexanamide (102)

N-α-tert-Butoxycarbonyl-N-ε-benzyloxycarbonyl-1-lysine (101) (1.01 g) was dissolved in N,N-dimethylformamide (40 ml). To the solution were added EDCI.HCl (762 mg), HOBt.H₂O (609 mg), triethylamine (546 mg), and benzylamine (338 mg), and the mixture was stirred at room temperature for 13.5 hours. The reaction liquid was diluted with chloroform (100 ml), washed with water (600 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: n-hexane:ethyl acetate=1:1) to give a compound (102) (1.16 g, yield: 94%) as a white solid. $^1$H NMR data on the compound (102) is shown below.

$^1$H-NMR (DMSO-$d_6$ 500 MHz, δ; ppm) 8.30 (1H, t, J=5.99 Hz), 7.38-7.20 (11H, m), 6.86 (H, d, J=7.99 Hz), 5.00 (2H, s), 4.27 (2H, t, J=5.24 Hz), 3.89 (1H, q, J=7.32 Hz), 2.96 (2H, d, J=6.49 Hz), 1.57-1.17 (15H, m).

Step 1-2: Synthesis of 2-Amino-6-(N-benzyloxycarbonyl)amino-N-benzylhexanamide Hydrochloride (103)

7-(N-Benzyloxycarbonyl)amino-2-(N-tert-butoxycarbonyl)amino-N-benzylhexanamide (102) (1.10 g) obtained in Step 1-1 was dissolved in dichloromethane (15 ml). To the solution was added a solution of 4 N hydrochloric acid in 1,4-dioxane (5.9 ml), and the mixture was stirred at room temperature for 2 hours. The generated white precipitate was collected by filtration to give a compound (103) (908 mg, yield: 95%) as a white solid. $^1$H NMR data on the compound (103) is shown below.

$^1$H-NMR (DMSO-$d_6$, 500 MHz, δ; ppm) 8.92 (1H, t, J=5.74 Hz), 8.12 (3H, s), 7.38-7.25 (11H, m), 5.01 (2H, s), 4.34 (2H, d, J=5.99 Hz), 3.75 (1H, m), 2.97 (2H, t, J=6.74 Hz), 1.73-1.71 (2H, m), 1.42-1.28 (4H, m).

Step 1-3: Synthesis of 2-(N-Benzenecarbonyl)amino-6-(N-benzyloxycarbonyl)amino-N-benzylhexanamide (104)

2-Amino-7-(N-benzyloxycarbonyl)amino-N-benzylhexanamide hydrochloride (103) (908 mg) obtained in Step 1-2 was dissolved in N,N-dimethylformamide (28 ml). To the solution were added EDCI.HCl (726 mg), HOBt.H₂O (588 mg), triethylamine (765 mg), and benzoic acid (372 mg), and the mixture was stirred at room temperature for 19 hours. The reaction liquid was diluted with chloroform (200 ml), washed with water (600 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: chloroform) to give a compound (104) (1.05 g, yield: 99%) as a white solid. $^1$H NMR data on the compound (104) is shown below.

$^1$H-NMR (DMSO-$d_6$, 500 MHz, δ; ppm) 8.49-8.43 (2H, m), 7.91 (2H, d, J=6.99 Hz), 7.53-7.22 (14H, m), 4.98 (2H, s), 4.44-4.43 (1H, m), 4.29 (2H, d, J=5.49 Hz), 2.98 (2H, s), 1.41-1.24 (4H, m).

Step 1-4: Synthesis of 6-Amino-2-(N-benzenecarbonyl)amino-N-benzylhexanamide (105)

2-(N-Benzenecarbonyl)amino-6-(N-benzyloxycarbonyl)amino-N-benzylhexanamide hydrochloride (104) (1.05 g) obtained in Step 1-3 was dissolved in methanol (45 ml) and chloroform (15 ml). To the solution was added a 5 wt % palladium-on-activated carbon catalyst (Pd/C) (385 mg), and the mixture was stirred at room temperature for 23 hours under a hydrogen atmosphere. The reaction liquid was filtered through Celite. After that, the filtrate was concentrated and the residue was dissolved again in methanol (16 ml). To the solution was added a 5 wt % palladium-on-activated carbon catalyst (Pd/C) (334 mg), and the mixture was stirred at room temperature for 5.5 hours under a hydrogen atmosphere. The reaction liquid was filtered through Celite. After that, the filtrate was concentrated to give a compound (105) (643 mg, yield: 85%) as a colorless amorphous solid. $^1$H NMR data on the compound (105) is shown below.

$^1$H-NMR (DMSO-$d_6$, 500 MHz, δ; ppm) 8.57-8.53 (2H, m), 7.94 (2H, d, J=7.49 Hz), 7.90 (2H, s) 7.54 (1H, t, J=7.49 Hz), 7.47 (2H, t, J=7.49 Hz), 7.31 (2H, t, J=7.49 Hz), 7.26-7.21 (3H, m), 4.47 (1H, q, J=7.49 Hz), 4.30 (2H, d, J=5.99 Hz), 2.77-2.73 (2H, m), 1.82-1.79 (2H, m), 1.59-1.56 (2H, m) 1.45-1.35 (2H, m).

Step 1-5: Synthesis of 2-(N-Benzenecarbonyl)amino-6-hydroxy-N-benzylhexanamide (106)

2-(N-Benzenecarbonyl)amino-6-amino-N-benzylhexanamide (105) (48 mg) obtained in Step 1-4 was dissolved in water (1.6 ml) and acetonitrile (1.1 ml). To the solution were added sodium nitrite (156 mg) and acetic acid (40.6 mg) under cooling with ice, and the mixture was stirred for 1 hour under cooling with ice. After 1 hour, the reaction liquid was warmed to room temperature and stirred for 1.5 hours. Subsequently, the reaction liquid was heated to 70° C. and stirred for an additional 20 minutes. The reaction liquid was concentrated and extracted with ethyl acetate (60 ml). The organic layer was washed with brine (100 ml), dried over anhydrous sodium sulfate, and filtered. After that, the filtrate was concentrated and the residue was purified by silica gel flash column chromatography (developing solvent: n-hexane:ethyl acetate=2:1 to n-hexane:ethyl acetate=1:6) to give a compound (106) (19.5 mg, yield: 41%) as a pale yellow solid. $^1$H NMR data on the compound (106) is shown below.

$^1$H-NMR (DMSO-$d_6$, 500 MHz, δ; ppm) 8.52-8.47 (2H, m), 7.91 (2H, d, J=7.73 Hz), 7.55-7.53 (1H, m) 7.49-7.46 (2H, m), 7.32-7.29 (2H, m), 7.26-7.21 (3H, m), 4.75 (1H, s), 4.50-4.46 (1H, m), 4.29 (2H, d, J=5.99 Hz), 3.39 (2H, m), 1.82-1.79 (2H, m), 1.77-1.72 (2H, m), 1.43-1.37 (2H, m).

Step 1-6: Synthesis of 2-(N-Benzenecarbonyl)amino-6-(O-methanesulfonyl)-N-benzylhexanamide (107)

2-(N-Benzenecarbonyl)amino-6-hydroxy-N-benzylhexanamide (106) (723 mg) obtained in Step 1-5 was dissolved in dichloromethane (20 ml). To the solution were added methanesulfonyl chloride (375 mg), dimethylaminopyridine (26 mg), and triethylamine (643 mg) under cooling with ice, and the mixture was stirred at room temperature for 1 hour. The reaction liquid was diluted with dichloromethane (20 ml) and washed with water (40 ml), 2 N hydrochloric acid (40 ml), and brine (40 ml). The organic layer was dried over anhydrous sodium sulfate and filtered. After that, the filtrate was concentrated and the residue was purified by silica gel flash column chromatography (developing solvent: n-hexane:ethyl acetate=5:1 to n-hexane:ethyl acetate=3:1) to give a compound (107) (480 mg, yield: 54%) as a white solid. $^1$H NMR data on the compound (107) is shown below.

$^1$H-NMR (DMSO-$d_6$, 500 MHz, δ; ppm) 8.53-8.48 (2H, m), 7.91 (2H, d, J=6.99 Hz), 7.54 (1H, t, J=7.24 Hz), 7.47 (2H, t, J=7.49 Hz), 7.31 (2H, t, J=7.49 Hz), 7.26-7.21 (3H, m), 4.50 (1H, m), 4.30 (2H, d, J=5.99 Hz), 4.18 (2H, t, J=6.49 Hz), 3.14 (3H, s), 1.82-1.77 (2H, m), 1.69-1.67 (2H, m), 1.45-1.39 (2H, m).

Step 1-7: Synthesis of 2-(N-Benzenecarbonyl)amino-6-(trans-2-phenylcyclopropan-1-amino)-N-benzylhexanamide Trifluoroacetate (Example 1, NCD18)

2-(N-Benzenecarbonyl)amino-6-(O-methanesulfonyl)-N-benzylhexanamide (107) (86.4 mg) obtained in Step 1-6 was dissolved in N,N-dimethylformamide (0.7 ml). To the solution were added trans-2-phenylcyclopropylamine hydrochloride (250 mg) and potassium carbonate (129 mg), and the mixture was stirred at 60° C. for 11 hours. The reaction liquid was diluted with dichloromethane (20 ml), washed with saturated aqueous sodium bicarbonate (40 ml) and brine (40 ml), dried over anhydrous sodium sulfate, and filtered. After that, the filtrate was concentrated and the residue was purified by silica gel flash column chromatography (developing solvent: chloroform to chloroform:methanol=80:1) to give a pale yellow solid. The resultant pale yellow solid was further purified by HPLC (Gradient (I)) to give a compound (Example 1, NCD18) (34.2 mg, yield: 29%) as a colorless amorphous solid. $^1$H NMR, $^{13}$C NMR, HRMS (FAB), and purity data on the compound (Example 1, NCD18) are shown below.

$^1$H-NMR (CD$_3$OD, 500 MHz, δ; ppm) 7.86 (2H, d, J=6.99 Hz), 7.55 (1H, t, J=7.24 Hz), 7.46 (2H, t, J=7.74 Hz), 7.31-7.27 (6H, m), 7.23-7.21 (2H, m), 7.16-7.14 (2H, m), 4.61-4.59 (1H, m), 4.41-4.38 (2H, m), 3.18-3.13 (2H, m), 2.95-2.92 (1H, m), 2.44-2.41 (1H, m), 1.96-1.76 (4H, m), 1.53-1.36 (2H, m)

$^{13}$C-NMR (CD$_3$OD, 500 MHz, δ; ppm) 171.4, 170.4, 139.8, 139.3, 135.1, 133.0, 129.8, 129.6, 129.5, 128.5, 128.5, 128.2, 128.1, 127.4, 55.0, 44.1, 39.0, 32.5, 26.7, 24.1, 22.5, 22.5, 13.4, 13.4

HRMS calcd. for C$_{29}$H$_{34}$O$_2$N$_3$, 456.2655. found, 456.2651.

HPLC t$_R$=12.39 min (Gradient (I), purity 100.0%).

<Synthesis of Phenylcyclopropylamine Derivatives of Examples 2 to 7>

Phenylcyclopropylamine derivatives of Examples 2 to 7 were synthesized in accordance with the following synthesis route.

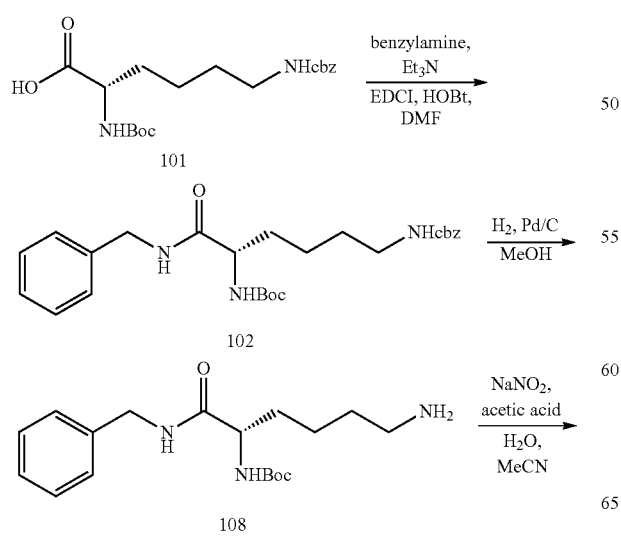

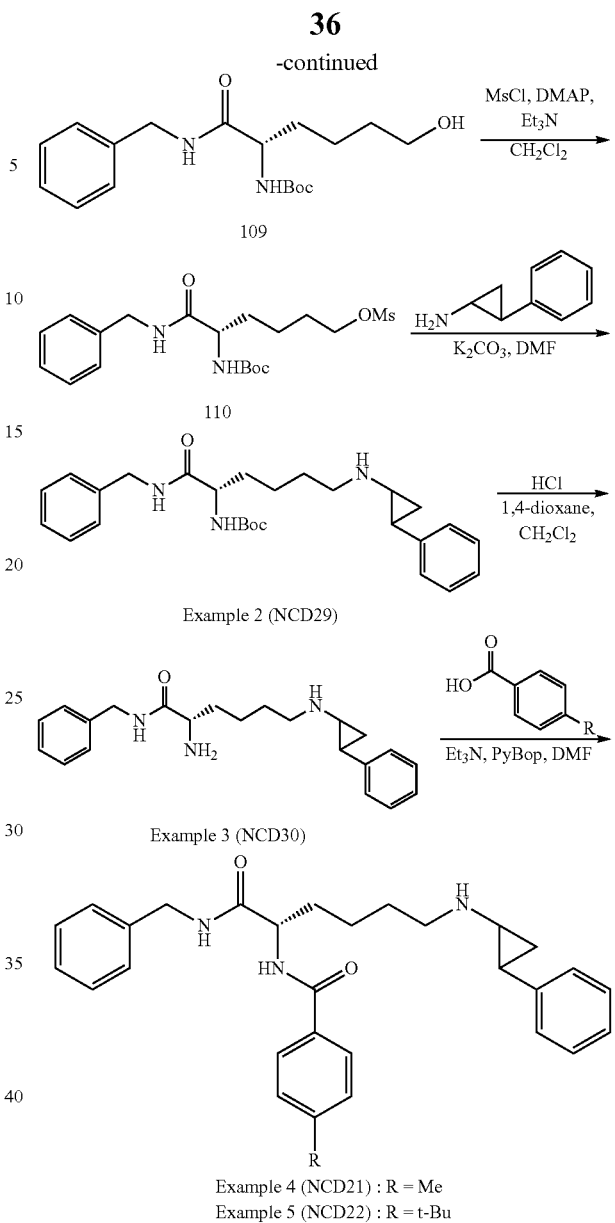

Step 2-1: Synthesis of 6-Amino-2-(N-tert-butoxycarbonyl) amino-N-benzylhexanamide (108)

6-(N-Benzyloxycarbonyl)amino-2-(N-tert-butoxycarbonyl)amino-N-benzylhexanamide (102) (10.0 g) obtained in Step 1-1 was dissolved in methanol (100 ml). To the solution was added a 5 wt % palladium-on-activated carbon catalyst (Pd/C) (4.05 g), and the mixture was stirred at room temperature for 13.5 hours under a hydrogen atmosphere. The reaction liquid was filtered through Celite. After that, the filtrate was concentrated to give a compound (108) (7.51 g, yield: quant) as a colorless amorphous solid. $^1$H NMR data on the compound (108) is shown below.

$^1$H-NMR (DMSO-d$_6$, 500 MHz, δ; ppm) 8.33-8.30 (1H, m), 7.30 (2H, t, J=7.49 Hz), 7.24-7.21 (3H, m), 6.88 (1H, d, J=7.49 Hz), 4.27 (2H, t, J=6.24 Hz), 3.92-3.88 (1H, m), 2.90-2.87 (2H, m), 1.60-1.46 (2H, m), 1.39 (9H, s), 1.36-1.18 (4H, m).

Step 2-2: Synthesis of 2-(N-tert-Butoxycarbonyl) amino-6-hydroxy-N-benzylhexanamide (109)

6-Amino-2-(N-tert-butoxycarbonyl)amino-N-benzylhexanamide (108) (7.52 g) obtained in Step 2-1 was neutralized with a solution of 4 N hydrochloric acid in 1,4-dioxane and then dissolved in water (600 ml). To the solution were added sodium nitrite (34.4 g) and acetic acid (6.91 g) under cooling with ice, and the mixture was stirred for 1.5 hours under cooling with ice. After 1.5 hours, the reaction liquid was warmed to room temperature and stirred for 3.5 hours. The reaction liquid was concentrated and extracted with ethyl acetate (300 ml). The organic layer was washed with brine (300 ml), dried over anhydrous sodium sulfate, and filtered. After that, the filtrate was concentrated and the residue was purified by silica gel flash column chromatography (developing solvent: n-hexane:ethyl acetate=2:1 to n-hexane:ethyl acetate=1:6) to give a compound (109) (2.31 g, yield: 31%) as a yellow amorphous solid. $^1$H NMR data on the compound (109) is shown below.

$^1$H-NMR (DMSO-$d_6$, 500 MHz, δ; ppm) 8.32-8.29 (1H, m), 7.29 (2H, t, J=7.49 Hz), 7.24-7.21 (3H, m), 6.85 (1H, d, J=7.99 Hz), 4.36 (1H, s), 4.27 (2H, t, J=5.24 Hz), 3.93-3.88 (1H, m), 1.62-1.47 (2H, m), 1.39 (9H, s), 1.34-1.24 (4H, m).

Step 2-3: Synthesis of 2-(N-tert-Butoxycarbonyl) amino-6-(O-methanesulfonyl)-N-benzylhexanamide (110)

2-(N-tert-Butoxycarbonyl)amino-6-hydroxy-N-benzylhexanamide (109) (1.89 g) obtained in Step 2-2 was dissolved in dichloromethane (45 ml). To the solution were added methanesulfonyl chloride (970 mg), dimethylaminopyridine (50.1 mg), and triethylamine (1.14 g) at −20° C., and the mixture was stirred at room temperature for 1.5 hours. The reaction liquid was diluted with dichloromethane (40 ml) and washed with an aqueous solution of 10% citric acid (100 ml) and brine (100 ml). The organic layer was dried over anhydrous sodium sulfate and filtered. After that, the filtrate was concentrated and the residue was purified by silica gel flash column chromatography (developing solvent: n-hexane:ethyl acetate=2:1 to n-hexane:ethyl acetate=1:2) to give a compound (110) (1.91 g, yield: 82%) as a white solid. $^1$H NMR data on the compound (110) is shown below.

$^1$H-NMR (DMSO-$d_6$, 500 MHz, δ; ppm) 8.34 (1H, t, J=5.99 Hz), 7.30 (2H, t, J=7.49 Hz), 7.25-7.21 (3H, m), 6.92 (1H, d, J=7.99 Hz), 4.28-4.27 (2H, m), 4.16 (2H, t, J=6.24 Hz), 3.95-3.90 (1H, m), 3.15 (3H, s), 1.66-1.52 (4H, m), 1.39 (9H, s), 1.38-1.32 (2H, m).

Step 2-4: Synthesis of 2-(N-tert-Butoxycarbonyl) amino-6-(trans-2-phenylcyclopropan-1-amino)-N-benzylhexanamide (Example 2, NCD29)

2-(N-tert-Butoxycarbonyl)amino-6-(O-methanesulfonyl)-N-benzylhexanamide (110) (1.49 g) obtained in Step 2-3 was dissolved in N,N-dimethylformamide (2.0 ml). To the solution were added trans-2-phenylcyclopropylamine (2.62 g) and potassium carbonate (2.54 g), and the mixture was stirred at 40° C. for 21.5 hours. The reaction liquid was diluted with dichloromethane (40 ml), washed with saturated aqueous sodium bicarbonate (100 ml) and brine (100 ml), dried over anhydrous sodium sulfate, and filtered. After that, the filtrate was concentrated and the residue was purified by silica gel flash column chromatography (developing solvent: chloroform to chloroform:methanol=50:1) to give a compound (Example 2, NCD29) (1.36 g, yield: 83%) as a yellow amorphous solid. $^1$H NMR data on the compound (Example 2, NCD29) is shown below.

$^1$H-NMR (DMSO-$d_6$, 500 MHz, δ; ppm) 8.30 (1H, t, J=5.49 Hz), 7.30-7.20 (7H, m), 7.10 (1H, t, J=7.24 Hz), 7.02 (2H, d, J=7.49 Hz), 6.86 (1H, d, J=7.49 Hz), 4.31-4.22 (2H, m), 3.92-3.87 (1H, m), 2.54 (2H, t, J=6.24 Hz), 2.18 (1H, s), 1.76 (1H, s), 1.61-1.48 (2H, m), 1.38 (9H, s), 1.31-1.23 (4H, m), 0.95-0.88 (2H, m).

Step 2-5: Synthesis of 2-Amino-6-(trans-2-phenylcyclopropan-1-amino)-N-benzylhexanamide Dihydrochloride (Example 3, NCD30)

2-(N-tert-Butoxycarbonyl)amino-6-(trans-2-phenylcyclopropan-1-amino)-N-benzylhexanamide (Example 2, NCD29) (1.36 g) obtained in Step 2-4 was dissolved in dichloromethane (30 ml). To the solution was added a solution of 4 N hydrochloric acid in 1,4-dioxane (7.5 ml) under cooling with ice, and the mixture was stirred at room temperature for 30 minutes. The reaction liquid was concentrated to give a compound (Example 3, NCD30) (1.43 g, yield: quant) as a yellow amorphous solid. $^1$H NMR data on the compound (Example 3, NCD30) is shown below.

$^1$H-NMR (DMSO-$d_6$, 500 MHz, δ; ppm) 9.57 (2H, s), 9.10 (1H, t, J=5.74 Hz), 8.30 (3H, s), 7.36-7.21 (8H, m), 7.18 (2H, d, J=6.99 Hz), 4.38 (2H, t, J=5.49 Hz), 3.82 (1H, s), 2.98-2.91 (3H, m), 2.58-2.54 (1H, m), 1.78 (2H, q, J=7.65 Hz), 1.68 (2H, quin, J=7.74 Hz), 1.60-1.58 (1H, m), 1.40-1.32 (2H, m), 1.26 (1H, q, J=6.98 Hz).

Step 2-6: Synthesis of 2-[N-(4-Methylbenzenecarbonyl)]amino-6-(trans-2-phenylcyclopropan-1-amino)-N-benzylhexanamide Trifluoroacetate (Example 4, NCD21)

2-Amino-6-(trans-2-phenylcyclopropan-1-amino)-N-benzylhexanamide dihydrochloride (Example 3, NCD30) (105 mg) obtained in Step 2-5 was dissolved in N,N-dimethylformamide (2.0 ml). To the solution were added PyBOP (163 mg), triethylamine (54.0 mg), and 4-methylbenzoic acid (38.7 mg), and the mixture was stirred at room temperature for 2.5 hours. The reaction liquid was diluted with dichloromethane (20 ml), washed with saturated aqueous sodium bicarbonate (60 ml) and brine (60 ml), dried over anhydrous sodium sulfate, and filtered. After that, the filtrate was concentrated and the residue was purified by silica gel flash column chromatography (developing solvent: chloroform to chloroform:methanol=40:1) to give a yellow amorphous solid (59.5 mg, yield: 47%). The resultant amorphous solid was purified by HPLC (Gradient (I)) to give a compound (Example 4, NCD21) as a colorless amorphous solid. $^1$H NMR, $^{13}$C NMR, MS (FAB), and purity data on the compound (Example 4, NCD21) are shown below.

$^1$H-NMR (DMSO-$d_6$, 600 MHz, δ; ppm) 8.81-8.77 (2H, m), 8.46 (1H, t, J=5.70 Hz), 8.39 (1H, d, J=7.80 Hz), 7.81 (2H, d, J=7.80 Hz), 7.31-7.16 (10H, m), 7.17 (2H, d, J=7.20 Hz), 4.49-4.46 (1H, m), 4.29 (2H, d, J=6.00 Hz), 3.06 (2H, s), 2.96 (1H, s), 2.41-2.38 (1H, m), 2.36 (3H, s), 1.85-1.76 (2H, m), 1.65-1.61 (2H, m), 1.47-1.36 (3H, m), 1.28 (1H, q, J=6.60 Hz)

$^{13}$C-NMR (DMSO-$d_6$ 600 MHz, δ; ppm) 171.7, 166.3, 157.8, 141.1, 139.3, 138.5, 131.2, 128.6, 128.3, 128.1, 127.5, 126.9, 126.6, 126.4, 126.2, 53.1, 47.1, 41.9, 31.0, 25.0, 22.8, 20.9, 20.5, 12.5

HRMS calcd. for $C_{30}H_{36}O_2N_3$ (MH—$CF_3COO^-$), 470.2808. found, 470.2812.

HPLC $t_R$=19.24 min (Gradient (II), purity 96.7%).

Step 3-1: Synthesis of 2-[N-(4-tert-Butylbenzenecarbonyl)]amino-6-(trans-2-phenylcyclopropan-1-amino)-N-benzylhexanamide Hydrochloride (Example 5, NCD22)

2-Amino-6-(trans-2-phenylcyclopropan-1-amino)-N-benzylhexanamide dihydrochloride (Example 3, NCD30) (96.6 mg) obtained in Step 2-5 was dissolved in N,N-dimethylformamide (2.0 ml). To the solution were added PyBOP (162 mg), triethylamine (52.3 mg), and 4-tert-butylbenzoic acid (51.1 mg), and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=50:1) to give a white solid. The resultant white solid was recrystallized from dichloromethane-diethyl ether to give a compound (Example 5, NCD22) (83.8 mg, yield: 71%) as a white solid. Melting point, $^1$H NMR, $^{13}$C NMR, MS (FAB), and elemental analysis data on the compound (Example 5, NCD22) are shown below.

Melting point: 101° C. to 103° C.

$^1$H-NMR (DMSO-$d_6$, 600 MHz, δ; ppm) 9.03 (2H, s), 8.48 (1H, t, J=6.00 Hz), 8.41 (1H, d, J=7.80 Hz), 7.87 (2H, d, J=8.40 Hz), 7.48 (2H, d, J=8.40 Hz), 7.32-7.28 (4H, m), 7.26-7.21 (4H, m), 7.17 (2H, d, J=7.20 Hz), 4.50-4.46 (1H, m), 4.29 (2H, d, J=6.00 Hz), 3.03-3.02 (2H, m), 2.93 (1H, s), 2.47-2.43 (1H, m), 1.85-1.75 (2H, m), 1.69-1.62 (2H, m), 1.49-1.33 (3H, m), 1.30 (9H, s), 1.28-1.24 (1H, m)

$^{13}$C-NMR (DMSO-$d_6$, 500 MHz, δ; ppm) 171.7, 166.2, 154.1, 139.4, 138.6, 131.2, 128.3, 128.1, 127.3, 126.9, 126.6, 126.4, 126.2, 124.8, 53.1, 47.0, 41.9, 37.3, 34.5, 30.9, 30.8, 25.0, 22.8, 20.5, 12.5

MS (FAB) m/z 512 (M–Cl$^-$)

Anal. Calcd. for $C_{33}H_{42}ClN_3O_2$.H2O: C, 70.01; H, 7.83; N, 7.42. Found: C, 69.80; H, 7.53; N, 7.64.

Step 4-1: Synthesis of 2-[N-(4-Chlorobenzenecarbonyl)]amino-6-(trans-2-phenylcyclopropan-1-amino)-N-benzylhexanamide Hydrochloride (Example 6, NCD23)

2-Amino-6-(trans-2-phenylcyclopropan-1-amino)-N-benzylhexanamide dihydrochloride (Example 3, NCD30) (99.1 mg) obtained in Step 2-5 was dissolved in N,N-dimethylformamide (2.0 ml). To the solution were added PyBOP (163 mg), triethylamine (52.7 mg), and 4-chlorobenzoic acid (45.7 mg), and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=80:1) to give a white solid. The resultant white solid was recrystallized from dichloromethane-diethyl ether to give a compound (Example 6, NCD23) (60.5 mg, yield: 49%) as a white solid. Melting point, $^1$H NMR, $^{13}$C NMR, MS (FAB), and elemental analysis data on the compound (Example 6, NCD23) are shown below.

Melting point: 107° C. to 109° C.

$^1$H-NMR (DMSO-$d_6$, 600 MHz, δ; ppm) 9.10 (2H, s), 8.62 (1H, d, J=7.80 Hz), 8.53 (1H, t, J=6.00 Hz), 7.95 (2H, d, J=8.40 Hz), 7.55 (2H, d, J=9.00 Hz), 7.32-7.29 (4H, m), 7.26-7.21 (4H, m), 7.17 (2H, d, J=7.80 Hz), 4.48-4.44 (1H, m), 4.29 (2H, d, J=6.00 Hz), 3.03 (2H, s), 2.93 (1H, s), 2.47-2.44 (1H, m), 1.83-1.77 (2H, m), 1.69-1.64 (2H, m), 1.50-1.36 (3H, m), 1.28-1.24 (1H, m);

$^{13}$C-NMR (DMSO-$d_6$, 500 MHz, δ; ppm) 171.6, 165.4, 139.3, 138.6, 136.0, 132.7, 129.5, 128.3, 128.1, 126.9, 126.6, 126.4, 126.2, 53.4, 47.0, 41.9, 37.2, 30.9, 30.6, 25.0, 22.8, 20.4, 12.5

MS (FAB) m/z 490 (M–Cl$^-$)

Anal. Calcd. for $C_{29}H_{33}ClN_3O_2$.H2O: C, 63.97; H, 6.48; N, 7.72. Found: C, 63.63; H, 6.35; N, 7.74.

Step 5-1: Synthesis of 2-[N-(4-Fluorobenzenecarbonyl)]amino-6-(trans-2-phenylcyclopropan-1-amino)-N-benzylhexanamide Hydrochloride (Example 7, NCD24)

2-Amino-6-(trans-2-phenylcyclopropan-1-amino)-N-benzylhexanamide dihydrochloride (Example 3, NCD30) (98.7 mg) obtained in Step 2-5 was dissolved in N,N-dimethylformamide (2.0 ml). To the solution were added PyBOP (162 mg), triethylamine (54.8 mg), and 4-fluorobenzoic acid (40.8 mg), and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=80:1) to give a white solid. The resultant white solid was recrystallized from dichloromethane-diethyl ether to give a compound (Example 7, NCD24) (67.3 mg, yield: 57%) as a white solid. Melting point, $^1$H NMR, $^{13}$C NMR, MS (FAB), and elemental analysis data on the compound (Example 7, NCD24) are shown below.

Melting point: 90° C. to 91° C.

$^1$H-NMR (DMSO-$d_6$, 600 MHz, δ; ppm) 9.05 (2H, s), 8.55 (1H, d, J=7.80 Hz), 8.52 (1H, t, J=6.00 Hz), 8.02-7.99 (2H, m), 7.32-7.29 (6H, m), 7.26-7.21 (4H, m), 7.17 (2H, d, J=7.20 Hz), 4.48-4.44 (1H, m), 4.29 (2H, d, J=6.60 Hz), 3.03 (2H, s), 2.93 (1H, s), 2.48-2.45 (1H, m), 1.85-1.74 (2H, m), 1.69-1.62 (2H, m), 1.49-1.36 (3H, m), 1.28-1.23 (1H, m)

$^{13}$C-NMR (DMSO-$d_6$, 500 MHz, δ; ppm) 171.6, 165.4, 164.8, 162.9, 139.4, 138.6, 130.5, 130.5, 130.2, 130.2, 128.3, 128.1, 126.9, 126.6, 126.4, 126.2, 115.0, 114.9, 53.3, 47.0, 41.9, 37.2, 30.9, 25.0, 22.8, 20.4, 12.5;

MS (FAB) m/z 474 (M–Cl$^-$)

Anal. Calcd. for $C_{29}H_{33}ClFN_3O_2$.6/5H2O: C, 65.51; H, 6.71; N, 7.90. Found: C, 65.48; H, 6.50; N, 7.98.

Step 6-1: Synthesis of 2-[N-(4-Phenylbenzenecarbonyl)]amino-6-(trans-2-phenylcyclopropan-1-amino)-N-benzylhexanamide Hydrochloride (Example 8, NCD25)

2-Amino-6-(trans-2-phenylcyclopropan-1-amino)-N-benzylhexanamide dihydrochloride (Example 3, NCD30) (101 mg) obtained in Step 2-5 was dissolved in N,N-dimethylformamide (2.0 ml). To the solution were added PyBOP (161 mg), triethylamine (56.9 mg), and 4-phenylbenzoic acid (58.3 mg), and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=80:1) to give a white solid. The resultant white solid was recrystallized from dichloromethane-diethyl ether to give a compound (Example 8, NCD25) (64.0 mg, yield: 51%) as a white solid. Melting point, $^1$H NMR, $^{13}$C NMR, MS (FAB), and elemental analysis data on the compound (Example 8, NCD25) are shown below.

Melting point: 143° C. to 146° C.

$^1$H-NMR (DMSO-d$_6$, 600 MHz, δ; ppm) 9.09 (2H, s), 8.57 (1H, d, J=7.80 Hz), 8.53 (1H, t, J=6.00 Hz), 8.03 (2H, d, J=7.80 Hz), 7.78 (2H, d, J=8.4 Hz), 7.73 (2H, d, J=7.20 Hz), 7.50 (2H, t, J=7.80 Hz), 7.42 (1H, t, J=7.20 Hz), 7.32-7.24 (6H, m), 7.23-7.20 (2H, m), 7.17 (2H, d, J=7.20 Hz), 4.52-4.49 (1H, m), 4.31 (2H, d, J=6.00 Hz), 3.04 (2H, s), 2.94 (1H, s), 2.49-2.46 (1H, m), 1.86-1.78 (2H, m), 1.70-1.64 (2H, m), 1.50-1.47 (3H, m), 1.28-1.25 (1H, m)

$^{13}$C-NMR (CD$_3$OD, 500 MHz, δ; ppm) 171.7, 166.1, 142.8, 139.4, 139.1, 138.7, 132.8, 128.9, 128.3, 128.2, 128.1, 128.0, 127.0, 126.8, 126.6, 126.4, 126.2, 53.3, 47.0, 41.9, 37.2, 30.9, 25.0, 22.9, 20.4, 12.5

MS (FAB) m/z 532 (M−Cl$^−$)

Anal. Calcd. for C$_{35}$H$_{38}$ClN$_3$O$_2$.H2O: C, 71.72; H, 6.88; N, 7.17. Found: C, 71.55; H, 6.64; N, 7.42.

Step 7-1: Synthesis of 2-[N-(4-Trifluoromethylbenzenecarbonyl)]amino-6-(trans-2-phenylcyclopropan-1-amino)-N-benzylhexanamide Hydrochloride (Example 9, NCD26)

2-Amino-6-(trans-2-phenylcyclopropan-1-amino)-N-benzylhexanamide dihydrochloride (Example 3, NCD30) (97.8 mg) obtained in Step 2-5 was dissolved in N,N-dimethylformamide (2.0 ml). To the solution were added PyBOP (165 mg), triethylamine (57.0 mg), and 4-trifluoromethylbenzoic acid (55.7 mg), and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=50:1) to give a white solid. The resultant white solid was recrystallized from dichloromethane-diethyl ether to give a compound (Example 9, NCD26) (66.7 mg, yield: 55%) as a white solid. Melting point, $^1$H NMR, $^{13}$C NMR, MS (FAB), and elemental analysis data on the compound (Example 9, NCD26) are shown below.

Melting point: 98° C. to 101° C.

$^1$H-NMR (DMSO-d$_6$, 600 MHz, δ; ppm) 9.10 (2H, s), 8.79 (1H, d, J=7.80 Hz), 8.56 (1H, t, J=6.00 Hz), 8.12 (2H, d, J=8.40 Hz), 7.86 (2H, d, J=8.40 Hz), 7.30 (4H, q, J=7.40 Hz), 7.26-7.21 (4H, m), 7.17 (2H, d, J=7.80 Hz), 4.51-4.47 (1H, m), 4.34-4.27 (2H, m), 3.04 (2H, s), 2.94 (1H, s), 2.46-2.44 (1H, m), 1.85-1.76 (2H, m), 1.69-1.62 (2H, m), 1.49-1.37 (3H, m), 1.28-1.25 (1H, m)

$^{13}$C-NMR (CD$_3$OD, 500 MHz, δ; ppm) 171.4, 165.3, 139.3, 138.7, 137.8, 131.2, 128.4, 128.3, 128.1, 126.9, 126.6, 126.4, 126.2, 125.1, 125.1, 125.1, 125.0, 53.5, 47.0, 41.9, 37.2, 30.8, 25.0, 22.8, 20.4, 12.5

MS (FAB) m/z 524 (M−Cl$^−$)

Anal. Calcd. for C$_{30}$H$_{33}$ClF$_3$N$_3$O$_2$.3/2H2O: C, 61.38; H, 6.18; N, 7.16. Found: C, 61.00; H, 5.83; N, 7.27.

<Synthesis of Phenylcyclopropylamine Derivative of Example 10>

A phenylcyclopropylamine derivative of Example 10 was synthesized in accordance with the following synthesis route.

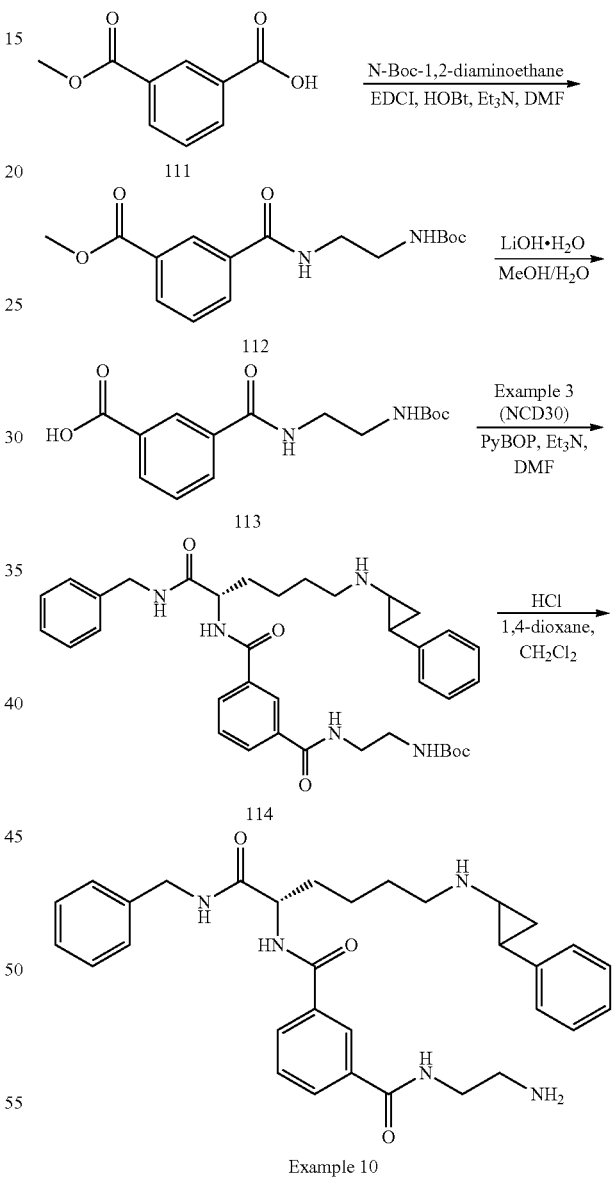

Step 8-1: Synthesis of Methyl-3-[(2-tert-butoxycarbonylamino)ethylcarbamoyl]benzoic Acid Ester (112)

Monomethylisophthalic acid (111) (1.01 g) was dissolved in N,N-dimethylformamide (25 ml). To the solution were added EDCI.HCl (1.60 g), HOBt.H$_2$O (1.26 g), triethylamine (848 mg), and N-tert-butoxycarbonyl-1,2-diaminoethane (1.00 g), and the mixture was stirred at room temperature for 16 hours. The reaction liquid was diluted with chloroform (100 ml), washed with water (300 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: n-hexane: ethyl acetate=17:50 to n-hexane:ethyl acetate=3:5) to give a compound (112) (1.47 g, yield: 81%) as a white solid. $^1$H NMR data on the compound (112) is shown below.

$^1$H-NMR (DMSO-$d_6$, 500 MHz, δ; ppm) 8.69-8.68 (1H, m), 8.43 (1H, s), 8.11-8.09 (2H, m), 7.63 (1H, t, J=7.74 Hz), 6.94-6.91 (1H, m), 3.89 (3H, s), 3.31-3.28 (2H, m), 3.12 (2H, q, J=5.82 Hz), 1.37 (9H, s).

Step 8-2: Synthesis of 3-[(2-tert-Butoxycarbonylamino)ethylcarbamoyl]benzoic acid (113)

Methyl-3-[(2-tert-butoxycarbonylamino)ethylcarbamoyl]benzoic acid ester (112) (447 mg) obtained in Step 8-1 was dissolved in methanol (18 ml) and water (5 ml). To the solution was added an aqueous solution of lithium hydroxide monohydrate (590 mg) (10 ml) under cooling with ice, and the mixture was stirred at room temperature for 5 hours. The reaction liquid was concentrated and the residue was dissolved in water (50 ml) and washed with dichloromethane. The aqueous layer was adjusted with citric acid to a pH of from about 2 to 3 and extracted with ethyl acetate. The organic layer was concentrated to give a compound (113) (438 mg, yield: quant) as a white solid. $^1$H NMR data on the compound (113) is shown below.

$^1$H-NMR (DMSO-$d_6$, 500 MHz, δ; ppm) 8.67-8.65 (1H, m), 8.42 (1H, s), 8.07 (2H, d, J=7.49 Hz), 7.59 (1H, t, J=7.49 Hz), 6.94-6.91 (1H, m), 3.31-3.28 (2H, m), 3.11 (2H, m), 1.37 (9H, s).

Step 8-3: Synthesis of 2-{3-[(2-tert-Butoxycarbonylamino)ethylcarbamoyl]benzenecarbonylamino}-6-(trans-2-phenylcyclopropan-1-amino)-N-benzylhexanamide Hydrochloride (114)

2-Amino-6-(trans-2-phenylcyclopropan-1-amino)-N-benzylhexanamide dihydrochloride (Example 3, NCD30) (102 mg) obtained in Step 2-5 was dissolved in N,N-dimethylformamide (2.0 ml). To the solution were added PyBOP (162 mg), triethylamine (53.6 mg), and 3-[(2-tert-butoxycarbonylamino)ethylcarbamoyl]benzoic acid (113) (86.6 mg) obtained in Step 8-2, and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=40:1) to give a compound (114) (84.1 mg, yield: 52%) as a white solid. $^1$H NMR data on the compound (114) is shown below.

$^1$H-NMR (DMSO-$d_6$, 500 MHz, δ; ppm) 8.99 (1H, s), 8.66-8.61 (2H, m), 8.55-8.54 (1H, m), 8.39 (1H, s), 8.05 (1H, d, J=6.99 Hz), 7.98 (2H, d, J=6.99 Hz), 7.56 (1H, t, J=7.49 Hz), 7.32-7.21 (8H, m), 7.16 (2H, d, J=6.99 Hz), 4.51-4.50 (1H, m), 4.31-4.29 (2H, m), 3.33-3.30 (2H, m), 3.12-3.11 (2H, m), 3.03 (2H, s), 2.93 (1H, m), 2.45-2.40 (1H, m), 1.84-1.78 (2H, m), 1.67-1.61 (2H, m), 1.50-1.42 (2H, m), 1.37 (10H, s), 1.27-1.23 (1H, m).

Step 8-4: Synthesis of 2-{3-[(2-Amino)ethylcarbamoyl]benzenecarbonylamino}-6-(trans-2-phenylcyclopropan-1-amino)-N-benzylhexanamide Ditrifluoroacetate (NCD27, Example 10)

2-{3-[(2-tert-Butoxycarbonylamino)ethylcarbamoyl]benzenecarbonylamino}-6-(trans-2-phenylcyclopropan-1-amino)-N-benzylhexanamide (114) (89.1 mg) obtained in Step 8-3 was dissolved in dichloromethane (2.0 ml). To the solution was added a solution of 4 N hydrochloric acid in ethyl acetate (0.46 ml) under cooling with ice, and the mixture was stirred at room temperature for 1 hour. The reaction liquid was concentrated and the resultant residue was purified by HPLC (Gradient (III)) to give a compound (Example 10, NCD27) (47.3 mg, yield: 51%) as a colorless amorphous solid. $^1$H NMR, $^{13}$C NMR, HRMS (FAB), and purity data on the compound (Example 10, NCD27) are shown below.

$^1$H-NMR (CD$_3$OD, 500 MHz, δ; ppm) 8.36 (1H, s), 8.05-8.02 (2H, m), 7.60 (1H, t, J=7.74 Hz), 7.31-7.28 (6H, m), 7.24-7.21 (2H, m), 7.16 (2H, d, J=6.99 Hz), 4.62-4.59 (1H, m), 4.41 (2H, d, J=4.49 Hz), 3.68 (2H, t, J=5.99 Hz), 3.18-3.14 (4H, m), 2.97-2.93 (1H, m), 2.45-2.41 (1H, m), 2.00-1.85 (2H, m), 1.77 (2H, s), 1.60-1.37 (4H, m)

$^{13}$C-NMR (DMSO-$d_6$, 500 MHz, δ; ppm) 171.6, 166.4, 165.9, 158.0, 157.8, 139.3, 138.5, 134.2, 134.1, 130.2, 129.9, 128.3, 128.1, 128.1, 127.0, 126.7, 126.6, 126.4, 126.2, 53.3, 47.1, 42.0, 38.5, 37.2, 37.1, 31.0, 25.0, 22.8, 20.5, 12.5.

HRMS calcd. for $C_{32}H_{40}O_3N_5$ (MH$^+$-2TFA), 542.3131. found, 542.3126 HPLC $t_R$=20.08 min (Gradient (III), purity 99.9%).

<Synthesis of Phenylcyclopropylamine Derivative of Example 11>

A phenylcyclopropylamine derivative of Example 11 was synthesized in accordance with the following synthesis route.

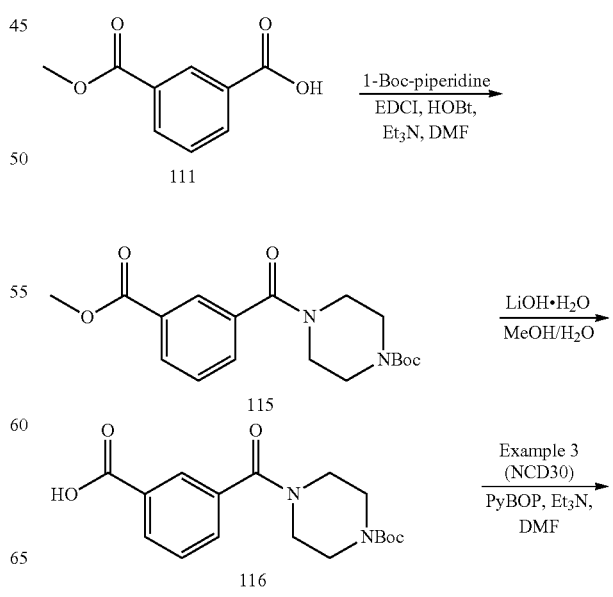

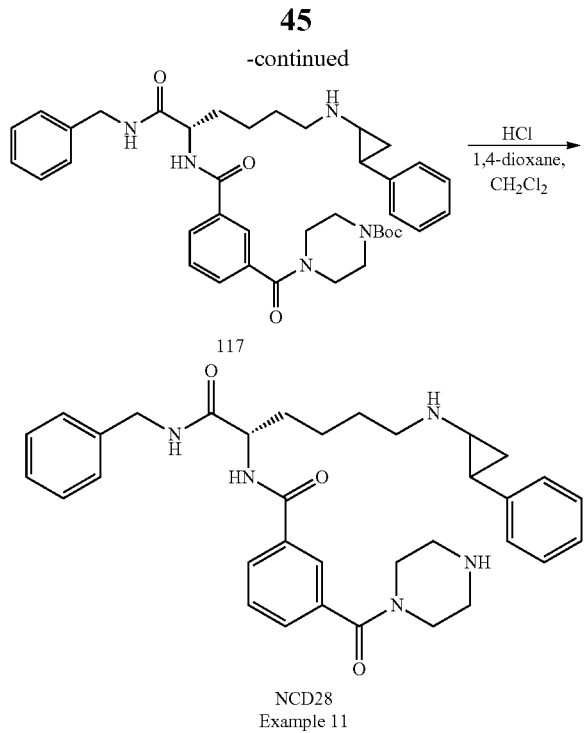

NCD28
Example 11

Step 9-1: Synthesis of Methyl-3-(4-tert-butoxycarbonylpiperazine-1-carbonyl)benzoic Acid Ester (115)

Monomethylisophthalic acid (111) (1.01 g) was dissolved in N,N-dimethylformamide (20 ml). To the solution were added EDCI.HCl (1.61 g), HOBt.H$_2$O (1.28 g), triethylamine (847 mg), and 4-tert-butoxycarbonylpiperazine (1.16 g), and the mixture was stirred at room temperature for 16 hours. The reaction liquid was diluted with chloroform (100 ml), washed with water (300 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: n-hexane:ethyl acetate=3:10 to n-hexane:ethyl acetate=3:5) to give a compound (115) (1.49 g, yield: 76%) as a white solid. $^1$H NMR data on the compound (115) is shown below.

$^1$H-NMR (CD$_3$OD, 500 MHz, δ; ppm) 8.12 (1H, d, J=7.99 Hz), 8.06 (1H, s), 7.67 (1H, d, J=7.49 Hz), 7.59 (1H, t, J=7.74 Hz), 3.92 (3H, s), 3.74 (2H, s), 3.54-3.41 (6H, m), 1.46 (9H, s).

Step 9-2: Synthesis of 3-(4-tert-Butoxycarbonylpiperazine-1-carbonylbenzoic acid (116)

Methyl-3-(4-tert-butoxycarbonylpiperazine-1-carbonyl) benzoic acid ester (115) (491 mg) obtained in Step 9-1 was dissolved in methanol (24 ml) and water (5 ml). To the solution was added an aqueous solution of lithium hydroxide monohydrate (594 mg) (10 ml) under cooling with ice, and the mixture was stirred at room temperature for 5 hours. The reaction liquid was concentrated and the residue was dissolved in water (50 ml) and washed with dichloromethane. The aqueous layer was adjusted with citric acid to a pH of from about 2 to 3 and extracted with ethyl acetate. The organic layer was concentrated to give a compound (116) (473 mg, yield: quant) as a colorless amorphous solid. $^1$H NMR data on the compound (116) is shown below.

$^1$H-NMR (CD$_3$OD, 500 MHz, δ; ppm) 8.13 (1H, d, J=7.49 Hz), 8.06 (1H, s), 7.66 (1H, d, J=7.49 Hz), 7.59 (1H, t, J=7.74 Hz), 3.74 (2H, s), 3.54-3.42 (6H, m), 1.46 (9H, s).

Step 9-3: Synthesis of 2-{3-[(4-tert-Butoxycarbonyl]piperazine-1-carbonyl]benzenecarbonylamino}-6-(trans-2-phenylcyclopropan-1-amino)-N-benzylhexanamide Hydrochloride (117)

2-Amino-6-(trans-2-phenylcyclopropan-1-amino)-N-benzylhexanamide dihydrochloride (Example 3, NCD30) (100 mg) obtained in Step 2-5 was dissolved in N,N-dimethylformamide (2.0 ml). To the solution were added PyBOP (164 mg), triethylamine (52.3 mg), and 3-(4-tert-butoxycarbonylpiperazine-1-carbonylbenzoic acid (118) (98.7 mg) obtained in Step 9-2, and the mixture was stirred at room temperature for 5 hours. The reaction liquid was diluted with dichloromethane (20 ml), washed with saturated aqueous sodium bicarbonate (60 ml) and brine (60 ml), dried over anhydrous sodium sulfate, filtered, and then neutralized with a solution of 4 N hydrochloric acid in ethyl acetate under cooling with ice. The neutralized solution was concentrated and the residue was purified by silica gel flash column chromatography (developing solvent: chloroform to chloroform:methanol=40:1) to give a compound (117) (82.9 mg, yield: 50%) as a white solid. $^1$H NMR data on the compound (117) is shown below.

$^1$H-NMR (DMSO-d$_6$, 500 MHz, δ; ppm) 9.08 (1H, s), 8.66 (1H, d, J=8.48 Hz), 8.55 (1H, t, J=5.74 Hz), 8.01 (1H, d, J=7.24 Hz), 7.97 (1H, s), 7.58-7.54 (2H, m), 7.31-7.22 (8H, m), 7.17 (2H, d, J=6.99 Hz), 4.51-4.46 (1H, m), 4.30 (2H, d, J=5.99 Hz), 3.62 (2H, s), 3.41-3.23 (6H, m), 3.03 (2H, s), 2.94 (1H, s), 2.48-2.43 (1H, m), 1.84-1.78 (2H, m), 1.68-1.62 (2H, m), 1.50-1.46 (3H, m), 1.41 (9H, s), 1.28-1.24 (1H, m).

Step 9-4: Synthesis of 2-[3-(Piperazine-1-carbonyl) benzenecarbonylamino}-6-(trans-2-phenylcyclopropan-1-amino)-N-benzylhexanamide Ditrifluoroacetate (Example 11, NCD28)

2-{3-[(4-tert-Butoxycarbonyl]piperazine-1-carbonyl]benzenecarbonylamino}-6-(trans-2-phenylcyclopropan-1-amino)-N-benzylhexanamide hydrochloride (117) (80.9 mg) obtained in Step 9-3 was dissolved in dichloromethane (2.0 ml). To the solution was added a solution of 4 N hydrochloric acid in ethyl acetate (0.66 ml) under cooling with ice, and the mixture was stirred at room temperature for 1 hour. The reaction liquid was concentrated and the resultant residue was purified by HPLC (Gradient (III)) to give a compound (Example 11, NCD28) (33.2 mg, yield: 35%) as a colorless amorphous solid. $^1$H NMR, $^{13}$C NMR, HRMS (FAB), and purity data on the compound (Example 11, NCD28) are shown below.

$^1$H-NMR (CD$_3$OD, 500 MHz, δ; ppm) 8.06 (1H, d, J=7.99 Hz), 8.00 (1H, s), 7.72 (1H, d, J=7.49 Hz), 7.66 (1H, t, J=7.74 Hz), 7.36-7.34 (6H, m), 7.29-7.26 (2H, m), 7.20 (2H, d, J=7.99 Hz), 4.66-4.63 (1H, m), 4.45 (2H, s, J=4.49 Hz), 3.99-3.65 (4H, s), 3.18-3.14 (2H, m), 2.95-2.93 (1H, m), 1.98-1.93 (1H, m), 1.89-1.83 (1H, m), 1.80-1.73 (2H, m), 1.55-1.45 (3H, m), 1.39-1.35 (1H, m)

$^{13}$C-NMR (CD$_3$OD, 500 MHz, δ; ppm) 174.0, 171.7, 169.2, 139.8, 139.2, 136.1, 135.9, 131.4, 130.5, 130.2, 129.8, 129.6, 128.5, 128.3, 128.1, 127.6, 127.4, 55.2, 49.8, 44.4, 44.1, 39.0, 32.5, 26.7, 24.2, 22.5, 13.4

HRMS calcd. for C$_{34}$H$_{42}$O$_3$N$_5$ (MH$^+$-2TFA), 568.3249. found, 568.3288 HPLC t$_R$=18.23 min (Gradient (VI), purity 99.9%).

<Synthesis of Phenylcyclopropylamine Derivatives of Examples 12 to 19>

Phenylcyclopropylamine derivatives of Examples 12 to 19 were synthesized in accordance with the following synthesis route.

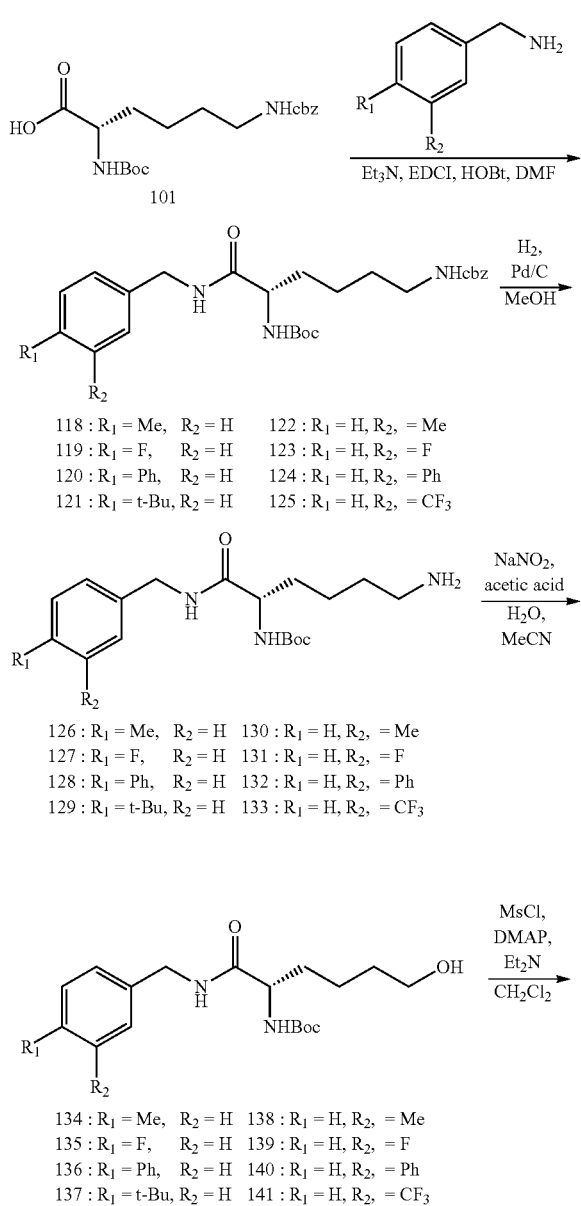

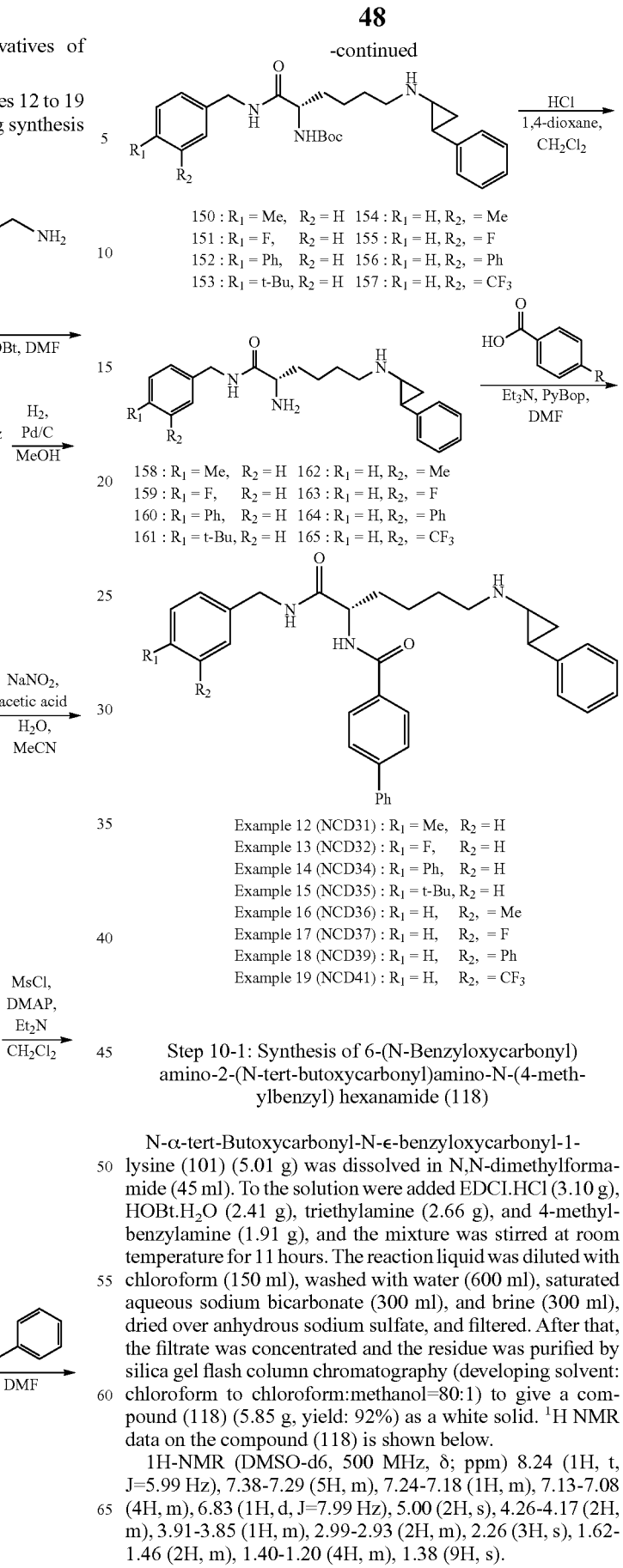

Example 12 (NCD31) : $R_1$ = Me, $R_2$ = H
Example 13 (NCD32) : $R_1$ = F, $R_2$ = H
Example 14 (NCD34) : $R_1$ = Ph, $R_2$ = H
Example 15 (NCD35) : $R_1$ = t-Bu, $R_2$ = H
Example 16 (NCD36) : $R_1$ = H, $R_2$, = Me
Example 17 (NCD37) : $R_1$ = H, $R_2$, = F
Example 18 (NCD39) : $R_1$ = H, $R_2$, = Ph
Example 19 (NCD41) : $R_1$ = H, $R_2$, = CF$_3$ Step 10-1: Synthesis of 6-(N-Benzyloxycarbonyl)amino-2-(N-tert-butoxycarbonyl)amino-N-(4-methylbenzyl) hexanamide (118)

N-α-tert-Butoxycarbonyl-N-ε-benzyloxycarbonyl-1-lysine (101) (5.01 g) was dissolved in N,N-dimethylformamide (45 ml). To the solution were added EDCl.HCl (3.10 g), HOBt.H$_2$O (2.41 g), triethylamine (2.66 g), and 4-methylbenzylamine (1.91 g), and the mixture was stirred at room temperature for 11 hours. The reaction liquid was diluted with chloroform (150 ml), washed with water (600 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: chloroform to chloroform:methanol=80:1) to give a compound (118) (5.85 g, yield: 92%) as a white solid. $^1$H NMR data on the compound (118) is shown below.

1H-NMR (DMSO-d6, 500 MHz, δ; ppm) 8.24 (1H, t, J=5.99 Hz), 7.38-7.29 (5H, m), 7.24-7.18 (1H, m), 7.13-7.08 (4H, m), 6.83 (1H, d, J=7.99 Hz), 5.00 (2H, s), 4.26-4.17 (2H, m), 3.91-3.85 (1H, m), 2.99-2.93 (2H, m), 2.26 (3H, s), 1.62-1.46 (2H, m), 1.40-1.20 (4H, m), 1.38 (9H, s).

Step 11-1: Synthesis of 6-(N-Benzyloxycarbonyl)amino-2-(N-tert-butoxycarbonyl)amino-N-(4-fluorobenzyl)hexanamide (119)

A compound (119) (6.08 g, yield: 95%) was obtained as a white solid by the same method as in Step 10-1 of Example 12 except for using 4-fluorobenzylamine (1.91 g) in place of 4-methylbenzylamine. $^1$H NMR data on the compound (119) is shown below.

$^1$H-NMR (DMSO-d6, 300 MHz, δ; ppm) 8.31 (1H, t, J=6.00 Hz), 7.40-7.20 (8H, m), 7.11 (2H, t, J=8.15 Hz), 6.85 (2H, d, J=7.50 Hz), 5.01 (2H, s), 4.25 (2H, d, J=6.00 Hz), 3.92-3.84 (1H, m), 3.00-2.93 (2H, m), 1.55-1.24 (6H, m), 1.38 (9H, s).

Step 12-1: Synthesis of 6-(N-Benzyloxycarbonyl)amino-2-(N-tert-butoxycarbonyl)amino-N-(4-phenylbenzyl)hexanamide (120)

A compound (120) (6.20 g, yield: 86%) was obtained as a white solid by the same method as in Step 10-1 of Example 12 except for using 4-phenylbenzylamine (2.90 g) in place of 4-methylbenzylamine. $^1$H NMR data on the compound (120) is shown below.

1H-NMR (DMSO-d6, 500 MHz, δ; ppm) 8.35 (1H, t, J=5.99 Hz), 7.64 (2H, d, J=6.99 Hz), 7.59 (2H, d, J=8.48 Hz), 7.45 (2H, t, J=7.49 Hz), 7.37-7.29 (8H, m), 7.26-7.23 (1H, m), 6.88 (1H, d, J=8.49 Hz), 5.00 (2H, s), 4.36-4.27 (2H, m), 3.93-3.89 (1H, m), 2.99-2.94 (2H, m), 1.64-1.47 (2H, m), 1.40-1.20 (4H, m), 1.39 (9H, s).

Step 13-1: Synthesis of 6-(N-Benzyloxycarbonyl)amino-2-(N-tert-butoxycarbonyl)amino-N-(4-tert-butylbenzyl)hexanamide (121)

A compound (121) (6.15 g, yield: 89%) was obtained as a white solid by the same method as in Step 10-1 of Example 12 except for using 4-tert-butylbenzylamine (2.57 g) in place of 4-methylbenzylamine. $^1$H NMR data on the compound (121) is shown below.

1H-NMR (DMSO-d6, 500 MHz, δ; ppm) 8.23 (1H, t, J=5.99 Hz), 7.38-7.30 (7H, m), 7.24-7.18 (1H, m), 7.16 (1H, d, J=7.99 Hz), 6.82 (1H, d, J=8.48 Hz), 5.00 (2H, s), 4.27-4.17 (2H, m), 3.91-3.85 (1H, m), 2.99-2.92 (2H, m), 1.62-1.46 (2H, m), 1.35-1.20 (4H, m), 1.38 (9H, s), 1.25 (9H, s).

Step 14-1: Synthesis of 6-(N-Benzyloxycarbonyl)amino-2-(N-tert-butoxycarbonyl)amino-N-(3-methylbenzyl)hexanamide (122)

A compound (122) (5.88 g, yield: 93%) was obtained as a white solid by the same method as in Step 10-1 of Example 12 except for using 3-methylbenzylamine (1.92 g) in place of 4-methylbenzylamine. $^1$H NMR data on the compound (122) is shown below.

1H-NMR (DMSO-d6, 500 MHz, δ; ppm) 8.26 (1H, t, J=5.74 Hz), 7.38-7.31 (5H, m), 7.24-7.22 (1H, m), 7.17 (1H, t, J=7.49 Hz), 7.05-7.01 (3H, m), 6.85 (1H, d, J=7.99 Hz), 5.00 (2H, s), 4.23 (2H, d, J=5.99 Hz), 3.94-3.83 (1H, m), 2.98-2.93 (2H, m), 2.51 (3H, s), 1.62-1.46 (2H, m), 1.40-1.18 (4H, m), 1.38 (9H, s).

Step 15-1: Synthesis of 6-(N-Benzyloxycarbonyl)amino-2-(N-tert-butoxycarbonyl)amino-N-(3-fluorobenzyl)hexanamide (123)

A compound (123) (6.23 g, yield: 97%) was obtained as a white solid by the same method as in Step 10-1 of Example 12 except for using 3-fluorobenzylamine (1.99 g) in place of 4-methylbenzylamine. $^1$H NMR data on the compound (123) is shown below.

1H-NMR (DMSO-d6, 500 MHz, δ; ppm) 8.37 (1H, t, J=5.99 Hz), 7.38-7.29 (6H, m), 7.26-7.20 (1H, m), 7.08-7.02 (3H, m), 6.92 (1H, d, J=7.99 Hz), 5.00 (2H, s), 4.33-4.24 (2H, m), 3.90-3.84 (1H, m), 3.00-2.92 (2H, m), 1.62-1.46 (2H, m), 1.40-1.20 (4H, m), 1.38 (9H, s).

Step 16-1: Synthesis of 6-(N-Benzyloxycarbonyl)amino-2-(N-tert-butoxycarbonyl)amino-N-(3-phenylbenzyl)hexanamide (124)

A compound (124) (2.85 g, yield: 94%) was obtained as a white solid by the same method as in Step 10-1 of Example 12 except for using 3-phenylbenzylamine (1.00 g) in place of 4-methylbenzylamine. $^1$H NMR data on the compound (124) is shown below.

1H-NMR (DMSO-d6, 300 MHz, δ; ppm) 8.37 (1H, t, J=6.00 Hz), 7.66 (2H, d, J=7.50 Hz), 7.55-7.23 (12H, m), 6.90 (1H, d, J=7.80 Hz), 5.01 (2H, s), 4.36 (2H, t, J=4.95 Hz), 3.94-3.87 (1H, m), 2.99-2.93 (2H, m), 1.63-1.51 (2H, m), 1.37-1.21 (4H, m), 1.37 (9H, s).

Step 17-1: Synthesis of 6-(N-Benzyloxycarbonyl)amino-2-(N-tert-butoxycarbonyl)amino-N-(3-trifluoromethylfluorobenzyl)hexanamide (125)

A compound (125) (5.90 g, yield: 84%) was obtained as a white solid by the same method as in Step 10-1 of Example 12 except for using 3-trifluoromethylbenzylamine (2.76 g) in place of 4-methylbenzylamine. $^1$H NMR data on the compound (125) is shown below.

1H-NMR (DMSO-d6, 500 MHz, δ; ppm) 8.45 (1H, t, J=5.74 Hz), 7.60-7.54 (4H, m), 7.38-7.31 (5H, m), 7.26-7.22 (1H, m), 6.94 (1H, d, J=7.99 Hz), 5.00 (2H, s), 4.41-4.31 (2H, m), 3.90-3.86 (1H, m), 2.98-2.94 (2H, m), 1.60-1.46 (2H, m), 1.40-1.20 (4H, m), 1.38 (9H, s).

Step 10-2: Synthesis of 6-Amino-2-(N-tert-butoxycarbonyl)amino-N-(4-methylbenzyl)hexanamide (126)

6-(N-Benzyloxycarbonyl)amino-2-(N-tert-butoxycarbonyl)amino-N-(4-methylbenzyl)hexanamide (118) (5.85 g) obtained in Step 10-1 was dissolved in methanol (150 ml). To the solution was added a 5 wt % palladium-on-activated carbon catalyst (Pd/C) (1.86 g), and the mixture was stirred at room temperature for 6.5 hours under a hydrogen atmosphere. The reaction liquid was filtered through Celite. After that, the filtrate was concentrated to give a compound (126) (4.35 g, yield: quant) as a colorless amorphous solid. $^1$H NMR data on the compound (126) is shown below.

1H-NMR (DMSO-d6, 500 MHz, δ; ppm) 8.25 (1H, t, J=7.99 Hz), 7.12 (2H, d, J=8.48 Hz), 7.10 (2H, d, J=7.99 Hz), 6.85 (1H, d, J=7.99 Hz), 4.26-4.17 (2H, m), 3.92-3.85 (1H, m), 2.54-2.51 (2H, m), 2.27 (3H, s), 1.62-1.46 (2H, m), 1.46-1.20 (4H, m), 1.38 (9H, s).

Step 11-2: Synthesis of 6-Amino-2-(N-tert-butoxycarbonyl)amino-N-(4-fluorobenzyl)hexanamide (127)

A compound (127) (4.47 g, yield: quant) was obtained as a colorless amorphous solid by the same method as in Step 10-2 of Example 12 except for using 6-(N-benzyloxycarbonyl)amino-2-(N-tert-butoxycarbonyl)amino-N-(4-fluorobenzyl)

hexanamide (119) (6.08 g) obtained in Step 11-1 in place of 6-(N-benzyloxycarbonyl)amino-2-(N-tert-butoxycarbonyl)amino-N-(4-methylbenzyl)hexanamide (118). $^1$H NMR data on the compound (127) is shown below.

$^1$H-NMR (DMSO-d$_6$, 500 MHz, δ; ppm) 8.34 (1H, t, J=5.49 Hz), 7.27 (2H, t, J=6.49 Hz), 7.12 (2H, t, J=8.48 Hz), 6.88 (1H, d, J=7.99 Hz), 4.29-4.21 (2H, m), 3.92-3.85 (1H, m), 2.54-2.51 (2H, m), 1.62-1.46 (2H, m), 1.40-1.20 (4H, m), 1.38 (9H, s).

Step 12-2: Synthesis of 6-Amino-2-(N-tert-butoxycarbonyl)amino-N-(4-phenylbenzyl)hexanamide (128)

A compound (128) (6.20 g, yield: 86%) was obtained as a colorless amorphous solid by the same method as in Step 10-2 of Example 12 except for using 6-(N-benzyloxycarbonyl)amino-2-(N-tert-butoxycarbonyl)amino-N-(4-phenylbenzyl)hexanamide (120) (6.20 g) obtained in Step 12-1 in place of 6-(N-benzyloxycarbonyl)amino-2-(N-tert-butoxycarbonyl)amino-N-(4-methylbenzyl)hexanamide (118). $^1$H NMR data on the compound (128) is shown below.

$^1$H-NMR (DMSO-d$_6$, 300 MHz, δ; ppm) 8.36 (1H, t, J=5.85 Hz), 7.64 (2H, d, J=7.95 Hz), 7.60 (2H, d, J=8.40 Hz), 7.46 (2H, t, J=7.50 Hz), 7.38-7.32 (3H, m), 6.90 (1H, d, J=8.40 Hz), 4.39-4.25 (2H, m), 3.96-3.88 (1H, m), 2.90 (2H, s), 1.61-1.50 (2H, m), 1.40-1.20 (4H, m), 1.40 (9H, s).

Step 13-2: Synthesis of 6-Amino-2-(N-tert-butoxycarbonyl)amino-N-(4-tert-butylbenzyl)hexanamide (129)

A compound (129) (4.95 g, yield: quant) was obtained as a colorless amorphous solid by the same method as in Step 10-2 of Example 12 except for using 6-(N-benzyloxycarbonyl)amino-2-(N-tert-butoxycarbonyl)amino-N-(4-tert-butylbenzyl)hexanamide (121) (6.15 g) obtained in Step 13-1 in place of 6-(N-benzyloxycarbonyl)amino-2-(N-tert-butoxycarbonyl)amino-N-(4-methylbenzyl)hexanamide (118). $^1$H NMR data on the compound (129) is shown below.

$^1$H-NMR (DMSO-d$_6$, 500 MHz, δ; ppm) 8.24 (1H, t, J=6.24 Hz), 7.31 (2H, d, J=7.99 Hz), 7.16 (2H, d, J=7.49 Hz), 6.85 (1H, d, J=7.99 Hz), 4.27-4.18 (2H, m), 3.92-3.86 (1H, m), 2.57 (1H, t, J=6.99 Hz), 1.62-1.46 (1H, m), 1.35-1.20 (4H, m), 1.38 (9H, s), 1.25 (9H, s).

Step 14-2: Synthesis of 6-Amino-2-(N-tert-butoxycarbonyl)amino-N-(3-methylbenzyl)hexanamide (130)

A compound (130) (4.33 g, yield: quant) was obtained as a colorless amorphous solid by the same method as in Step 10-2 of Example 12 except for using 6-(N-benzyloxycarbonyl)amino-2-(N-tert-butoxycarbonyl)amino-N-(3-methylbenzyl)hexanamide (122) (5.88 g) obtained in Step 14-1 in place of 6-(N-benzyloxycarbonyl)amino-2-(N-tert-butoxycarbonyl)amino-N-(4-methylbenzyl)hexanamide (118). $^1$H NMR data on the compound (130) is shown below.

$^1$H-NMR (DMSO-d$_6$, 500 MHz, δ; ppm) 8.29-8.25 (1H, m), 7.17 (1H, t, J=7.49 Hz), 7.06-7.01 (3H, m), 6.87 (1H, d, J=7.99 Hz), 4.23 (2H, d, J=5.49 Hz), 3.92-3.86 (1H, m), 2.27 (3H, s), 1.62-1.46 (2H, m), 1.46-1.20 (4H, m), 1.38 (9H, s).

Step 15-2: Synthesis of 6-Amino-2-(N-tert-butoxycarbonyl)amino-N-(3-fluorobenzyl)hexanamide (131)

A compound (131) (4.02 g, yield: 89%) was obtained as a colorless amorphous solid by the same method as in Step 10-2 of Example 12 except for using 6-(N-benzyloxycarbonyl)amino-2-(N-tert-butoxycarbonyl)amino-N-(3-fluorobenzyl)hexanamide (123) (6.22 g) obtained in Step 15-1 in place of 6-(N-benzyloxycarbonyl)amino-2-(N-tert-butoxycarbonyl)amino-N-(4-methylbenzyl)hexanamide (118). $^1$H NMR data on the compound (131) is shown below.

$^1$H-NMR (DMSO-d$_6$, 500 MHz, δ; ppm) 8.39 (1H, t, J=5.74 Hz), 7.35-7.31 (1H, m), 7.09-7.02 (3H, m), 6.94 (1H, d, J=7.49 Hz), 4.33-4.24 (2H, m), 3.91-3.85 (1H, m), 1.62-1.46 (2H, m), 1.40-1.20 (4H, m), 1.39 (9H, s).

Step 16-2: Synthesis of 6-Amino-2-(N-tert-butoxycarbonyl)amino-N-(3-phenylbenzyl)hexanamide (132)

A compound (132) (2.21 g, yield: quant) was obtained as a colorless amorphous solid by the same method as in Step 10-2 of Example 12 except for using 6-(N-benzyloxycarbonyl)amino-2-(N-tert-butoxycarbonyl)amino-N-(3-phenylbenzyl)hexanamide (124) (2.85 g) obtained in Step 16-1 in place of 6-(N-benzyloxycarbonyl)amino-2-(N-tert-butoxycarbonyl)amino-N-(4-methylbenzyl)hexanamide (118). $^1$H NMR data on the compound (132) is shown below.

$^1$H-NMR (DMSO-d$_6$, 300 MHz, δ; ppm) 8.39 (1H, t, J=6.30 Hz), 7.48 (2H, d, J=7.20 Hz), 7.55-7.37 (6H, m), 7.24 (1H, d, J=7.50 Hz), 6.93 (1H, d, J=8.10 Hz), 4.36 (2H, t, J=5.70 Hz), 3.95-3.88 (1H, m), 1.63-1.47 (2H, m), 1.37-1.24 (4H, m), 1.37 (9H, s).

Step 17-2: Synthesis of 6-Amino-2-(N-tert-butoxycarbonyl)amino-N-(3-trifluoromethylbenzyl)hexanamide (133)

A compound (133) (4.29 g, yield: quant) was obtained as a colorless amorphous solid by the same method as in Step 10-2 of Example 12 except for using 6-(N-benzyloxycarbonyl)amino-2-(N-tert-butoxycarbonyl)amino-N-(3-trifluoromethylbenzyl)hexanamide (125) (5.90 g) obtained in Step 17-1 in place of 6-(N-benzyloxycarbonyl)amino-2-(N-tert-butoxycarbonyl)amino-N-(4-methylbenzyl)hexanamide (118). $^1$H NMR data on the compound (133) is shown below.

$^1$H-NMR (DMSO-d$_6$, 300 MHz, δ; ppm) 8.50 (1H, t, J=5.85 Hz), 7.64-7.57 (4H, m), 6.97 (1H, d, J=7.20 Hz), 5.00 (2H, s), 4.40 (2H, d, J=5.70 Hz), 3.97-3.89 (1H, m), 1.65-1.50 (2H, m), 1.40-1.30 (4H, m), 1.42 (9H, s).

Step 10-3: Synthesis of 2-(N-tert-Butoxycarbonyl)amino-6-hydroxy-N-(4-methylbenzyl)hexanamide (134)

6-Amino-2-(N-tert-butoxycarbonyl)amino-N-(4-methylbenzyl)hexanamide (126) (4.35 g) obtained in Step 10-2 was neutralized with a solution of 4 N hydrochloric acid in 1,4-dioxane and then dissolved in water (600 ml). To the solution were added sodium nitrite (18.93 g) and acetic acid (3.89 g) under cooling with ice, and the mixture was stirred for 1.5 hours under cooling with ice. After 1.5 hours, the reaction liquid was warmed to room temperature and stirred for 2.0 hours. The reaction liquid was concentrated and extracted with ethyl acetate (150 ml). The organic layer was washed with brine (200 ml), dried over anhydrous sodium sulfate, and filtered. After that, the filtrate was concentrated and the residue was purified by silica gel flash column chromatography (developing solvent: n-hexane:ethyl acetate=2:1 to n-hexane:ethyl acetate=1:6) to give a compound (134) (1.69 g, yield: 39%) as a yellow amorphous solid. $^1$H NMR data on the compound (134) is shown below.

1H-NMR (DMSO-d6, 500 MHz, δ; ppm) 8.24 (1H, t, J=5.99 Hz), 7.12 (2H, d, J=8.48 Hz), 7.10 (2H, d, J=7.99 Hz), 6.82 (1H, d, J=7.99 Hz), 4.36 (1H, t, J=6.49 Hz), 4.26-4.17 (2H, m), 3.91-3.86 (1H, m), 2.26 (3H, s), 1.62-1.47 (2H, m), 1.40-1.20 (4H, m), 1.38 (9H, s).

Step 11-3: Synthesis of 2-(N-tert-Butoxycarbonyl) amino-6-hydroxy-N-(4-fluorobenzyl)hexanamide (135)

A compound (135) (1.10 g, yield: 31%) was obtained as a yellow amorphous solid by the same method as in Step 10-3 of Example 12 except for using 6-amino-2-(N-tert-butoxycarbonyl)amino-N-(4-fluorobenzyl)hexanamide (127) (4.95 g) obtained in Step 11-2 in place of 6-amino-2-(N-tert-butoxycarbonyl)amino-N-(4-methylbenzyl)hexanamide (128). $^1$H NMR data on the compound (135) is shown below.

1H-NMR (DMSO-d6, 500 MHz, δ; ppm) 8.32 (1H, t, J=6.24 Hz), 7.29-7.26 (2H, m), 7.11 (2H, t, J=8.73 Hz), 6.86 (1H, d, J=7.99 Hz), 4.36 (1H, t, J=4.74 Hz), 4.24 (2H, d, J=5.99 Hz), 3.90-3.86 (1H, m), 1.62-1.46 (2H, m), 1.40-1.20 (4H, m), 1.38 (9H, s).

Step 12-3: Synthesis of 2-(N-tert-Butoxycarbonyl) amino-6-hydroxy-N-(4-phenylbenzyl)hexanamide (136)

A compound (136) (1.04 g, yield: 25%) was obtained as a yellow amorphous solid by the same method as in Step 10-3 of Example 12 except for using 6-amino-2-(N-tert-butoxycarbonyl)amino-N-(4-phenylbenzyl)hexanamide (128) (5.55 g) obtained in Step 12-2 in place of 6-amino-2-(N-tert-butoxycarbonyl) amino-N-(4-methylbenzyl) hexanamide (126). $^1$H NMR data on the compound (136) is shown below.

1H-NMR (DMSO-d6, 300 MHz, δ; ppm) 8.36 (1H, t, J=5.85 Hz), 7.65 (2H, d, J=7.20 Hz), 7.59 (2H, d, J=8.40 Hz), 7.46 (2H, t, J=7.35 Hz), 7.38-7.32 (3H, m), 6.89 (1H, d, J=8.13 Hz), 4.39-4.25 (2H, m), 3.96-3.89 (1H, m), 1.64-1.51 (2H, m), 1.40-1.20 (4H, m), 1.40 (9H, s).

Step 13-3: Synthesis of 2-(N-tert-Butoxycarbonyl) amino-6-hydroxy-N-(4-tert-butylbenzyl)hexanamide (137)

A compound (137) (1.12 g, yield: 29%) was obtained as a yellow amorphous solid by the same method as in Step 10-3 of Example 12 except for using 6-amino-2-(N-tert-butoxycarbonyl)amino-N-(4-tert-butylbenzyl)hexanamide (129) (4.95 g) obtained in Step 13-2 in place of 6-amino-2-(N-tert-butoxycarbonyl) amino-N-(4-methylbenzyl) hexanamide (126). $^1$H NMR data on the compound (137) is shown below.

1H-NMR (DMSO-d6, 500 MHz, δ; ppm) 8.23 (1H, t, J=5.74 Hz), 7.31 (2H, d, J=8.48 Hz), 7.16 (2H, d, J=7.99 Hz), 6.81 (1H, d, J=8.48 Hz), 4.36 (1H, s), 4.27-4.18 (2H, m), 3.92-3.88 (1H, m), 1.62-1.44 (2H, m), 1.35-1.20 (4H, m), 1.38 (9H, s), 1.26 (9H, s).

Step 14-3: Synthesis of 2-(N-tert-Butoxycarbonyl) amino-6-hydroxy-N-(3-methylbenzyl)hexanamide (138)

A compound (138) (897 mg, yield: 21%) was obtained as a yellow amorphous solid by the same method as in Step 10-3 of Example 12 except for using 6-amino-2-(N-tert-butoxycarbonyl)amino-N-(3-methylbenzyl)hexanamide (130) (4.33 g) obtained in Step 14-2 in place of 6-amino-2-(N-tert-butoxycarbonyl) amino-N-(4-methylbenzyl) hexanamide (126). $^1$H NMR data on the compound (138) is shown below.

1H-NMR (DMSO-d6, 500 MHz, δ; ppm) 8.26 (1H, t, J=5.99 Hz), 7.17 (1H, t, J=7.74 Hz), 7.10-7.01 (3H, m), 6.84 (1H, d, J=7.99 Hz), 4.35 (1H, t, J=4.99 Hz), 4.23 (2H, d, J=5.99 Hz), 3.92-3.86 (1H, m), 3.40-3.35 (2H, m), 2.27 (3H, s), 1.62-1.46 (2H, m), 1.40-1.20 (4H, m), 1.38 (9H, s).

Step 15-3: Synthesis of 2-(N-tert-Butoxycarbonyl) amino-6-hydroxy-N-(3-fluorobenzyl)hexanamide (139)

A compound (139) (1.25 g, yield: 35%) was obtained as a yellow amorphous solid by the same method as in Step 10-3 of Example 12 except for using 6-amino-2-(N-tert-butoxycarbonyl)amino-N-(3-fluorobenzyl)hexanamide (131) (4.02 g) obtained in Step 15-2 in place of 6-amino-2-(N-tert-butoxycarbonyl)amino-N-(4-methylbenzyl)hexanamide (126). $^1$H NMR data on the compound (139) is shown below.

1H-NMR (DMSO-d6, 300 MHz, δ; ppm) 8.39 (1H, t, J=6.00 Hz), 7.38-7.31 (1H, m), 7.11-7.03 (3H, m), 6.94 (1H, d, J=7.80 Hz), 4.38 (1H, t, J=5.10 Hz), 4.31-4.24 (2H, m), 3.94-3.87 (1H, m), 1.65-1.51 (2H, m), 1.40-1.20 (4H, m), 1.39 (9H, s).

Step 16-3: Synthesis of 2-(N-tert-Butoxycarbonyl) amino-6-hydroxy-N-(3-phenylbenzyl)hexanamide (140)

A compound (140) (692 mg, yield: 31%) was obtained as a yellow amorphous solid by the same method as in Step 10-3 of Example 12 except for using 6-amino-2-(N-tert-butoxycarbonyl)amino-N-(3-phenylbenzyl)hexanamide (132) (2.21 g) obtained in Step 16-2 in place of 6-amino-2-(N-tert-butoxycarbonyl)amino-N-(4-methylbenzyl)hexanamide (126). $^1$H NMR data on the compound (140) is shown below.

1H-NMR (DMSO-d6, 300 MHz, δ; ppm) 8.39 (1H, t, J=6.00 Hz), 7.66 (2H, d, J=7.20 Hz), 7.55-7.34 (6H, m), 7.24 (1H, d, J=7.50 Hz), 6.91 (1H, d, J=7.80 Hz), 4.39-4.34 (2H, m), 4.07-4.00 (1H, m), 3.95-3.88 (1H, m), 1.65-1.50 (2H, m), 1.40-1.27 (4H, m), 1.37 (9H, s).

Step 17-3: Synthesis of 2-(N-tert-Butoxycarbonyl) amino-6-hydroxy-N-(3-trifluoromethylbenzyl)hexanamide (141)

A compound (141) (885 mg, yield: 21%) was obtained as a yellow amorphous solid by the same method as in Step 10-3 of Example 12 except for using 6-amino-2-(N-tert-butoxycarbonyl)amino-N-(3-trifluoromethylbenzyl)hexanamide (133) (4.29 g) obtained in Step 17-2 in place of 6-amino-2-(N-tert-butoxycarbonyl)amino-N-(4-methylbenzyl)hexanamide (126). $^1$H NMR data on the compound (141) is shown below.

1H-NMR (DMSO-d6, 300 MHz, δ; ppm) 8.46 (1H, t, J=5.85 Hz), 7.61-7.53 (4H, m), 6.93 (1H, d, J=7.80 Hz), 4.44-4.30 (2H, m), 3.93-3.85 (1H, m), 1.65-1.50 (2H, m), 1.40-1.30 (4H, m), 1.42 (9H, s).

Step 10-4: Synthesis of 2-(N-tert-Butoxycarbonyl) amino-6-(O-methanesulfonyl)-N-(4-methylbenzyl) hexanamide (142)

2-(N-tert-Butoxycarbonyl)amino-6-hydroxy-N-(4-methylbenzyl)hexanamide (134) (1.69 g) obtained in Step 10-3 was dissolved in dichloromethane (28 ml). To the solution were added methanesulfonyl chloride (853 mg), dimethylaminopyridine (43.3 mg), and triethylamine (989 mg) at 0° C., and the mixture was stirred at room temperature for 1.0 hour. The reaction liquid was diluted with dichloromethane (30 ml) and washed with an aqueous solution of 10% citric acid (100 ml) and brine (100 ml). The organic layer was dried over anhydrous sodium sulfate and filtered. After that, the filtrate was concentrated and the residue was purified by silica gel flash column chromatography (developing solvent: n-hexane:ethyl acetate=60:40 to n-hexane:ethyl acetate=35: 65) to give a compound (142) (1.22 g, yield: 59%) as a white solid. $^1$H NMR data on the compound (142) is shown below.

1H-NMR (DMSO-d6, 500 MHz, δ; ppm) 8.27 (1H, t, J=5.74 Hz), 7.12 (2H, d, J=8.48 Hz), 7.10 (2H, d, J=8.48 Hz), 6.88 (1H, d, J=7.49 Hz), 4.26-4.19 (2H, m), 4.16 (2H, t, J=6.49 Hz), 3.94-3.89 (1H, m), 3.15 (3H, s), 2.27 (3H, s), 1.68-1.50 (4H, m), 1.40-1.30 (2H, m), 1.39 (9H, s).

Step 11-4: Synthesis of 2-(N-tert-Butoxycarbonyl) amino-6-(O-methanesulfonyl)-N-(4-fluorobenzyl) hexanamide (143)

A compound (143) (1.02 g, yield: 76%) was obtained as a white solid by the same method as in Step 10-4 of Example 12 except for using 2-(N-tert-butoxycarbonyl)amino-6-hydroxy-N-(4-fluorobenzyl)hexanamide (135) (1.10 g) obtained in Step 11-3 in place of 2-(N-tert-butoxycarbonyl) amino-6-hydroxy-N-(4-methylbenzyl)hexanamide (134). $^1$H NMR data on the compound (143) is shown below.

$^1$H-NMR (DMSO-d$_6$, 500 MHz, δ; ppm) 8.36 (1H, t, J=5.99 Hz), 7.29-7.26 (2H, m), 7.12 (2H, t, J=8.73 Hz), 6.92 (1H, d, J=8.48 Hz), 4.25 (1H, d, J=5.49 Hz), 4.16 (2H, t, J=6.49 Hz), 3.93-3.89 (1H, m), 3.15 (3H, s), 1.66-1.50 (4H, m), 1.40-1.30 (2H, m), 1.38 (9H, s).

Step 12-4: Synthesis of 2-(N-tert-Butoxycarbonyl) amino-6-(O-methanesulfonyl)-N-(4-phenylbenzyl) hexanamide (144)

A compound (144) (1.03 g, yield: 83%) was obtained as a white solid by the same method as in Step 10-4 of Example 12 except for using 2-(N-tert-butoxycarbonyl)amino-6-hydroxy-N-(4-phenylbenzyl)hexanamide (136) (1.04 g) obtained in Step 12-3 in place of 2-(N-tert-butoxycarbonyl) amino-6-hydroxy-N-(4-benzyl)hexanamide (134). $^1$H NMR data on the compound (144) is shown below.

$^1$H-NMR (DMSO-d$_6$, 300 MHz, δ; ppm) 8.39 (1H, t, J=5.85 Hz), 7.65 (2H, d, J=7.95 Hz), 7.60 (2H, d, J=8.10 Hz), 7.46 (2H, t, J=7.50 Hz), 7.38-7.33 (3H, m), 6.94 (1H, d, J=8.10 Hz), 4.32 (2H, d, J=5.70 Hz), 4.18 (2H, t, J=6.45 Hz), 3.98-3.91 (1H, m), 3.16 (3H, s), 1.68-1.54 (4H, m), 1.40-1.30 (2H, m), 1.40 (9H, s).

Step 13-4: Synthesis of 2-(N-tert-Butoxycarbonyl) amino-6-(O-methanesulfonyl)-N-(4-tert-butylbenzyl) hexanamide (145)

A compound (145) (875 mg, yield: 65%) was obtained as a white solid by the same method as in Step 10-4 of Example 12 except for using 2-(N-tert-butoxycarbonyl)amino-6-hydroxy-N-(4-tert-butylbenzyl)hexanamide (137) (1.12 g) obtained in Step 13-3 in place of 2-(N-tert-butoxycarbonyl) amino-6-hydroxy-N-(4-methylbenzyl)hexanamide (134). $^1$H NMR data on the compound (145) is shown below.

$^1$H-NMR (DMSO-d$_6$, 500 MHz, δ; ppm) 8.28-8.25 (1H, m), 7.32 (2H, d, J=7.99 Hz), 7.16 (2H, d, J=8.48 Hz), 6.88 (1H, d, J=8.48 Hz), 4.24-4.21 (2H, m), 4.16 (2H, t, J=6.49 Hz), 3.94-3.88 (1H, m), 3.15 (3H, s), 1.68-1.48 (4H, m), 1.35-1.20 (2H, m), 1.38 (9H, s), 1.26 (9H, s).

Step 14-4: Synthesis of 2-(N-tert-Butoxycarbonyl) amino-6-(O-methanesulfonyl)-N-(3-methylbenzyl) hexanamide (146)

A compound (146) (833 mg, yield: 76%) was obtained as a white solid by the same method as in Step 10-4 of Example 12 except for using 2-(N-tert-butoxycarbonyl)amino-6-hydroxy-N-(3-methylbenzyl)hexanamide (138) (897 mg) obtained in Step 14-3 in place of 2-(N-tert-butoxycarbonyl) amino-6-hydroxy-N-(4-methylbenzyl)hexanamide (134). $^1$H NMR data on the compound (146) is shown below.

$^1$H-NMR (DMSO-d$_6$, 500 MHz, δ; ppm) 8.29 (1H, t, J=5.99 Hz), 7.18 (1H, t, J=7.49 Hz), 7.06-7.02 (3H, m), 6.90 (1H, d, J=7.99 Hz), 4.24 (2H, d, J=5.99 Hz), 4.16 (2H, t, J=6.49 Hz), 3.95-3.90 (1H, m), 3.15 (3H, s), 2.27 (3H, s), 1.68-1.50 (4H, m), 1.40-1.30 (2H, m), 1.39 (9H, s).

Step 15-4: Synthesis of 2-(N-tert-Butoxycarbonyl) amino-6-(O-methanesulfonyl)-N-(3-fluorobenzyl) hexanamide (147)

A compound (147) (1.14 g, yield: 75%) was obtained as a white solid by the same method as in Step 10-4 of Example 12 except for using 2-(N-tert-butoxycarbonyl)amino-6-hydroxy-N-(3-fluorobenzyl)hexanamide (139) (1.25 g) obtained in Step 15-3 in place of 2-(N-tert-butoxycarbonyl) amino-6-hydroxy-N-(4-methylbenzyl)hexanamide (134). $^1$H NMR data on the compound (147) is shown below.

$^1$H-NMR (DMSO-d$_6$, 300 MHz, δ; ppm) 8.41 (1H, t, J=5.85 Hz), 7.38-7.31 (1H, m), 7.10-6.97 (4H, m), 4.37-4.22 (2H, m), 4.17 (2H, t, J=5.85 Hz), 3.96-3.88 (1H, m), 3.16 (3H, s), 1.69-1.52 (4H, m), 1.40-1.29 (2H, m), 1.39 (9H, s).

Step 16-4: Synthesis of 2-(N-tert-Butoxycarbonyl) amino-6-(O-methanesulfonyl)-N-(3-phenylbenzyl) hexanamide (148)

A compound (148) (632 mg, yield: 77%) was obtained as a white solid by the same method as in Step 10-4 of Example 12 except for using 2-(N-tert-butoxycarbonyl)amino-6-hydroxy-N-(3-phenylbenzyl)hexanamide (140) (692 mg) obtained in Step 16-3 in place of 2-(N-tert-butoxycarbonyl) amino-6-hydroxy-N-(4-methylbenzyl)hexanamide (134). $^1$H NMR data on the compound (148) is shown below.

$^1$H-NMR (DMSO-d$_6$, 300 MHz, δ; ppm) 8.42 (1H, t, J=5.85 Hz), 7.56 (2H, d, J=7.50 Hz), 7.56-7.34 (6H, m), 7.24 (1H, d, J=7.80 Hz), 6.98 (1H, d, J=8.10 Hz), 4.44-4.29 (2H, m), 4.16 (2H, t, J=6.30 Hz), 3.98-3.91 (1H, m), 3.15 (3H, s), 1.70-1.55 (4H, m), 1.40-1.27 (2H, m), 1.37 (9H, s).

Step 17-4: Synthesis of 2-(N-tert-Butoxycarbonyl) amino-6-(O-methanesulfonyl)-N-(3-trifluoromethylbenzyl)hexanamide (149)

A compound (149) (786 mg, yield: 74%) was obtained as a white solid by the same method as in Step 10-4 of Example 12 except for using 2-(N-tert-butoxycarbonyl)amino-6-hydroxy-N-(3-trifluoromethylbenzyl)hexanamide (141) (885 mg) obtained in Step 17-3 in place of 2-(N-tert-butoxycarbonyl)amino-6-hydroxy-N-(4-methylbenzyl)hexanamide (134). $^1$H NMR data on the compound (149) is shown below.

$^1$H-NMR (DMSO-d$_6$, 300 MHz, δ; ppm) 8.50 (1H, t, J=6.00 Hz), 7.61-7.55 (4H, m), 7.01 (1H, d, J=7.80 Hz), 4.45-4.30 (2H, m), 4.17 (2H, t, J=6.30 Hz), 3.95-3.87 (1H, m), 3.16 (3H, s), 1.67-1.54 (4H, m), 1.35-1.27 (2H, m), 1.39 (9H, s).

Step 10-5: Synthesis of 2-(N-tert-Butoxycarbonyl) amino-6-(trans-2-phenylcyclopropan-1-amino)-N-(4-methylbenzyl)hexanamide (150)

2-(N-tert-Butoxycarbonyl)amino-6-(O-methanesulfonyl)-N-(4-methylbenzyl)hexanamide (142) (152 mg) obtained in Step 10-4 was dissolved in N,N-dimethylformamide (0.8 ml). To the solution were added trans-2-phenylcyclopropylamine (232 mg) and potassium carbonate (125 mg), and the mixture was stirred at 40° C. for 18.5 hours. The reaction liquid was diluted with dichloromethane (20 ml), washed with saturated aqueous sodium bicarbonate (50 ml) and brine (50 ml), dried over anhydrous sodium sulfate, and filtered. After that, the filtrate was concentrated and the residue was purified by silica gel flash column chromatography (developing solvent: chloroform to chloroform:methanol=80:1) to give a compound (150) (119 mg, yield: 73%) as a yellow amorphous solid. $^1$H NMR data on the compound (150) is shown below.

$^1$H-NMR (DMSO-$d_6$, 300 MHz, δ; ppm) 8.25 (1H, t, J=5.85 Hz), 7.22 (2H, t, J=7.35 Hz), 7.14-7.01 (7H, m), 6.85 (1H, d, J=8.10 Hz), 4.30-4.15 (2H, m), 3.93-3.85 (1H, m), 2.26 (3H, s), 2.22-2.17 (1H, m), 1.79-1.73 (1H, m), 1.61-1.45 (2H, m), 1.39-1.23 (4H, m), 1.38 (9H, s), 0.96-0.90 (2H, m).

Step 11-5: Synthesis of 2-(N-tert-Butoxycarbonyl) amino-6-(trans-2-phenylcyclopropan-1-amino)-N-(4-fluorobenzyl)hexanamide (151)

A compound (151) (130 mg, yield: 79%) was obtained as a yellow amorphous solid by the same method as in Step 10-5 of Example 12 except for using 2-(N-tert-butoxycarbonyl) amino-6-(O-methanesulfonyl)-N-(4-fluorobenzyl)hexanamide (143) (152 mg) obtained in Step 11-4 in place of 2-(N-tert-butoxycarbonyl)amino-6-(O-methanesulfonyl)-N-(4-methylbenzyl)hexanamide (142). $^1$H NMR data on the compound (151) is shown below.

$^1$H-NMR (DMSO-$d_6$, 300 MHz, δ; ppm) 8.33 (1H, t, J=6.00 Hz), 7.30-7.20 (4H, m), 7.14-7.08 (3H, m), 7.04-7.01 (2H, m), 6.89 (1H, d, J=7.50 Hz), 4.25 (2H, d, J=4.80 Hz), 3.92-3.84 (1H, m), 2.22-2.16 (1H, m), 1.79-1.73 (1H, m), 1.60-1.47 (2H, m), 1.39-1.17 (4H, m), 1.38 (9H, s), 0.96-0.90 (2H, m).

Step 12-5: Synthesis of 2-(N-tert-Butoxycarbonyl) amino-6-(trans-2-phenylcyclopropan-1-amino)-N-(4-phenylbenzyl)hexanamide (152)

A compound (152) (107 mg, yield: 58%) was obtained as a yellow amorphous solid by the same method as in Step 10-5 of Example 12 except for using 2-(N-tert-butoxycarbonyl) amino-6-(O-methanesulfonyl)-N-(4-phenylbenzyl)hexanamide (144) (182 mg) obtained in Step 12-4 in place of 2-(N-tert-butoxycarbonyl)amino-6-(O-methanesulfonyl)-N-(4-methylbenzyl)hexanamide (142). $^1$H NMR data on the compound (152) is shown below.

$^1$H-NMR (DMSO-$d_6$, 300 MHz, δ; ppm) 8.39-8.35 (1H, m), 7.64 (2H, d, J=7.20 Hz), 7.59 (2H, d, J=8.10 Hz), 7.46 (2H, t, J=7.50 Hz), 7.38-7.32 (3H, m), 7.21 (2H, t, J=7.35 Hz), 7.09 (1H, t, J=7.20 Hz), 7.03-7.00 (2H, m), 6.91 (1H, d, J=7.80 Hz), 4.39-4.24 (2H, m), 3.97-3.88 (1H, m), 2.58-2.53 (2H, m), 2.21-2.15 (1H, m), 1.79-1.73 (1H, m), 1.65-1.47 (2H, m), 1.40-1.23 (4H, m), 1.39 (9H, s), 0.97-0.87 (2H, m).

Step 13-5: Synthesis of 2-(N-tert-Butoxycarbonyl) amino-6-(trans-2-phenylcyclopropan-1-amino)-N-(4-tert-butylbenzyl)hexanamide (153)

A compound (153) (99.1 mg, yield: 56%) was obtained as a yellow amorphous solid by the same method as in Step 10-5 of Example 10 except for using 2-(N-tert-butoxycarbonyl) amino-6-(O-methanesulfonyl)-N-(4-tert-butylbenzyl)hexanamide (145) (162 mg) obtained in Step 13-4 in place of 2-(N-tert-butoxycarbonyl)amino-6-(O-methanesulfonyl)-N-(4-methylbenzyl)hexanamide (142). $^1$H NMR data on the compound (153) is shown below.

$^1$H-NMR (DMSO-$d_6$, 300 MHz, δ; ppm) 8.24 (1H, t, J=6.00 Hz), 7.21 (2H, d, J=8.40 Hz), 7.24-7.10 (7H, m), 7.03 (2H, d, J=8.40 Hz), 6.85 (1H, d, J=7.80 Hz), 4.30-4.15 (2H, m), 3.93-3.86 (1H, m), 2.22-2.16 (1H, m), 1.80-1.73 (1H, m), 1.60-1.46 (2H, m), 1.37-1.23 (4H, m), 1.38 (9H, s), 1.25 (9H, s), 0.96-0.88 (2H, m).

Step 14-5: Synthesis of 2-(N-tert-Butoxycarbonyl) amino-6-(trans-2-phenylcyclopropan-1-amino)-N-(3-methylbenzyl)hexanamide (154)

A compound (154) (110 mg, yield: 68%) was obtained as a yellow amorphous solid by the same method as in Step 10-5 of Example 12 except for using 2-(N-tert-butoxycarbonyl) amino-6-(O-methanesulfonyl)-N-(3-methylbenzyl)hexanamide (146) (152 mg) obtained in Step 14-4 in place of 2-(N-tert-butoxycarbonyl)amino-6-(O-methanesulfonyl)-N-(4-methylbenzyl)hexanamide (142). $^1$H NMR data on the compound (154) is shown below.

$^1$H-NMR (DMSO-d6, 300 MHz, δ; ppm) 8.27 (1H, t, J=5.70 Hz), 7.38-7.01 (9H, m), 6.87 (1H, d, J=7.80 Hz), 4.23 (2H, d, J=6.00 Hz), 3.93-3.86 (1H, m), 2.27 (3H, s), 2.22-2.16 (1H, m), 1.79-1.72 (1H, m), 1.61-1.45 (2H, m), 1.37-1.18 (4H, m), 1.39 (9H, s), 0.97-0.87 (2H, m).

Step 15-5: Synthesis of 2-(N-tert-Butoxycarbonyl) amino-6-(trans-2-phenylcyclopropan-1-amino)-N-(3-fluorobenzyl)hexanamide (155)

A compound (155) (117 mg, yield: 71%) was obtained as a yellow amorphous solid by the same method as in Step 10-5 of Example 10 except for using 2-(N-tert-butoxycarbonyl) amino-6-(O-methanesulfonyl)-N-(3-fluorobenzyl)hexanamide (147) (152 mg) obtained in Step 15-4 in place of 2-(N-tert-butoxycarbonyl)amino-6-(O-methanesulfonyl)-N-(4-methylbenzyl)hexanamide (142). $^1$H NMR data on the compound (155) is shown below.

$^1$H-NMR (DMSO-$d_6$, 300 MHz, δ; ppm) 8.39 (1H, t, J=6.00 Hz), 7.36-7.29 (1H, m), 7.22 (2H, t, J=7.35 Hz), 7.31-7.01 (6H, m), 6.95 (1H, d, J=7.80 Hz), 4.29 (2H, d, J=5.70 Hz), 3.94-3.84 (1H, m), 2.21-2.16 (1H, m), 1.80-1.73 (1H, m), 1.61-1.48 (2H, m), 1.39-1.22 (4H, m), 1.39 (9H, s), 0.96-0.90 (2H, m).

Step 16-5: Synthesis of 2-(N-tert-Butoxycarbonyl) amino-6-(trans-2-phenylcyclopropan-1-amino)-N-(3-phenylbenzyl)hexanamide (156)

A compound (156) (128.2 mg, yield: 69%) was obtained as a yellow amorphous solid by the same method as in Step 10-5 of Example 12 except for using 2-(N-tert-butoxycarbonyl) amino-6-(O-methanesulfonyl)-N-(3-phenylbenzyl)hexanamide (148) (179 mg) obtained in Step 16-4 in place of 2-(N- tert-butoxycarbonyl)amino-6-(O-methanesulfonyl)-N-(4-methylbenzyl)hexanamide (142). $^1$H NMR data on the compound (156) is shown below.

$^1$H-NMR (DMSO-d$_6$, 300 MHz, δ; ppm) 8.40-8.35 (1H, m), 7.65 (2H, d, J=6.90 Hz), 7.55-7.08 (10H, m), 7.01 (2H, d, J=6.90 Hz), 6.91 (1H, d, J=8.10 Hz), 4.36 (2H, d, J=5.70 Hz), 3.96-3.88 (1H, m), 2.20-2.15 (1H, m), 1.79-1.72 (1H, m), 1.65-1.47 (2H, m), 1.40-1.23 (4H, m), 1.37 (9H, s), 0.95-0.88 (2H, m).

Step 17-5: Synthesis of 2-(N-tert-Butoxycarbonyl) amino-6-(trans-2-phenylcyclopropan-1-amino)-N-(3-trifluoromethylbenzyl)hexanamide (157)

A compound (157) (118 mg, yield: 65%) was obtained as a yellow amorphous solid by the same method as in Step 10-5 of Example 12 except for using 2-(N-tert-butoxycarbonyl)amino-6-(O-methanesulfonyl)-N-(3-trifluoromethylbenzyl)hexanamide (149) (167 mg) obtained in Step 17-4 in place of 2-(N-tert-butoxycarbonyl)amino-6-(O-methanesulfonyl)-N-(4-methylbenzyl)hexanamide (142). $^1$H NMR data on the compound (157) is shown below.

$^1$H-NMR (DMSO-d$_6$, 300 MHz, δ; ppm) 8.46 (1H, t, J=6.00 Hz), 7.60-7.52 (4H, m), 7.22 (2H, t, J=7.35 Hz), 7.13-7.01 (3H, m), 6.95 (1H, d, J=7.80 Hz), 4.36 (2H, d, J=5.70 Hz), 3.92-3.86 (1H, m), 2.22-2.16 (1H, m), 1.79-1.73 (1H, m), 1.61-1.49 (2H, m), 1.37-1.23 (4H, m), 1.38 (9H, s), 0.96-0.89 (2H, m).

Step 10-6: Synthesis of 2-Amino-6-(trans-2-phenyl-cyclopropan-1-amino)-N-(4-methylbenzyl)hexanamide Dihydrochloride (158)

2-(N-tert-Butoxycarbonyl)amino-6-(trans-2-phenylcyclopropan-1-amino)-N-(4-methylbenzyl)hexanamide (150) (119 mg) obtained in Step 10-5 was dissolved in dichloromethane (2.0 ml). To the solution was added a solution of 4 N hydrochloric acid in 1,4-dioxane (0.7 ml) under cooling with ice, and the mixture was stirred at room temperature for 1.0 hour. The reaction liquid was concentrated to give a compound (158) (1.43 g, yield: quant) as a yellow amorphous solid. $^1$H NMR data on the compound (158) is shown below.

$^1$H-NMR (DMSO-d$_6$, 300 MHz, δ; ppm) 9.54 (2H, s), 9.04 (1H, t, J=5.70 Hz), 8.28 (3H, s), 7.34-7.13 (9H, m), 4.30 (2H, d, J=5.70 Hz), 3.83-3.77 (1H, m), 2.98 (3H, s), 2.29 (9H, s), 1.81-1.54 (5H, m), 1.41-1.23 (3H, m).

Step 11-6: Synthesis of 2-Amino-6-(trans-2-phenyl-cyclopropan-1-amino)-N-(4-fluorobenzyl)hexanamide Dihydrochloride (159)

A compound (159) (113 mg, yield: quant) was obtained as a yellow amorphous solid by the same method as in Step 10-6 of Example 10 except for using 2-(N-tert-butoxycarbonyl)amino-6-(trans-2-phenylcyclopropan-1-amino)-N-(4-fluorobenzyl)hexanamide (151) (130 mg) obtained in Step 11-5 in place of 2-(N-tert-butoxycarbonyl)amino-6-(trans-2-phenylcyclopropan-1-amino)-N-(4-methylbenzyl)hexanamide (150). $^1$H NMR data on the compound (159) is shown below.

$^1$H-NMR (DMSO-d$_6$, 300 MHz, δ; ppm) 9.54 (2H, s), 9.13 (1H, t, J=5.85 Hz), 8.29 (3H, s), 7.37-7.15 (9H, m), 4.40-4.27 (2H, m), 3.85-3.78 (1H, m), 3.03-2.89 (3H, m), 1.83-1.54 (5H, m), 1.41-1.23 (3H, m).

Step 12-6: Synthesis of 2-Amino-6-(trans-2-phenyl-cyclopropan-1-amino)-N-(4-phenylbenzyl)hexanamide Dihydrochloride (160)

A compound (160) (100 mg, yield: quant) was obtained as a yellow amorphous solid by the same method as in Step 10-6 of Example 12 except for using 2-(N-tert-butoxycarbonyl)amino-6-(trans-2-phenylcyclopropan-1-amino)-N-(4-phenylbenzyl)hexanamide (152) (107 mg) obtained in Step 12-5 in place of 2-(N-tert-butoxycarbonyl)amino-6-(trans-2-phenylcyclopropan-1-amino)-N-(4-methylbenzyl)hexanamide (150). $^1$H NMR data on the compound (160) is shown below.

$^1$H-NMR (DMSO-d$_6$, 300 MHz, δ; ppm) 9.42 (2H, s), 9.10 (1H, t, J=5.85 Hz), 8.26 (3H, s), 7.65 (4H, d, J=8.10 Hz), 7.49-7.00 (10H, m), 4.45-4.33 (2H, m), 3.87-3.79 (1H, m), 3.04-2.90 (3H, m), 1.84-1.52 (5H, m), 1.46-1.22 (3H, m).

Step 13-6: Synthesis of 2-Amino-6-(trans-2-phenyl-cyclopropan-1-amino)-N-(4-tert-butylbenzyl)hexanamide Dihydrochloride (161)

A compound (161) (112 mg, yield: quant) was obtained as a yellow amorphous solid by the same method as in Step 10-6 of Example 12 except for using 2-(N-tert-butoxycarbonyl)amino-6-(trans-2-phenylcyclopropan-1-amino)-N-(4-tert-butylbenzyl)hexanamide (153) (99.1 mg) obtained in Step 13-5 in place of 2-(N-tert-butoxycarbonyl)amino-6-(trans-2-phenylcyclopropan-1-amino)-N-(4-methylbenzyl)hexanamide (150). $^1$H NMR data on the compound (161) is shown below.

$^1$H-NMR (DMSO-d$_6$, 300 MHz, δ; ppm) 9.52 (2H, s), 9.01 (1H, t, J=5.70 Hz), 8.27 (3H, s), 7.37-7.17 (9H, m), 4.37-4.24 (2H, m), 3.83-3.76 (1H, m), 3.05-2.89 (3H, m), 2.29 (9H, s), 1.79-1.54 (5H, m), 1.43-1.23 (3H, m), 1.26 (9H, s).

Step 14-6: Synthesis of 2-Amino-6-(trans-2-phenyl-cyclopropan-1-amino)-N-(3-methylbenzyl)hexanamide Dihydrochloride (162)

A compound (162) (107 mg, yield: quant) was obtained as a yellow amorphous solid by the same method as in Step 10-6 of Example 10 except for using 2-(N-tert-butoxycarbonyl)amino-6-(trans-2-phenylcyclopropan-1-amino)-N-(3-methylbenzyl)hexanamide (154) (110 mg) obtained in Step 14-5 in place of 2-(N-tert-butoxycarbonyl)amino-6-(trans-2-phenylcyclopropan-1-amino)-N-(4-methylbenzyl)hexanamide (150). $^1$H NMR data on the compound (162) is shown below.

$^1$H-NMR (DMSO-d$_6$, 300 MHz, δ; ppm) 9.36 (2H, s), 8.99 (1H, t, J=6.00 Hz), 8.23 (3H, s), 7.34-7.07 (9H, m), 4.31 (2H, t, J=5.85 Hz), 3.83-3.76 (1H, m), 2.98 (3H, s), 2.29 (9H, s), 1.78-1.52 (5H, m), 1.36-1.24 (3H, m).

Step 15-6: Synthesis of 2-Amino-6-(trans-2-phenyl-cyclopropan-1-amino)-N-(3-fluorobenzyl)hexanamide Dihydrochloride (163)

A compound (163) (111 mg, yield: quant) was obtained as a yellow amorphous solid by the same method as in Step 10-6 of Example 12 except for using 2-(N-tert-butoxycarbonyl)amino-6-(trans-2-phenylcyclopropan-1-amino)-N-(3-fluorobenzyl)hexanamide (155) (117 mg) obtained in Step 15-5 in place of 2-(N-tert-butoxycarbonyl)amino-6-(trans-2-phenylcyclopropan-1-amino)-N-(4-fluorobenzyl)hexanamide (150). $^1$H NMR data on the compound (163) is shown below.

¹H-NMR (DMSO-d₆, 300 MHz, δ; ppm) 9.54 (2H, s), 9.13 (1H, t, J=5.85 Hz), 8.29 (3H, s), 7.37-7.15 (9H, m), 4.40-4.27 (2H, m), 3.85-3.78 (1H, m), 3.03-2.89 (3H, m), 1.83-1.54 (5H, m), 1.41-1.23 (3H, m).

Step 16-6: Synthesis of 2-Amino-6-(trans-2-phenylcyclopropan-1-amino)-N-(3-phenylbenzyl)hexanamide Dihydrochloride (164)

A compound (164) (120 mg, yield: quant) was obtained as a yellow amorphous solid by the same method as in Step 10-6 of Example 12 except for using 2-(N-tert-butoxycarbonyl)amino-6-(trans-2-phenylcyclopropan-1-amino)-N-(3-phenylbenzyl)hexanamide (156) (128 mg) obtained in Step 16-5 in place of 2-(N-tert-butoxycarbonyl)amino-6-(trans-2-phenylcyclopropan-1-amino)-N-(4-fluorobenzyl)hexanamide (150). ¹H NMR data on the compound (164) is shown below.

¹H-NMR (DMSO-d₆, 300 MHz, δ; ppm) 9.51 (2H, s), 9.15 (1H, t, J=5.70 Hz), 8.29 (3H, s), 7.67-7.16 (14H, m), 4.50-4.37 (2H, m), 3.89-3.79 (1H, m), 3.03-2.88 (3H, m), 1.84-1.53 (5H, m), 1.44-1.22 (3H, m).

Step 17-6: Synthesis of 2-Amino-6-(trans-2-phenylcyclopropan-1-amino)-N-(3-trifluoromethylbenzyl)hexanamide Dihydrochloride (165)

A compound (165) (113 mg, yield: quant) was obtained as a yellow amorphous solid by the same method as in Step 10-6 of Example 12 except for using 2-(N-tert-butoxycarbonyl)amino-6-(trans-2-phenylcyclopropan-1-amino)-N-(3-trifluoromethylbenzyl)hexanamide (157) (118 mg) obtained in Step 17-5 in place of 2-(N-tert-butoxycarbonyl)amino-6-(trans-2-phenylcyclopropan-1-amino)-N-(4-fluorobenzyl)hexanamide (150). ¹H NMR data on the compound (165) is shown below.

¹H-NMR (DMSO-d₆, 300 MHz, δ; ppm) 9.47 (2H, s), 9.22 (1H, t, J=6.00 Hz), 8.28 (3H, s), 7.66-7.56 (4H, m), 7.34-7.17 (5H, m), 4.52-4.38 (2H, m), 3.89-3.82 (1H, m), 3.04-2.91 (3H, m), 1.83-1.53 (5H, m), 1.43-1.24 (3H, m).

Step 10-7: Synthesis of 2-[N-(4-Phenylbenzenecarbonyl)]amino-6-(trans-2-phenylcyclopropan-1-amino)-N-(4-methylbenzyl)hexanamide Hydrochloride (Example 12, NCD31)

2-Amino-6-(trans-2-phenylcyclopropan-1-amino)-N-(4-methylbenzyl)hexanamide dihydrochloride (158) (114 mg) obtained in Step 10-6 was dissolved in N,N-dimethylformamide (2.0 ml). To the solution were added PyBOP (174 mg), triethylamine (60.0 mg), and 4-phenylbenzoic acid (60.8 mg), and the mixture was stirred at room temperature for 14 hours. The reaction liquid was diluted with dichloromethane (20 ml), washed with saturated aqueous sodium bicarbonate (60 ml) and brine (60 ml), dried over anhydrous sodium sulfate, and filtered. After that, the filtrate was neutralized with a solution of 4 N hydrochloric acid in ethyl acetate under cooling with ice. The neutralized solution was concentrated and the residue was purified by silica gel flash column chromatography (developing solvent: chloroform to chloroform: methanol=97:3) to give a yellow amorphous solid (79.4 mg, yield: 52%). The resultant amorphous solid was recrystallized from dichloromethane-diethyl ether to give a compound (Example 12, NCD31) as a white solid. Melting point, ¹H NMR, ¹³C NMR, MS (FAB), and elemental analysis data on the compound (Example 12, NCD31) are shown below.

Melting point: 117° C. to 118° C.

¹H-NMR (CD₃OD, 300 MHz, δ; ppm) 7.96 (2H, d, J=8.40 Hz), 7.73 (2H, d, J=8.10 Hz), 7.66 (2H, d, J=8.10 Hz), 7.47 (2H, t, J=7.50 Hz), 7.41-7.10 (10H, m), 4.65-4.60 (1H, m), 4.37 (2H, s), 3.17 (2H, t, J=7.80 Hz), 2.99-2.92 (1H, m), 2.49-2.42 (1H, m), 2.29 (3H, s), 2.01-1.74 (4H, m), 1.61-1.45 (3H, m), 1.37 (1H, q, J=7.00 Hz)

¹³C-NMR (CD₃OD, 300 MHz, δ; ppm) 174.1, 170.1, 146.1, 141.2, 139.3, 138.1, 136.8, 133.8, 130.2, 130.1, 129.8, 129.2, 128.6, 128.2, 128.1, 127.5, 55.1, 44.0, 39.1, 32.6, 26.8, 24.2, 22.6, 21.6, 13.5

HRMS calcd. for $C_{36}H_{40}O_2N_3$ (MH—Cl⁻), 546.3121. found, 546.3117.

Anal. Calcd. for $C_{36}H_{40}ClO_2N_3 \cdot 5/7H_2O$: C, 72.66; H, 7.02; N, 7.06. Found: C, 72.53; H, 6.75; N, 7.08.

Step 11-7: Synthesis of 2-[N-(4-Phenylbenzenecarbonyl)]amino-6-(trans-2-phenylcyclopropan-1-amino)-N-(4-fluorobenzyl)hexanamide Hydrochloride (Example 13, NCD32)

A yellow amorphous solid (66.1 mg, yield: 40%) was obtained by the same method as in Step 10-7 of Example 12 except for using 2-amino-6-(trans-2-phenylcyclopropan-1-amino)-N-(4-fluorobenzyl)hexanamide dihydrochloride (159) (124 mg) obtained in Step 11-6 in place of 2-amino-6-(trans-2-phenylcyclopropan-1-amino)-N-(4-methylbenzyl)hexanamide dihydrochloride (158). The resultant amorphous solid was recrystallized from dichloromethane-diethyl ether to give a compound (Example 13, NCD32) as a white solid. Melting point, ¹H NMR, ¹³C NMR, MS (FAB), and elemental analysis data on the compound (Example 13, NCD32) are shown below.

Melting point: 95° C. to 96° C.

¹H-NMR (CD₃OD, 300 MHz, δ; ppm) 7.96 (2H, dd, J=8.40 Hz), 7.74 (2H, dt, J=8.40 Hz), 7.67 (2H, dt, J=7.20 Hz), 7.47 (2H, tt, J=7.50 Hz), 7.41-7.14 (8H, m), 7.03 (2H, tt, J=8.85 Hz), 4.64-4.59 (1H, m), 4.39 (2H, s), 3.16 (2H, t, J=7.65 Hz), 2.95-2.90 (1H, m), 2.46-2.39 (1H, m), 2.04-1.73 (4H, m), 1.63-1.42 (3H, m), 1.36 (1H, q, J=7.10 Hz)

¹³C-NMR (CD₃OD, 300 MHz, δ; ppm) 174.2, 170.1, 165.1, 161.9, 146.0, 141.2, 139.5, 136.0, 135.9, 133.8, 130.5, 130.4, 130.1, 129.8, 129.2, 128.1, 128.1, 127.4, 116.3, 116.0, 55.2, 43.4, 39.2, 32.5, 26.9, 24.2, 22.6, 13.6

HRMS calcd. for $C_{35}H_{37}ClFO_2N_3$ (MH—Cl⁻), 550.2870. found, 550.2875.

Anal. Calcd. for $C_{35}H_{37}ClFO_2N_3 \cdot 5/8H_2O$: C, 70.37; H, 6.45; N, 7.03. Found: C, 70.36; H, 6.14; N, 7.15.

Step 12-7: Synthesis of 2-[N-(4-Phenylbenzenecarbonyl)]amino-6-(trans-2-phenylcyclopropan-1-amino)-N-(4-phenylbenzyl)hexanamide Hydrochloride (Example 14, NCD34)

A yellow amorphous solid (105 mg, yield: 82%) was obtained by the same method as in Step 10-7 of Example 12 except for using 2-amino-6-(trans-2-phenylcyclopropan-1-amino)-N-(4-phenylbenzyl)hexanamide dihydrochloride (160) (100 mg) obtained in Step 12-6 in place of 2-amino-6-(trans-2-phenylcyclopropan-1-amino)-N-(4-methylbenzyl)hexanamide dihydrochloride (158). The resultant amorphous solid was recrystallized from dichloromethane-diethyl ether to give a compound (Example 14, NCD34) as a white solid. Melting point, ¹H NMR, ¹³C NMR, MS (FAB), and elemental analysis data on the compound (Example 14, NCD34) are shown below.

Melting point: 139° C. to 140° C.

¹H-NMR (CD₃OD, 300 MHz, δ; ppm) 7.97 (2H, d, J=7.80 Hz), 7.73 (2H, d, J=8.40 Hz), 7.66 (2H, dt, J=7.20 Hz), 7.57 (4H, tt, J=7.20 Hz), 7.49-7.13 (13H, m), 4.68-4.63 (1H, m), 4.46 (2H, s), 3.19-3.12 (2H, m), 2.95-2.90 (1H, m), 2.48-2.41 (1H, m), 2.03-1.75 (4H, m), 1.59-1.44 (3H, m), 1.35 (1H, q, J=7.00 Hz)

¹³C-NMR (CD₃OD, 300 MHz, δ; ppm) 174.2, 170.1, 146.1, 141.1, 141.5, 141.2, 139.3, 139.1, 133.8, 130.1, 129.9, 129.8, 129.3, 129.2, 128.4, 128.2, 127.9, 127.5, 55.2, 43.9, 39.1, 32.6, 26.8, 24.2, 22.6, 13.5

HRMS calcd. for $C_{41}H_{42}O_2N_3$ (MH—Cl⁻), 608.3277. found, 608.3279.

Anal. Calcd. for $C_{41}H_{42}ClO_2N_3 \cdot 4/5H_2O$: C, 74.76; H, 6.67; N, 6.38. Found: C, 74.54; H, 6.49; N, 6.63.

Step 13-7: Synthesis of 2-[N-(4-Phenylbenzenecarbonyl)]amino-6-(trans-2-phenylcyclopropan-1-amino)-N-(4-tert-butylbenzyl)hexanamide Trifluoroacetate (Example 15, NCD35)

A yellow amorphous solid (107 mg, yield: 66%) was obtained by the same method as in Step 10-7 of Example 12 except for using 2-amino-6-(trans-2-phenylcyclopropan-1-amino)-N-(4-tert-butylbenzyl)hexanamide dihydrochloride (161) (96.1 mg) obtained in Step 13-6 in place of 2-amino-6-(trans-2-phenylcyclopropan-1-amino)-N-(4-methylbenzyl)hexanamide dihydrochloride (158). The resultant amorphous solid was purified by HPLC (Gradient (IV)) to give a compound (Example 15, NCD35) as a colorless amorphous solid. ¹H NMR, ¹³C NMR, MS (FAB), and elemental analysis data on the compound (Example 15, NCD35) are shown below.

¹H-NMR (CD₃OD, 300 MHz, δ; ppm) 7.95 (2H, d, J=7.80 Hz), 7.73 (2H, dt, J=8.40 Hz), 7.66 (2H, dt, J=6.90 Hz), 7.47 (2H, tt, J=7.35 Hz), 7.41-7.14 (10H, m), 4.66-4.61 (1H, m), 4.38 (2H, s), 3.18 (2H, t, J=6.90 Hz), 2.98-2.92 (1H, m), 2.48-2.41 (1H, m), 2.02-1.74 (4H, m), 1.62-1.44 (3H, m), 1.37 (1H, q, J=7.00 Hz), 1.28 (9H, s)

¹³C-NMR (CD₃OD, 300 MHz, δ; ppm) 174.1, 170.1, 151.4, 146.1, 141.2, 139.3, 136.8, 133.8, 130.1, 129.8, 129.2, 128.4, 128.2, 128.1, 127.5, 126.5, 55.1, 43.9, 39.1, 35.3, 32.6, 31.8, 26.7, 24.2, 22.5, 13.5

HRMS calcd. for $C_{39}H_{46}O_2N_3$ (MH—CF₃COO⁻), 588.3590. found, 588.3586.

HPLC $t_R$=23.99 min (Gradient (V), purity 100%).

Step 14-7: Synthesis of 2-[N-(4-Phenylbenzenecarbonyl)]amino-6-(trans-2-phenylcyclopropan-1-amino)-N-(3-methylbenzyl)hexanamide Hydrochloride (Example 16, NCD36)

A yellow amorphous solid (106 mg, yield: 76%) was obtained by the same method as in Step 10-7 of Example 12 except for using 2-amino-6-(trans-2-phenylcyclopropan-1-amino)-N-(3-methylbenzyl)hexanamide dihydrochloride (162) (105 mg) obtained in Step 14-6 in place of 2-amino-6-(trans-2-phenylcyclopropan-1-amino)-N-(4-methylbenzyl)hexanamide dihydrochloride (158). The resultant amorphous solid was recrystallized from dichloromethane-diethyl ether to give a compound (Example 16, NCD36) as a white solid. Melting point, ¹H NMR, ¹³C NMR, MS (FAB), and elemental analysis data on the compound (Example 16, NCD36) are shown below.

Melting point: 101° C. to 103° C.

¹H-NMR (CD₃OD, 300 MHz, δ; ppm) 7.96 (2H, d, J=8.10 Hz), 7.73 (2H, d, J=8.40 Hz), 7.66 (2H, d, J=6.90 Hz), 7.47 (2H, tt, J=7.35 Hz), 7.41-7.03 (10H, m), 4.66-4.61 (1H, m), 4.38 (2H, s), 3.18 (2H, t, J=7.05 Hz), 2.97-2.92 (1H, m), 2.48-2.42 (1H, m), 2.29 (3H, s), 2.04-1.74 (4H, m), 1.61-1.44 (3H, m), 1.36 (1H, q, J=7.00 Hz)

¹³C-NMR (CD₃OD, 300 MHz, δ; ppm) 174.2, 170.0, 146.0, 141.2, 139.7, 139.3, 133.8, 130.1, 129.8, 129.5, 129.2, 128.9, 128.2, 128.1, 128.1, 127.5, 125.6, 55.2, 44.1, 39.1, 32.5, 26.7, 24.2, 22.5, 21.5, 13.5

HRMS calcd. for $C_{36}H_{40}O_2N_3$ (MH—Cl⁻), 546.3121. found, 546.3125.

Anal. Calcd. for $C_{36}H_{40}ClO_2N_3 \cdot H_2O$: C, 72.04; H, 7.05; N, 7.00. Found: C, 72.01; H, 6.94; N, 7.16.

Step 15-7: Synthesis of 2-[N-(4-Phenylbenzenecarbonyl)]amino-6-(trans-2-phenylcyclopropan-1-amino)-N-(3-fluorobenzyl)hexanamide Hydrochloride (Example 17, NCD37)

A yellow amorphous solid (78.8 mg, yield: 54%) was obtained by the same method as in Step 10-7 of Example 12 except for using 2-amino-6-(trans-2-phenylcyclopropan-1-amino)-N-(3-fluorobenzyl)hexanamide dihydrochloride (163) (111 mg) obtained in Step 15-6 in place of 2-amino-6-(trans-2-phenylcyclopropan-1-amino)-N-(4-methylbenzyl)hexanamide dihydrochloride (158). The resultant amorphous solid was purified by HPLC (Gradient (IV)) to give a compound (Example 17, NCD37) as a colorless amorphous solid. ¹H NMR, ¹³C NMR, MS (FAB), and purity data on the compound (Example 17, NCD37) are shown below.

¹H-NMR (CD₃OD, 300 MHz, δ; ppm) 7.96 (2H, d, J=8.10 Hz), 7.73 (2H, dt, J=8.40 Hz), 7.66 (2H, d, J=7.80 Hz), 7.47 (2H, tt, J=7.20 Hz), 7.41-6.93 (10H, m), 4.67-4.61 (1H, m), 4.44-4.42 (2H, m), 3.22-3.16 (2H, m), 2.99-2.92 (1H, m), 2.48-2.41 (1H, m), 2.07-1.72 (4H, m), 1.65-1.44 (3H, m), 1.37 (1H, q, J=7.10 Hz)

¹³C-NMR (CD₃OD, 300 MHz, δ; ppm) 174.3, 170.1, 166.0, 162.8, 146.0, 142.9, 142.8, 141.2, 139.3, 133.8, 131.4, 131.2, 130.1, 129.8, 129.2, 128.1, 128.1, 128.1, 127.4, 124.3, 124.2, 115.3, 115.0, 115.0, 114.7, 55.1, 43.6, 39.0, 32.4, 26.7, 24.2, 22.5, 13.4

HRMS calcd. for $C_{35}H_{37}FO_2N_3$ (MH—CF₃COO⁻), 550.2870. found, 550.2868.

HPLC $t_R$=13.35 min (Gradient (VI), purity 98.0%).

Step 16-7: Synthesis of 2-[N-(4-Phenylbenzenecarbonyl)]amino-6-(trans-2-phenylcyclopropan-1-amino)-N-(3-phenylbenzyl)hexanamide Hydrochloride (Example 18, NCD39)

A yellow amorphous solid (145 mg, yield: 94%) was obtained by the same method as in Step 10-7 of Example 12 except for using 2-amino-6-(trans-2-phenylcyclopropan-1-amino)-N-(3-phenylbenzyl)hexanamide dihydrochloride (164) (120 mg) obtained in Step 16-6 in place of 2-amino-6-(trans-2-phenylcyclopropan-1-amino)-N-(4-methylbenzyl)hexanamide dihydrochloride (158). The resultant amorphous solid was purified by HPLC (Gradient (IV)) to give a compound (Example 18, NCD39) as a colorless amorphous solid. ¹H NMR, ¹³C NMR, MS (FAB), and purity data on the compound (Example 18, NCD39) are shown below.

¹H-NMR (CD₃OD, 300 MHz, δ; ppm) 7.94 (2H, d, J=7.80 Hz), 7.70 (2H, d, J=7.80 Hz), 7.65 (2H, dt, J=6.90 Hz), 7.71-7.12 (17H, m), 4.67-4.62 (1H, m), 4.50-4.48 (2H, m), 3.16-3.11 (2H, m), 2.93-2.88 (1H, m), 2.46-2.39 (1H, m), 2.05-1.72 (4H, m), 1.63-1.42 (3H, m), 1.35 (1H, q, J=6.90 Hz)

¹³C-NMR (CD₃OD, 300 MHz, δ; ppm) 174.3, 170.0, 146.0, 142.8, 142.2, 142.2, 141.2, 140.5, 139.2, 133.7, 130.1, 129.9, 129.8, 129.2, 128.4, 128.1, 128.1, 128.1, 128.0, 127.5, 127.4, 127.0, 126.9, 55.2, 44.1, 39.0, 32.4, 26.7, 24.2, 22.5, 13.4

HRMS calcd. for $C_{41}H_{42}O_2N_3$ (MH—$CF_3COO^-$), 608.3277. found, 608.3273.

HPLC $t_R$=22.67 min (Gradient (V), purity 100%).

Step 17-7: Synthesis of 2-[N-(4-Phenylbenzenecarbonyl)]amino-6-(trans-2-phenylcyclopropan-1-amino)-N-(3-trifluoromethylbenzyl)hexanamide Hydrochloride (Example 19, NCD41)

A yellow amorphous solid (84 mg, yield: 60%) was obtained by the same method as in Step 10-7 of Example 12 except for using 2-amino-6-(trans-2-phenylcyclopropan-1-amino)-N-(3-trifluoromethylbenzyl)hexanamide dihydrochloride (165) (113 mg) obtained in Step 17-6 in place of 2-amino-6-(trans-2-phenylcyclopropan-1-amino)-N-(4-methylbenzyl)hexanamide dihydrochloride (158). The resultant amorphous solid was recrystallized from dichloromethane-diethyl ether to give a compound (Example 19, NCD41) as a pale yellow solid. Melting point, $^1$H NMR, $^{13}$C NMR, MS (FAB), and purity data on the compound (Example 19, NCD41) are shown below.

Melting point: 129° C. to 130° C.

$^1$H-NMR (CD$_3$OD, 300 MHz, δ; ppm) 7.96 (2H, d, J=7.80 Hz), 7.74 (2H, dt, J=8.40 Hz), 7.67 (2H, d, J=6.90 Hz), 7.59-7.15 (12H, m), 4.67-4.62 (1H, m), 4.50 (2H, s), 3.22-3.16 (2H, m), 2.98-2.93 (1H, m), 2.47-2.40 (1H, m), 2.03-1.73 (4H, m), 1.63-1.35 (4H, m)

$^{13}$C-NMR (CD$_3$OD, 300 MHz, δ; ppm) 174.5, 170.2, 146.1, 141.5, 141.3, 139.3, 135.6, 134.5, 133.8, 132.4, 132.1, 131.7, 131.3, 131.1, 130.4, 130.1, 129.8, 129.3, 129.2, 128.2, 128.1, 128.1, 127.5, 125.2, 125.2, 125.1, 125.0, 125.0, 55.3, 43.7, 39.1, 32.4, 28.2, 26.8, 24.3, 24.2, 22.5, 13.5

HRMS calcd. for $C_{36}H_{37}F_3O_2N_3$ (MH—Cl$^-$), 600.2838. found, 600.2834.

HPLC $t_R$=15.07 min (Gradient (VI), purity 95.2%).

<Synthesis of Phenylcyclopropylamine Derivatives of Examples 20 and 21>

Phenylcyclopropylamine derivatives of Examples 20 and 21 were synthesized in accordance with the following synthesis route.

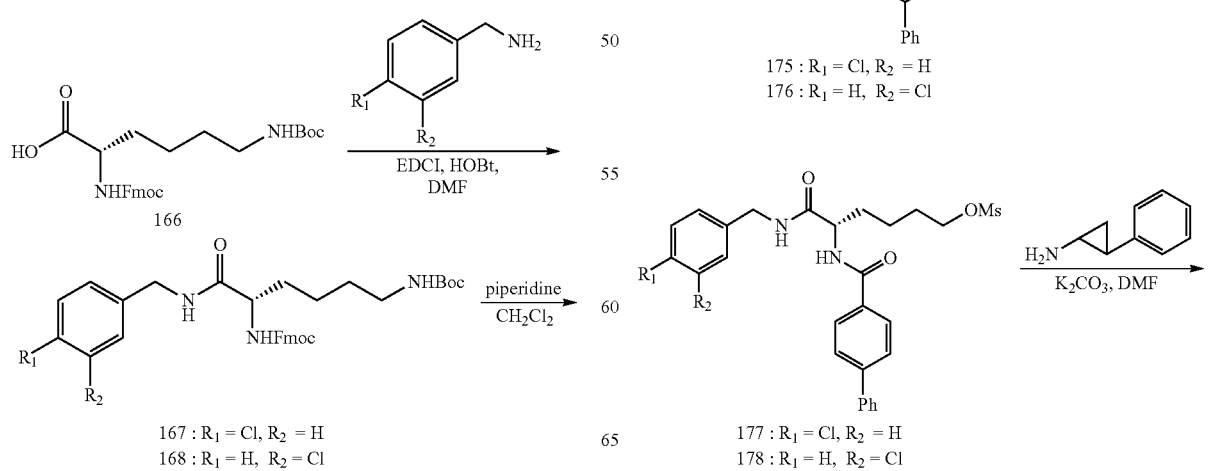

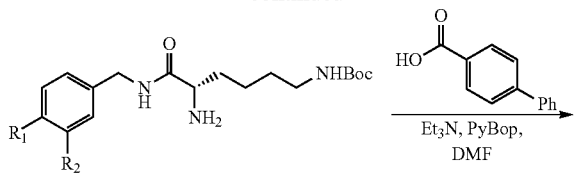

169 : R$_1$ = Cl, R$_2$ = H
170 : R$_1$ = H, R$_2$ = Cl

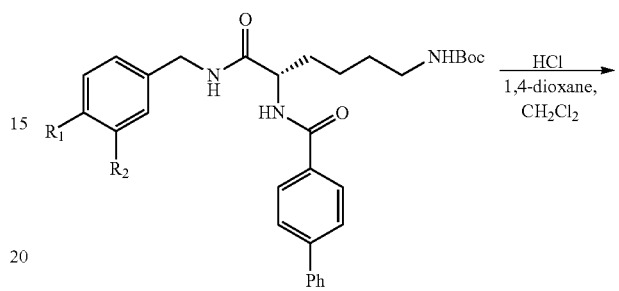

171 : R$_1$ = Cl, R$_2$ = H
172 : R$_1$ = H, R$_2$ = Cl

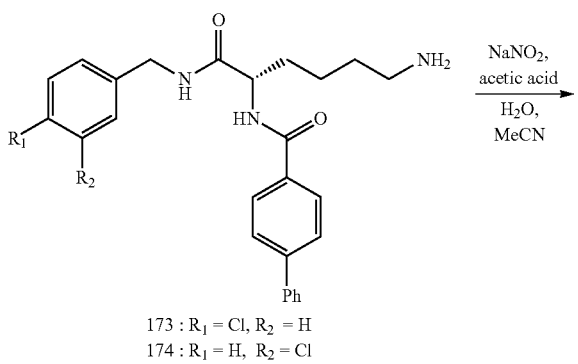

173 : R$_1$ = Cl, R$_2$ = H
174 : R$_1$ = H, R$_2$ = Cl

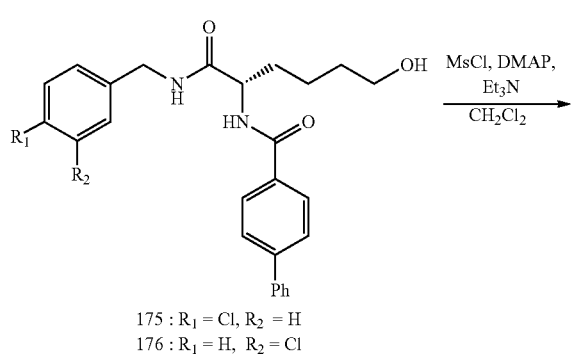

175 : R$_1$ = Cl, R$_2$ = H
176 : R$_1$ = H, R$_2$ = Cl

177 : R$_1$ = Cl, R$_2$ = H
178 : R$_1$ = H, R$_2$ = Cl

-continued

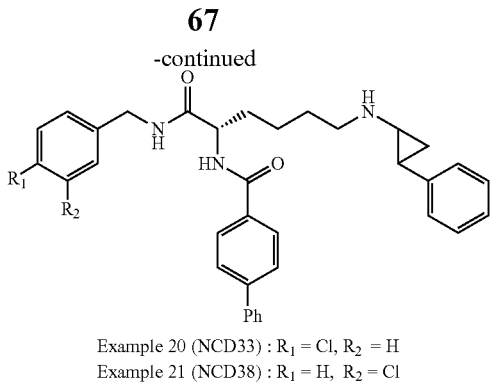

Example 20 (NCD33) : R₁ = Cl, R₂ = H
Example 21 (NCD38) : R₁ = H, R₂ = Cl

Step 18-1: Synthesis of 6-(N-tert-Butoxycarbonyl)amino-2-(N-fluorenylmethoxycarbonyl)amino-N-(4-chlorobenzyl)hexanamide (167)

N-α-Fluorenylmethoxycarbonyl-N-ε-tert-butoxycarbonyl-l-lysine (166) (5.01 g) was dissolved in N,N-dimethylformamide (75 ml). To the solution were added EDCI.HCl (2.53 g), HOBt (1.73 g), triethylamine (1.30 g), and 4-chlorobenzylamine (1.81 g), and the mixture was stirred at room temperature for 12.5 hours. The reaction liquid was diluted with chloroform (150 ml), washed with water (600 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: chloroform to chloroform:methanol=80:1) to give a compound (167) (2.92 g, yield: 46%) as a white solid. ¹H NMR data on the compound (167) is shown below.

¹H-NMR (DMSO-d₆, 300 MHz, δ; ppm) 8.54-8.52 (2H, m), 8.02 (2H, d, J=8.40 Hz), 7.80-7.73 (4H, m), 7.53-7.36 (5H, m), 7.29 (2H, d, J=8.70 Hz), 6.80 (1H, t, J=5.40 Hz), 4.49-4.41 (1H, m), 4.29 (2H, d, J=6.00 Hz), 2.93-2.86 (2H, m), 1.82-1.71 (2H, m), 1.42-1.26 (4H, m), 1.35 (9H, s).

Step 19-1: Synthesis of 6-(N-tert-Butoxycarbonyl)amino-2-(N-fluorenylmethoxycarbonyl)amino-N-(3-chlorobenzyl)hexanamide (168)

A compound (168) (1.99 g, yield: 31%) was obtained as a white solid by the same method as in Step 18-1 of Example 20 except for using 3-chlorobenzylamine (1.82 g). ¹H NMR data on the compound (168) is shown below.

¹H-NMR (DMSO-d₆, 300 MHz, δ; ppm) 8.57-8.54 (2H, m), 8.03 (2H, d, J=8.40 Hz), 7.80-7.73 (4H, m), 7.53-7.21 (7H, m), 6.80 (1H, t, J=5.70 Hz), 4.48-4.41 (1H, m), 4.32-4.29 (2H, m), 2.93-2.87 (2H, m), 1.82-1.74 (2H, m), 1.42-1.27 (4H, m), 1.35 (9H, s).

Step 18-2: Synthesis of 6-(N-tert-Butoxycarbonyl)amino-2-amino-N-(4-chlorobenzyl)hexanamide (169)

6-(N-tert-Butoxycarbonyl)amino-2-(N-fluorenylmethoxycarbonyl)amino-N-(4-chlorobenzyl)hexanamide (167) (2.92 g) was dissolved in dichloromethane (50 ml). To the solution was added piperidine (10 ml), and the mixture was stirred at room temperature for 2 hours. The reaction liquid was concentrated with an evaporator and the residue was purified by silica gel flash column chromatography (developing solvent: chloroform to chloroform:methanol=50:1) to give a compound (169) (1.20 g, yield: 66%) as a yellow amorphous solid. ¹H NMR data on the compound (169) is shown below.

¹H-NMR (DMSO-d₆, 300 MHz, δ; ppm) 8.40-8.35 (1H, m), 7.38 (2H, d, J=8.40 Hz), 7.27 (2H, d, J=8.10 Hz), 6.80-6.74 (1H, m), 4.26 (2H, d, J=5.70 Hz), 3.16-3.12 (1H, m), 2.91-2.85 (2H, m), 1.90-1.78 (2H, m), 1.64-1.51 (1H, m), 1.42-1.24 (3H, m), 1.37 (9H, s).

Step 19-2: Synthesis of 6-(N-tert-Butoxycarbonyl)amino-2-amino-N-(3-chlorobenzyl)hexanamide (170)

A compound (168) (1.05 g, yield: 85%) was obtained as a yellow amorphous solid by the same method as in Step 18-2 of Example 20 except for using 6-(N-tert-butoxycarbonyl)amino-2-(N-fluorenylmethoxycarbonyl)amino-N-(3-chlorobenzyl)hexanamide (168) (1.99 g) in place of 6-(N-tert-butoxycarbonyl)amino-2-(N-fluorenylmethoxycarbonyl)amino-N-(4-chlorobenzyl)hexanamide (167). ¹H NMR data on the compound (170) is shown below.

¹H-NMR (DMSO-d₆, 300 MHz, δ; ppm) 8.40 (1H, t, J=5.85 Hz), 7.73-7.63 (4H, m), 7.22 (1H, d, J=7.20 Hz), 6.76 (1H, t, J=6.00 Hz), 4.63 (2H, d, J=5.70 Hz), 3.26-3.20 (1H, m), 2.91-2.85 (2H, m), 1.84 (2H, s), 1.61-1.51-(1H, m), 1.37-1.23 (3H, m), 1.37 (9H, s).

Step 18-3: Synthesis of 6-(N-tert-Butoxycarbonyl)amino-2-(4-phenylbenzenecarbonyl)amino-N-(4-chlorobenzyl)hexanamide (171)

6-(N-tert-Butoxycarbonyl)amino-2-amino-N-(4-chlorobenzyl)hexanamide (169) (1.20 g) was dissolved in N,N-dimethylformamide (15 ml). To the solution were added EDCI.HCl (746 mg), HOBt (526 mg), triethylamine (658 mg), and 4-phenylbenzoic acid (771 mg), and the mixture was stirred at room temperature for 12 hours. The reaction liquid was diluted with chloroform (150 ml), washed with water (600 ml), saturated aqueous sodium bicarbonate (300 ml), and brine (300 ml), dried over anhydrous sodium sulfate, and filtered. After that, the filtrate was concentrated and the residue was purified by silica gel flash column chromatography (developing solvent: chloroform to chloroform:methanol=97:3) to give a compound (171) (1.46 g, yield: 82%) as a white solid. ¹H NMR data on the compound (171) is shown below.

¹H-NMR (DMSO-d₆, 300 MHz, δ; ppm) 8.54-8.52 (2H, m), 8.02 (2H, d, J=8.40 Hz), 7.80-7.73 (4H, m), 7.53-7.36 (5H, m), 7.29 (2H, d, J=8.70 Hz), 6.80 (1H, t, J=5.40 Hz), 4.49-4.41 (1H, m), 4.29 (2H, d, J=6.00 Hz), 2.93-2.86 (2H, m), 1.82-1.71 (2H, m), 1.42-1.26 (4H, m), 1.35 (9H, s).

Step 19-3: Synthesis of 6-(N-tert-Butoxycarbonyl)amino-2-(4-phenylbenzenecarbonyl)amino-N-(3-chlorobenzyl)hexanamide (172)

A compound (172) (1.10 g, yield: 70%) was obtained as a white solid by the same method as in Step 18-3 of Example 20 except for using 6-(N-tert-butoxycarbonyl)amino-2-amino-N-(3-chlorobenzyl)hexanamide (170) (1.05 g) in place of 6-(N-tert-butoxycarbonyl)amino-2-amino-N-(4-chlorobenzyl)hexanamide (169) (1.20 g). ¹H NMR data on the compound (172) is shown below.

¹H-NMR (DMSO-d₆, 300 MHz, δ; ppm) 8.57-8.54 (2H, m), 8.03 (2H, d, J=8.40 Hz), 7.80-7.73 (4H, m), 7.53-7.21

(7H, m), 6.80 (1H, t, J=5.70 Hz), 4.48-4.41 (1H, m), 4.32-4.29 (2H, m), 2.93-2.87 (2H, m), 1.82-1.74 (2H, m), 1.42-1.27 (4H, m), 1.35 (9H, s).

Step 18-4: Synthesis of 6-Amino-2-(4-phenylbenzenecarbonyl)amino-N-(4-chlorobenzyl)hexanamide Hydrochloride (173)

6-(N-tert-Butoxycarbonyl)amino-2-(4-phenylbenzenecarbonyl)amino-N-(4-chlorobenzyl)hexanamide (171) (1.46 g) was dissolved in dichloromethane (30 ml). To the solution was added a solution of 4 N hydrochloric acid in 1,4-dioxane (6.63 ml) under cooling with ice, and the mixture was stirred at room temperature for 2.5 hours. The reaction liquid was concentrated to give a compound (173) (1.29 g, yield: quant) as a white solid. $^1$H NMR data on the compound (173) is shown below.

$^1$H-NMR (DMSO-$d_6$, 300 MHz, δ; ppm) 8.63-8.59 (2H, m), 8.05 (2H, d, J=8.40 Hz), 7.81-7.73 (6H, m), 7.53-7.37 (5H, m), 7.29 (2H, d, J=8.70 Hz), 4.51-4.44 (1H, m), 4.29 (2H, d, J=6.00 Hz), 2.81-2.73 (2H, m), 1.85-1.77 (2H, m), 1.64-1.32 (4H, m).

Step 19-4: Synthesis of 6-Amino-2-(4-phenylbenzenecarbonyl)amino-N-(3-chlorobenzyl)hexanamide Hydrochloride (174)

A compound (174) (973 mg, yield: quant) was obtained as a white solid by the same method as in Step 18-4 of Example 20 except for using 6-(N-tert-butoxycarbonyl)amino-2-(4-phenylbenzenecarbonyl)amino-N-(3-chlorobenzyl)hexanamide (172) (1.10 g) in place of 6-(N-tert-butoxycarbonyl)amino-2-(4-phenylbenzenecarbonyl)amino-N-(4-chlorobenzyl)hexanamide (171). $^1$H NMR data on the compound (174) is shown below.

$^1$H-NMR (DMSO-$d_6$, 300 MHz, δ; ppm) 8.65-8.61 (2H, m), 8.05 (2H, d, J=8.40 Hz), 7.81-7.73 (6H, m), 7.53-7.22 (7H, m), 4.51-4.44 (1H, m), 4.33-4.30 (2H, m), 2.82-2.73 (2H, m), 1.87-1.79 (2H, m), 1.63-1.33 (4H, m).

Step 18-5: Synthesis of 6-Hydroxy-2-(4-phenylbenzenecarbonyl)amino-N-(4-chlorobenzyl)hexanamide (175)

6-Amino-2-(4-phenylbenzenecarbonyl)amino-N-(4-chlorobenzyl)hexanamide hydrochloride (173) (1.29 g) was dissolved in water (50 ml) and acetonitrile (20 ml). To the solution were added sodium nitrite (4.02 g) and a solution of 4 N hydrochloric acid in 1,4-dioxane (3.31 ml) under cooling with ice, and the mixture was stirred for 1.0 hour under cooling with ice. After 1.5 hours, the reaction liquid was warmed to room temperature and stirred for 2.0 hours. The reaction liquid was concentrated and extracted with ethyl acetate (100 ml). The organic layer was washed with brine (100 ml), dried over anhydrous sodium sulfate, and filtered. After that, the filtrate was concentrated and the residue was purified by silica gel flash column chromatography (developing solvent: chloroform:methanol=100:1 to chloroform:methanol=30:1) to give a compound (175) (561 mg, yield: 47%) as a white solid. $^1$H NMR data on the compound (175) is shown below.

$^1$H-NMR (DMSO-$d_6$, 300 MHz, δ; ppm) 8.57-8.52 (2H, m), 8.02 (2H, d, J=8.40 Hz), 7.80-7.73 (4H, m), 7.45-7.36 (5H, m), 7.29 (2H, d, J=8.70 Hz), 4.50-4.42 (1H, m), 4.39 (1H, t, J=5.10 Hz), 4.29 (2H, d, J=6.00 Hz), 2.81-2.73 (2H, m), 1.82-1.74 (2H, m), 1.47-1.34 (4H, m).

Step 19-5: Synthesis of 6-Hydroxy-2-(4-phenylbenzenecarbonyl)amino-N-(3-chlorobenzyl)hexanamide (176)

A compound (176) (408 mg, yield: 45%) was obtained as a white solid by the same method as in Step 18-5 of Example 20 except for using 6-amino-2-(4-phenylbenzenecarbonyl)amino-N-(3-chlorobenzyl)hexanamide hydrochloride (174) (973 mg) in place of 6-amino-2-(4-phenylbenzenecarbonyl)amino-N-(4-chlorobenzyl)hexanamide hydrochloride (173). $^1$H NMR data on the compound (176) is shown below.

$^1$H-NMR (DMSO-$d_6$, 300 MHz, δ; ppm) 8.58-8.54 (2H, m), 8.03 (2H, d, J=8.40 Hz), 7.80-7.73 (4H, m), 7.53-7.22 (7H, m), 4.50-4.42 (1H, m), 4.38 (1H, t, J=5.10 Hz), 4.31 (2H, d, J=6.00 Hz), 3.42-3.36 (2H, m), 2.82-2.73 (2H, m), 1.84-1.75 (2H, m), 1.49-1.31 (4H, m).

Step 18-6: Synthesis of 6-(O-Methanesulfonyl)-2-(4-phenylbenzenecarbonyl)amino-N-(4-chlorobenzyl)hexanamide (177)

6-Hydroxy-2-(4-phenylbenzenecarbonyl)amino-N-(4-chlorobenzyl)hexanamide (175) (561 mg) was dissolved in pyridine (5 ml). To the solution was added methanesulfonyl chloride (229 mg) at 0° C., and the mixture was stirred at room temperature for 3.0 hours. The reaction liquid was diluted with chloroform (30 ml) and washed with 3 N hydrochloric acid (100 ml) and brine (100 ml). The organic layer was dried over anhydrous sodium sulfate and filtered. After that, the filtrate was concentrated and the residue was purified by silica gel flash column chromatography (developing solvent: chloroform to chloroform:methanol=95:5) to give a compound (177) (441 mg, yield: 67%) as a white solid. $^1$H NMR data on the compound (177) is shown below.

$^1$H-NMR (DMSO-$d_6$, 300 MHz, δ; ppm) 8.60-8.56 (2H, m), 8.02 (2H, d, J=8.70 Hz), 7.80-7.73 (4H, m), 7.45-7.37 (5H, m), 7.29 (2H, d, J=8.40 Hz), 4.52-4.42 (1H, m), 4.29 (2H, d, J=5.70 Hz), 4.20 (2H, t, J=6.45 Hz), 3.16 (3H, s), 1.87-1.65 (4H, m), 1.52-1.35 (2H, m).

Step 19-6: Synthesis of 6-(O-Methanesulfonyl)-2-(4-phenylbenzenecarbonyl)amino-N-(3-chlorobenzyl)hexanamide (178)

A compound (178) (307 mg, yield: 58%) was obtained as a white solid by the same method as in Step 18-6 of Example 20 except for using 6-hydroxy-2-(4-phenylbenzenecarbonyl)amino-N-(3-chlorobenzyl)hexanamide (176) (480 mg) in place of 6-hydroxy-2-(4-phenylbenzenecarbonyl)amino-N-(4-chlorobenzyl)hexanamide (175). $^1$H NMR data on the compound (178) is shown below.

$^1$H-NMR (DMSO-$d_6$, 300 MHz, δ; ppm) 8.63-8.58 (2H, m), 8.04 (2H, d, J=8.40 Hz), 7.81-7.73 (4H, m), 7.53-7.22 (7H, m), 4.52-4.44 (1H, m), 4.32 (2H, t, J=4.50 Hz), 4.20 (2H, t, J=6.45 Hz), 3.16 (3H, s), 1.88-1.66 (4H, m), 1.53-1.39 (2H, m).

Step 18-7: Synthesis of 2-[N-(4-Phenylbenzenecarbonyl)]amino-6-(trans-2-phenylcyclopropan-1-amino)-N-(4-chlorobenzyl)hexanamide Hydrochloride (Example 20, NCD33)

6-(O-Methanesulfonyl)-2-(4-phenylbenzenecarbonyl)amino-N-(4-chlorobenzyl)hexanamide (177) (139 mg) was dissolved in N,N-dimethylformamide (0.5 ml). To the solution were added trans-2-phenylcyclopropylamine (169 mg) and potassium carbonate (67.4 mg), and the mixture was stirred at 50° C. for 24 hours. The reaction liquid was diluted with dichloromethane (20 ml), washed with saturated aqueous sodium bicarbonate (50 ml) and brine (50 ml), dried over anhydrous sodium sulfate, and filtered. After that, the filtrate was concentrated and the residue was purified by silica gel flash column chromatography (developing solvent: chloroform to chloroform:methanol=98:2) to give a yellow amorphous solid (109 mg, yield: 72%). The resultant yellow amorphous solid was recrystallized from dichloromethane-diethyl ether to give a compound (Example 20, NCD33) as a white solid. Melting point, $^1$H NMR, $^{13}$C NMR, MS (FAB), and elemental analysis data on the compound (Example 20, NCD33) are shown below.

Melting point: 110° C. to 113° C.

$^1$H-NMR (CD$_3$OD, 300 MHz, δ; ppm) $^1$H-NMR (CD$_3$OD, 300 MHz, δ; ppm) 7.97 (2H, d, J=8.10 Hz), 7.73 (2H, dt, J=8.40 Hz), 7.66 (2H, dt, J=7.20 Hz), 7.47 (2H, tt, J=7.35 Hz), 7.41-7.13 (10H, m), 4.64-4.59 (1H, m), 4.39 (2H, s), 3.17 (2H, t, J=7.50 Hz), 2.97-2.91 (1H, m), 2.51-2.44 (1H, m), 2.04-1.75 (4H, m), 1.61-1.46 (3H, m), 1.36 (1H, q, J=7.10 Hz)

$^{13}$C-NMR (CD$_3$OD, 300 MHz, δ; ppm) 174.4, 170.2, 146.1, 141.2, 139.4, 138.9, 134.0, 133.8, 130.2, 130.1, 129.8, 129.6, 129.3, 128.2, 128.1, 127.5, 55.2, 43.5, 39.2, 32.5, 26.8, 24.3, 22.6, 13.6

HRMS calcd. for C$_{35}$H$_{37}$ClO$_2$N$_3$ (MH—Cl$^-$), 566.2574. found, 566.2578.

Anal. Calcd. for C$_{35}$H$_{37}$Cl$_2$O$_2$N$_3$·1/3H2O: C, 69.07; H, 6.24; N, 6.90. Found: C, 68.81; H, 5.89; N, 7.05.

Step 19-7: Synthesis of 2-[N-(4-Phenylbenzenecarbonyl)]amino-6-(trans-2-phenylcyclopropan-1-amino)-N-(3-chlorobenzyl)hexanamide Hydrochloride (Example 21, NCD38)

A compound (110 mg, yield: 73%) was obtained as a yellow amorphous solid by the same method as in Step 18-7 of Example 20 except for using 6-(O-methanesulfonyl)-2-(4-phenylbenzenecarbonyl)amino-N-(3-chlorobenzyl)hexanamide (178) (136 mg) in place of 6-(0-methanesulfonyl)-2-(4-phenylbenzenecarbonyl)amino-N-(4-chlorobenzyl) hexanamide (177). The resultant yellow amorphous solid was purified by HPLC (Gradient (IV)) to give a compound (Example 21, NCD38) as a colorless amorphous solid. $^1$H NMR, $^{13}$C NMR, MS (FAB), and purity data on the compound (Example 21, NCD38) are shown below.

$^1$H-NMR (CD$_3$OD, 300 MHz, δ; ppm) 7.96 (2H, d, J=8.70 Hz), 7.72 (2H, d, J=8.70 Hz), 7.68-7.64 (2H, m), 7.47 (2H, tt, J=7.35 Hz), 7.41-7.14 (10H, m), 4.65-4.60 (1H, m), 4.42-4.39 (2H, m), 3.18 (2H, t, J=7.35 Hz), 2.98-2.92 (1H, m), 2.48-2.42 (1H, m), 2.07-1.75 (4H, m), 1.66-1.44 (3H, m), 1.37 (1H, q, J=7.10 Hz)

$^{13}$C-NMR (CD$_3$OD, 300 MHz, δ; ppm) 174.4, 170.1, 146.0, 142.4, 141.2, 139.3, 135.4, 133.7, 131.1, 130.1, 129.8, 129.2, 129.2, 128.5, 128.3, 128.1, 128.1, 128.1, 127.4, 126.9, 55.2, 43.6, 39.1, 32.4, 26.7, 24.2, 22.5, 13.4

HRMS calcd. for C$_{35}$H$_{37}$ClO$_2$N$_3$ (MH—CF$_3$COO$^-$), 566.2574. found, 566.2569.

HPLC t$_R$=22.34 min (Gradient (VI), purity 98.0%).

[Evaluation of Compound]

The compounds of Example 1 to Example 21 obtained as described above were each subjected to an LSD1 inhibitory activity test, a monoamine oxidase inhibitory activity test, and HeLa cell and SH-SY-5Y cell growth inhibition tests. trans-2-Phenylcyclopropylamine (t-PCPA, Comparative Example (Comp. Ex.) 1)) and (S)-trans-N-3-[3-(2-aminocyclopropyl)phenoxy]-1-benzylcarbamoylpropylbenzamide hydrochloride disclosed in Patent Literature 1 (NCL-1, Comparative Example (Comp. Ex.) 2)) were used as Comparative Examples.

<LSD1 Inhibition Test>

An LSD1 enzyme was prepared as described below.

A plasmid encoding a recombinant protein having five histidine residues added to the N-terminus of full-length LSD1 (1-851aa) was prepared. Recombinant *Escherichia coli* transformed with this plasmid was used to express LSD1. After that, recombinant *Escherichia coli* was lysed by ultrasonication, and its soluble fraction was purified by HisTrap chromatography to give an LSD1 enzyme solution. The enzyme activity of LSD1 was measured by: subjecting hydrogen peroxide to be generated during a demethylation reaction of LSD1 to color development with peroxidase and a reagent; and quantifying the hydrogen peroxide by an absorbance method. More specifically, in a 384-well microtiter plate, 20 μl of a solution containing 50 mM Hepes-NaOH buffer (pH 7.5), 0.1 mM 4-aminoantipyrine, 1 mM 3,5-dichloro-2-hydroxybenzenesulfonic acid, 20 μM histone H3-lysine 4 dimethyl peptide, 0.05 M LSD1, and 0.35 μM horseradish peroxidase was used to measure an enzyme reaction with time at 25° C. for 30 minutes. Spectra Max M2e (Molecular Devices) was used for the measurement and the absorbance of a product at 515 nm was determined by the measurement. In addition, regarding inhibitory activity, the enzyme activity at the time of the addition of dimethyl sulfoxide was defined as 100%, residual activity was measured by variously changing the addition concentration of a phenylcyclopropylamine derivative, and a concentration at which activity was inhibited by 50% (IC$_{50}$) was determined.

The results of the LSD1 inhibition test are shown in Tables 1 to 3. Each of the compounds of Examples 1 to 21 exhibited LSD1 inhibitory activity comparable to those of Comparative Example 1 and Comparative Example 2 or higher than those of Comparative Example 1 and Comparative Example 2. In particular, the compounds of Example 1, Examples 4 to 6, and Example 8 were found to have very high LSD1 inhibitory activities, which were from about 170 times to 430 times as high as that of Comparative Example 1 and were from about 7 times to 18 times as high as that of Comparative Example 2.

<Monoamine Oxidase Inhibition Test>

The compounds of Examples 8, 19, 20, and 21, which exhibited high LSD1 inhibitory activities and cell growth inhibitory activities, were measured for their monoamine oxidase A (MAO-A) and monoamine oxidase B (MAO-B) inhibitory activities through use of a MAO-Glo assay kit available from Promega and MAO-A and MAO-B purchased from Sigma-Aldrich as described below.

12.5 μL of 4×MAO substrate (final concentration: 40 μM), 12.5 μL of 4× inhibitor solution (final concentration: 0.01 μM to 100 μM), and 25 μL of MAO-A (final concentration: 9 unit/mL) or 25 μL of MAO-B (final concentration: 2.3 unit/mL) were mixed and the mixture was subjected to a reaction at room temperature for 1 hour. To the reaction liquid was added 50 μL of a luciferin detection reagent, and the mixture was subjected to a reaction at room temperature for 20 minutes. A fluorescence plate reader was also used to measure a fluorescence intensity (fluorescence measuring wavelength: 562 nm), and an IC$_{50}$ value (inhibitor concentration at which an enzyme was inhibited by 50%) was determined.

The results of the monoamine oxidase inhibition test are shown in Tables 1 to 3. Each of the compounds of Examples 8, 19, 20, and 21 exhibited an IC$_{50}$ value 50 times or more as high as that of Comparative Example 1, and MAO-A and MAO-B inhibitory activities much lower than those of Comparative Example 1.

TABLE 1
| Compound | Structure | IC$_{50}$ (μM) | | |
|---|---|---|---|---|
| | | LSD1 | MAO A | MAO B |
| Comp. Ex. 1 (t-PCPA) | 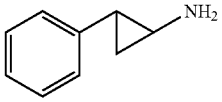 | 41 | 1.5 | 1.4 |
| Comp. Ex. 2 (NCL1) | 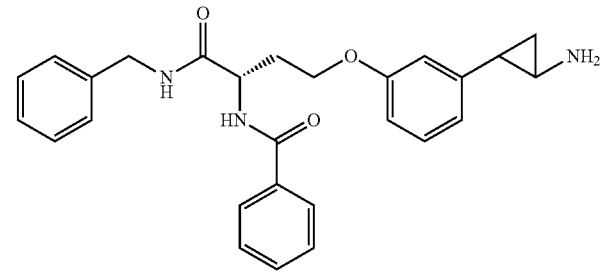 [SMILES: NC1CC1c1cccc(OCC[C@H](NC(=O)c2ccccc2)C(=O)NCc2ccccc2)c1] | 2.5 | 129 | 326 |
| Example 1 (NCD18) | 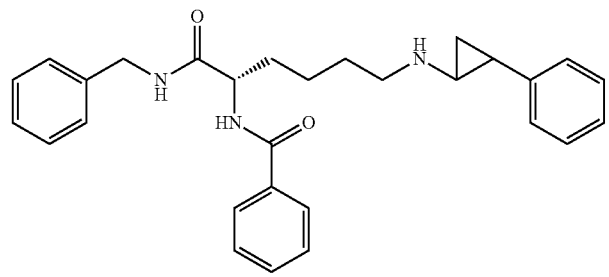 [SMILES: O=C(N[C@@H](CCCCNC1CC1c1ccccc1)C(=O)NCc1ccccc1)c1ccccc1] | 0.16 | NT | NT |
| Example 2 (NCD29) | 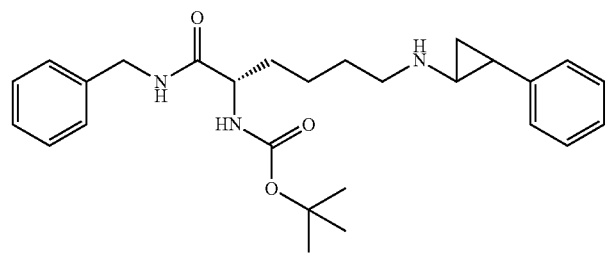 [SMILES: CC(C)(C)OC(=O)N[C@@H](CCCCNC1CC1c1ccccc1)C(=O)NCc1ccccc1] | 1.2 | NT | NT |
| Example 3 (NCD30) | 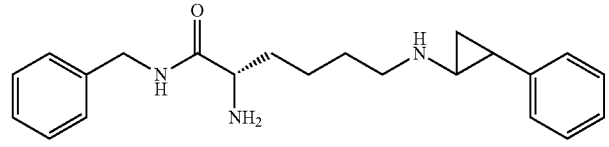 [SMILES: N[C@@H](CCCCNC1CC1c1ccccc1)C(=O)NCc1ccccc1] | 0.06 | NT | NT |
| Example 4 (NCD21) | 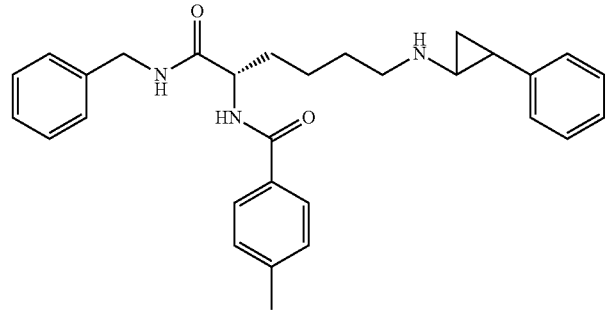 [SMILES: Cc1ccc(C(=O)N[C@@H](CCCCNC2CC2c2ccccc2)C(=O)NCc2ccccc2)cc1] | 0.44 | NT | NT |

TABLE 1-continued

| Compound | Structure | IC$_{50}$ (μM) | | |
|---|---|---|---|---|
| | | LSD1 | MAO A | MAO B |
| Example 5 (NCD22) | 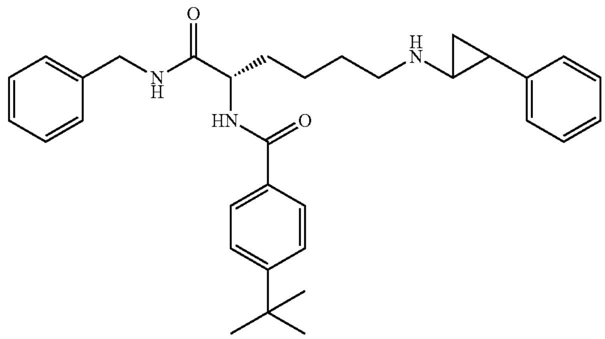 [SMILES: CC(C)(C)c1ccc(C(=O)N[C@@H](CCCCNC2CC2c2ccccc2)C(=O)NCc2ccccc2)cc1] | 0.79 | NT | NT |
| Example 6 (NCD23) | 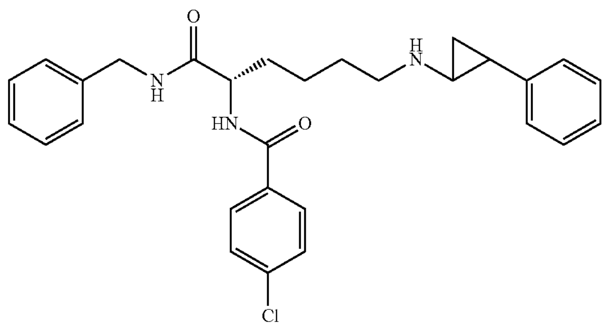 [SMILES: O=C(N[C@@H](CCCCNC1CC1c1ccccc1)C(=O)NCc1ccccc1)c1ccc(Cl)cc1] | 0.20 | NT | NT |
| Example 7 (NCD24) | 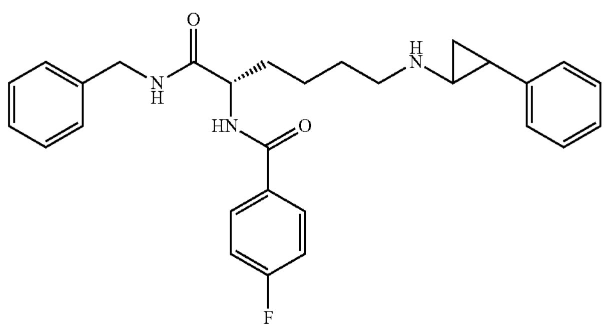 [SMILES: O=C(N[C@@H](CCCCNC1CC1c1ccccc1)C(=O)NCc1ccccc1)c1ccc(F)cc1] | 0.25 | NT | NT |

TABLE 2

| Compound | Structure | IC$_{50}$ (μM) | | |
|---|---|---|---|---|
| | | LSD1 | MAO A | MAO B |
| Example 8 (NCD25) | 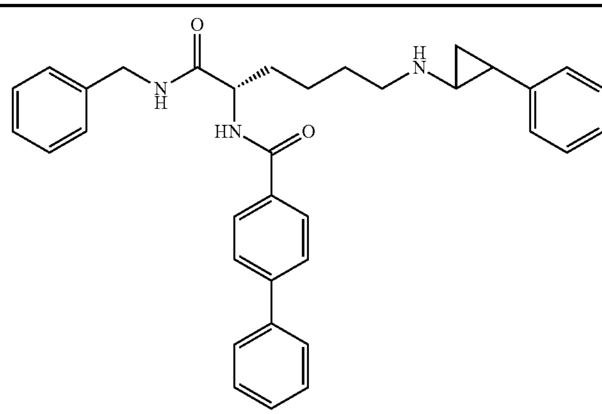 | 0.47 | 86 | >100 |

TABLE 2-continued
| Compound | Structure | IC$_{50}$ (μM) | | |
| --- | --- | --- | --- | --- |
| | | LSD1 | MAO A | MAO B |
| Example 9 (NCD26) | 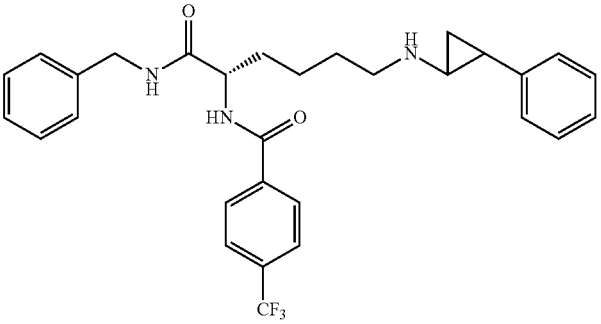 [SMILES: O=C(N[C@@H](CCCCNC1CC1c1ccccc1)C(=O)NCc1ccccc1)c1ccc(C(F)(F)F)cc1] | 0.38 | NT | NT |
| Example 10 (NCD27) | 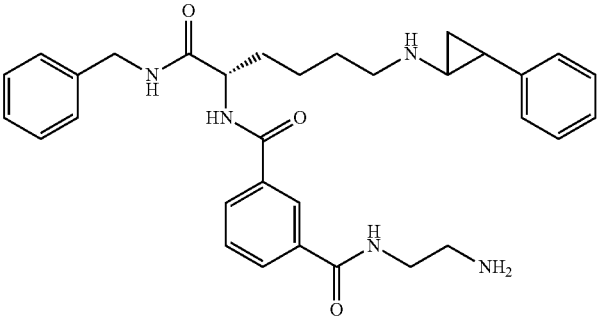 [SMILES: NCCNC(=O)c1cccc(C(=O)N[C@@H](CCCCNC2CC2c2ccccc2)C(=O)NCc2ccccc2)c1] | 0.10 | NT | NT |
| Example 11 (NCD28) | 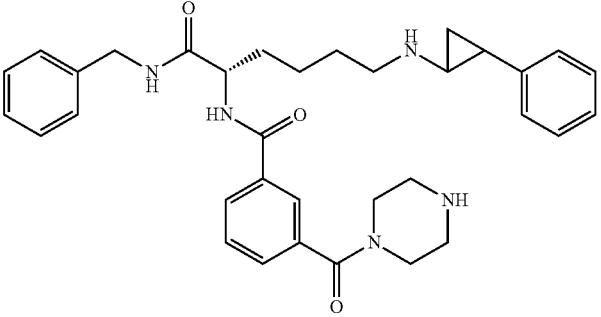 [SMILES: O=C(N[C@@H](CCCCNC1CC1c1ccccc1)C(=O)NCc1ccccc1)c1cccc(C(=O)N2CCNCC2)c1] | 0.25 | NT | NT |
| Example 12 (NCD31) | 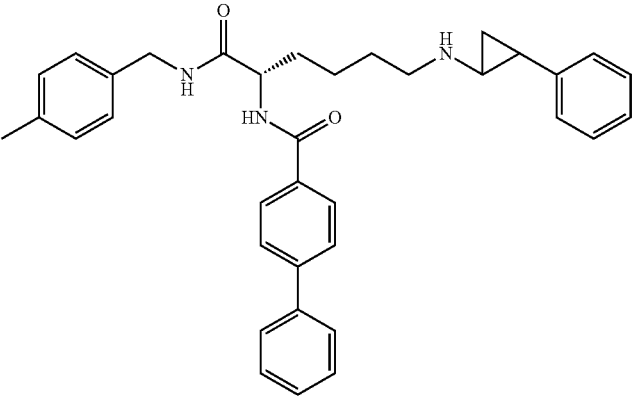 [SMILES: Cc1ccc(CNC(=O)[C@H](CCCCNC2CC2c2ccccc2)NC(=O)c2ccc(-c3ccccc3)cc2)cc1] | 0.60 | NT | NT |

TABLE 2-continued
| Compound | Structure | IC$_{50}$ (μM) LSD1 | MAO A | MAO B |
|---|---|---|---|---|
| Example 13 (NCD32) | 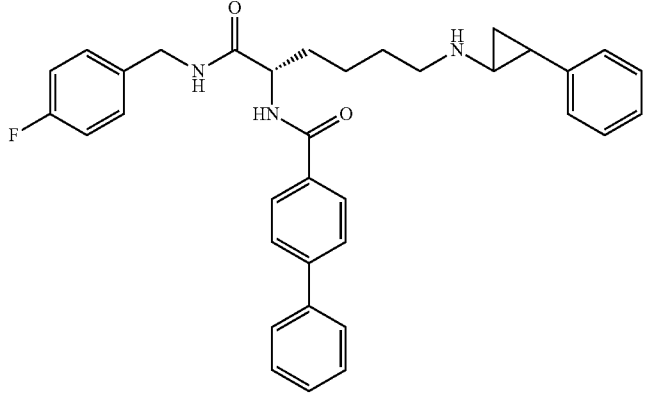 [SMILES: O=C(N[C@@H](CCCCNC1CC1c1ccccc1)C(=O)NCc1ccc(F)cc1)c1ccc(-c2ccccc2)cc1] | 0.75 | NT | NT |
| Example 14 (NCD34) | 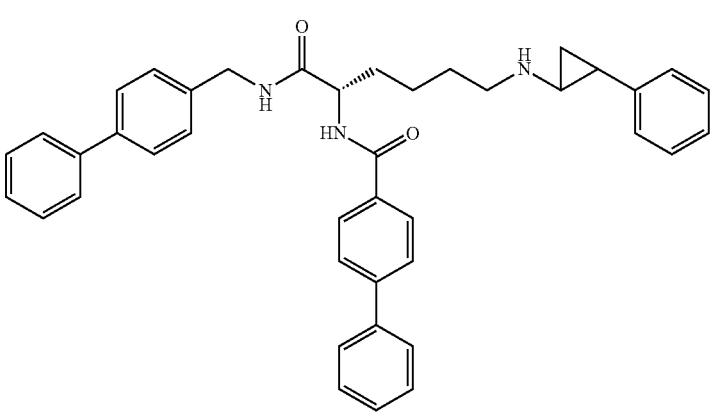 [SMILES: O=C(N[C@@H](CCCCNC1CC1c1ccccc1)C(=O)NCc1ccc(-c2ccccc2)cc1)c1ccc(-c2ccccc2)cc1] | 2.7 | NT | NT |
TABLE 3
| Compound | Structure | IC$_{50}$ (μM) LSD1 | MAO A | MAO B |
|---|---|---|---|---|
| Example 15 (NCD35) | 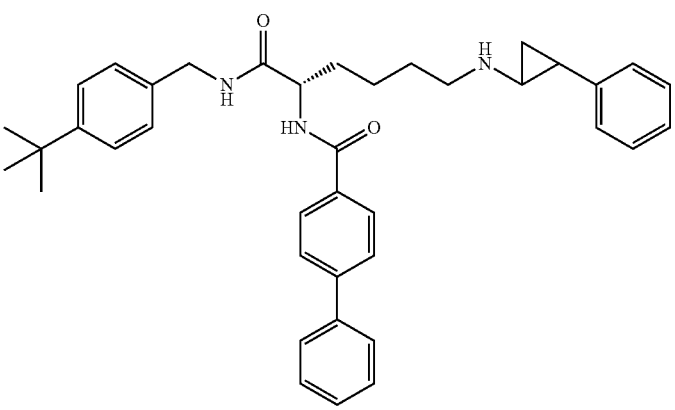 [SMILES: CC(C)(C)c1ccc(CNC(=O)[C@H](CCCCNC2CC2c2ccccc2)NC(=O)c2ccc(-c3ccccc3)cc2)cc1] | 1.2 | NT | NT |

TABLE 3-continued

| Compound | Structure | IC$_{50}$ (μM) | | |
|---|---|---|---|---|
| | | LSD1 | MAO A | MAO B |
| Example 16 (NCD36) | 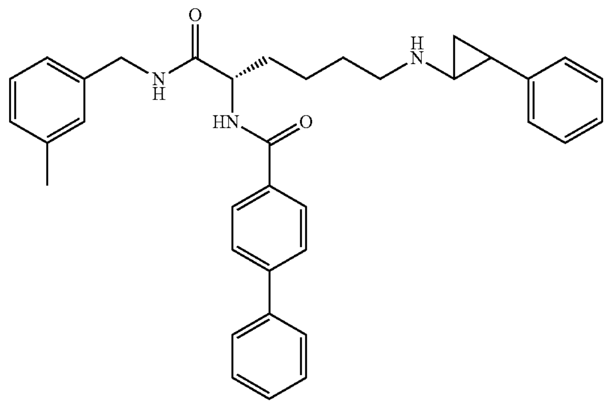 [SMILES: Cc1cccc(CNC(=O)[C@H](CCCCNC2CC2c2ccccc2)NC(=O)c2ccc(-c3ccccc3)cc2)c1] | 0.68 | NT | NT |
| Example 17 (NCD37) | 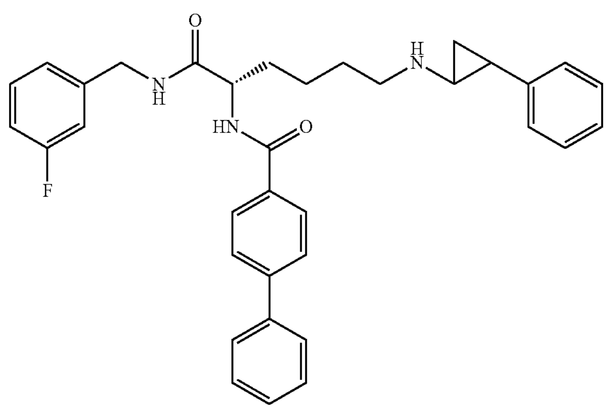 [SMILES: O=C(N[C@@H](CCCCNC1CC1c1ccccc1)C(=O)NCc1cccc(F)c1)c1ccc(-c2ccccc2)cc1] | 0.67 | NT | NT |
| Example 18 (NCD39) | 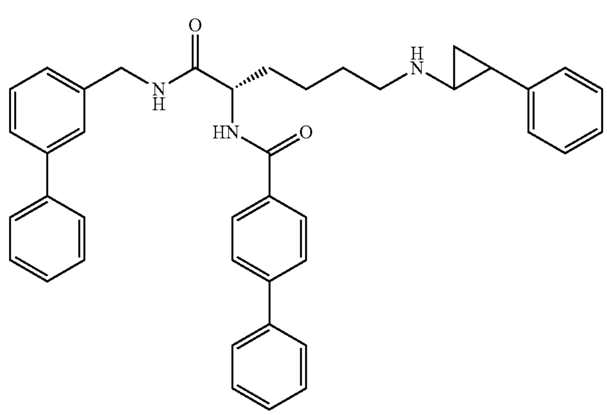 [SMILES: O=C(N[C@@H](CCCCNC1CC1c1ccccc1)C(=O)NCc1cccc(-c2ccccc2)c1)c1ccc(-c2ccccc2)cc1] | 0.98 | NT | NT |

TABLE 3-continued

| Compound | Structure | IC$_{50}$ (μM) | | |
| --- | --- | --- | --- | --- |
| | | LSD1 | MAO A | MAO B |
| Example 19 (NCD41) | 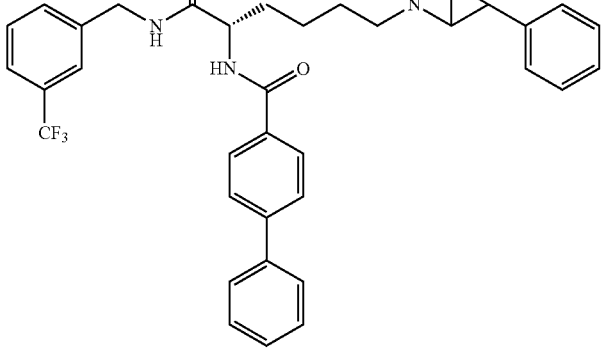 | 0.58 | >100 | >100 |
| Example 20 (NCD33) | 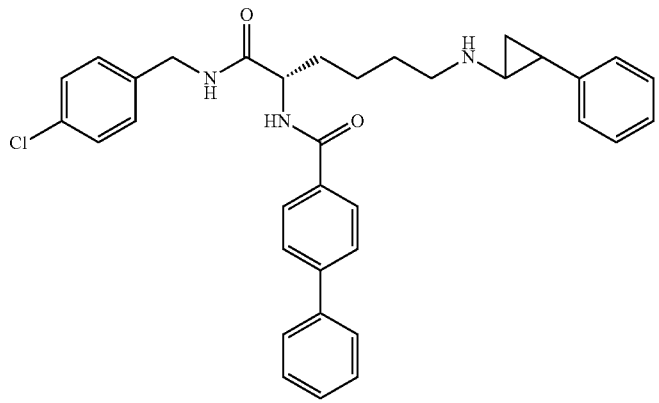 [SMILES: O=C(N[C@@H](CCCCNC1CC1c1ccccc1)C(=O)NCc1ccc(Cl)cc1)c1ccc(-c2ccccc2)cc1] | 0.45 | >100 | >100 |
| Example 21 (NCD38) | 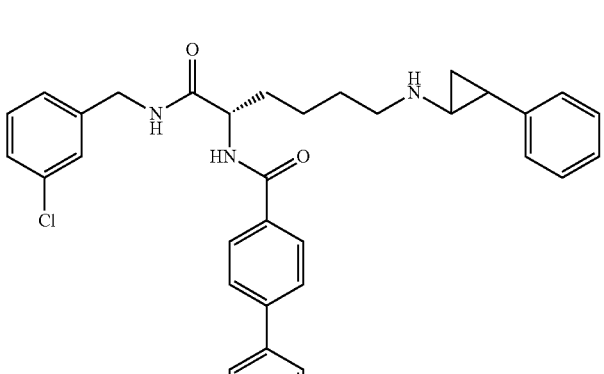 | 0.77 | >100 | >100 |

<Cancer Cell Growth Inhibition Evaluation>

Evaluation was performed by measuring the inhibitory activities of a compound against the growth of a human cervical cancer-derived cell line, HeLa cells, and a human neuroblastoma cell line, SH-SY5Y cells. Details thereof are shown below.

The cell growth inhibitory activities were each determined by a 3-[4,5-dimethylthiazol-2-yl]-2,5-diphenyltetrazolium bromide (MTT) assay. This assay involves, as a principle thereof, measuring an absorbance at the time of color development through a reaction of NADH, which is contained in the mitochondria of viable cells, and MTT to measure the amount of NADH. The assay was performed by the following procedure.

HeLa cells were plated at 5,000 cells per well in a 96-well microtiter plate in 100 μl of 10% fetal bovine serum-containing RPMI 1640 medium, and cultured for 24 hours in a $CO_2$ incubator. After the culture, a compound was added. Then, the cells were cultured for an additional 48 hours, and then 5 mg/ml MTT liquid was added at 10 μl per well. The cells were cultured for an additional 3 hours in a $CO_2$ incubator. A solubilization solution (0.04 mol/l hydrochloric acid-isopropanol) was added at 100 μl per well and the mixture was vigorously vortexed. After that, an absorbance at 560 nm was measured with Fusion-aFP (manufactured by PerkinElmer) and the amount of viable cells was determined. In addition, regarding inhibitory activity, the enzyme activity at the time of the addition of dimethyl sulfoxide was defined as 100%, residual activity was measured by variously changing the addition concentration of a phenylcyclopropylamine derivative, and a concentration at which activity was inhibited by 50% ($GI_{50}$) was determined.

The results of the cancer cell growth inhibition evaluation are shown in Table 4. Each of the compounds of Examples 5, 6, 8, 9, and 12 to 21 exhibited cancer cell growth inhibitory activity higher than those of Comparative Example 1 and Comparative Example 2. In particular, each of the compounds of Examples 15, 16, and 19 to 21 exhibited very high cancer cell growth inhibitory activity.

TABLE 4

| compound | $GI_{50}$ (μM) | |
|---|---|---|
| | HeLa | SH-SY5Y |
| Comp. Ex. 1 (t-PCPA) | >500 | 503 |
| Comp. Ex. 2 (NCL1) | 13 | 27 |
| Example 5 (NCD22) | 12 | 4.8 |
| Example 6 (NCD23) | 13 | 11 |
| Example 8 (NCD25) | 11 | 4.0 |
| Example 9 (NCD26) | 13 | 5.4 |
| Example 12 (NCD31) | 4.4 | 3.5 |
| Example 13 (NCD32) | 4.4 | 3.9 |
| Example 14 (NCD34) | 5.2 | 6.4 |
| Example 15 (NCD35) | 4.0 | 2.7 |
| Example 16 (NCD36) | 4.2 | 2.3 |
| Example 17 (NCD37) | 10.9 | 4.1 |
| Example 18 (NCD39) | 9.7 | 3.8 |
| Example 19 (NCD41) | 4.3 | 2.9 |
| Example 20 (NCD33) | 4.0 | 1.4 |
| Example 21 (NCD38) | 4.3 | 2.7 |

<Leukemia Cell Growth Inhibition Evaluation>

The compounds of Example 8 (NCD25), Example 19 (NCD41), and Example 21 (NCD38), which exhibited high LSD1 inhibitory activities and cell growth inhibitory activities, were evaluated for their growth inhibition on human and murine leukemia cell lines by the following procedure.

HL60, THP-1, K562, U937, KG1a, HEL, and MDS-L were used as human leukemia cells. The cell lines are cell lines established from various subtypes such as acute myeloid leukemia, acute promyelocytic leukemia, acute monocytic leukemia, acute erythroid leukemia, and myelodysplastic syndromes, which progress to leukemia. Cells obtained by introducing leukemia fusion genes MLL/AF9, MLL/SEPT6, and MLL/ENL into the bone marrow of normal mice with a retrovirus so as to develop leukemia were used as murine leukemia cell lines.

A cell growth inhibition experiment was performed by using WST-8 reagent (manufactured by Nacalai), which was a modified 3-[4,5-dimethylthiazol-2-yl]-2,5-diphenyltetrazolium bromide (MTT) assay in conformity with the instruction manual provided by the manufacturer. This assay method involves, as a principle thereof, measuring an absorbance (a peak at from 450 nm to 490 nm) at the time of color development through a reaction of NADH, which is contained in the mitochondria of viable cells, and WST-8 to measure the amount of NADH. Specifically, the assay was performed by the following procedure.

The respective cells were adjusted to 100,000 cells per ml of a medium (human leukemia cells: 10% fetal bovine serum-containing RPMI 1640 (Roswell Park Memorial Institute) medium; murine leukemia cells: Iscove's Modified Dulbecco's Medium (IMDM medium) containing 10% fetal bovine serum and 5 ng/ml murine interleukin 3 (mIL-3)). The cells were plated at 50 μl, i.e., 5,000 cells per well in a 96-well microtiter plate. Next, a test compound dissolved in DMSO was mixed at various concentrations into the same medium, and 50 μl of each of the mixtures was added to each well. A medium was prepared so that the final concentration of the test compound was from 0 μM to 50 μM and so that the addition amount of DMSO was the same, and the cells were cultured in a $CO_2$ incubator. On day 0 before the addition and on day 1, day 2, and day 3 after the addition, WST-8 reagent was added at 20 μl per well, and the cells were cultured for 1 hour in a $CO_2$ incubator. After that, measurement was performed with ARVO X3 (manufactured by PerkinElmer).

Specifically, an absorbance at 450 nm was measured, an absorbance at 595 nm was measured in the same well, and the absorbance at 595 nm was subtracted from the absorbance at 450 nm to perform background correction for the well itself. Further, a well containing only a medium free of cells was subjected to the same measurement. A value in this case was also subtracted. Thus, the amount of viable cells was represented as a numerical value with correction of the influence of a medicament or a medium as well. Under a condition not containing the test compound (addition of only dimethyl sulfoxide), an exponential increase in number of viable cells on day 1, day 2, and day 3 in the stated order was confirmed. Data on day 3 (corresponding to 72-hour culture) was used to determine a concentration ($GI_{50}$) of the test compound at which cell growth was inhibited so that the number of viable cells was reduced by 50% with respect to the number of viable cells in the case of not containing the test compound defined as 100%.

The results are shown in Tables 5 and 6. The compound of Comparative Example 2 exhibited high growth inhibitory effects on the murine leukemia cell lines, but exhibited a variation in growth inhibitory effect on the human leukemia cell lines depending on the cell lines. On the other hand, the compounds of Examples 8, 19, and 21 exhibited higher growth suppressing effects on the human leukemia cell lines than Comparative Example 2. In addition, the compounds of Examples 8, 19, and 21 also exhibited very high growth suppressing effects on the murine leukemia cell lines.

All-trans-retinoic acid (ATRA) is used as a therapeutic drug for acute promyelocytic leukemia (APL). It has been reported that the combined use of ATRA and Comparative Example 1 (t-PCPA) exhibits high growth suppressing effects on human leukemia cell lines. On the other hand, the compounds of Examples 8, 19, and 21 exhibited high growth suppressing effects on human leukemia cell lines by themselves without being used in combination with ATRA.

TABLE 5

| compound | Human leukemia cell line $GI_{50}$ (μM) | | | | | | | |
|---|---|---|---|---|---|---|---|---|
| | HL60 | THP1 | K562 | U937 | M7 | KG1a | HEL | MDS-L |
| Comp. Ex. 2 (NCL1) | 6.1-33 | >50 | 25-50 | 25-50 | >50 | >50 | NT | NT |
| Example 8 (NCD25) | 4.0-5.0 | 5.0-6.0 | 3.2 | 4.6 | Around 6.0 | Around 6.3 | <1.3 | <1.3 |

TABLE 5-continued

| | Human leukemia cell line GI$_{50}$ (μM) | | | | | | | |
|---|---|---|---|---|---|---|---|---|
| compound | HL60 | THP1 | K562 | U937 | M7 | KG1a | HEL | MDS-L |
| Example 19 (NCD41) | 2.5-5.0 | 5.0-10 | NT | 10-20 | NT | 5.0-10 | Around 5.0 | <1.3 |
| Example 21 (NCD38) | 5.0-10 | 10-20 | NT | 10-20 | NT | 10-20 | <1.3 | <1.3 |

TABLE 6

| | Mouse MLL-fusion leukemia cell line GI$_{50}$ (μM) | | |
|---|---|---|---|
| compound | MLL/AF9 | MLL/SEPT6 | MLL/ENL |
| Comp. Ex. 2 (NCL1) | <3.1 | NT | <3.1 |
| Example 8 (NCD25) | <2.0 | 4.0-5.0 | NT |
| Example 19 (NCD41) | <1.25 | 2.5-5.0 | NT |
| | <1.25 | 2.5-5.0 | NT |

<Normal Cell Growth Inhibition Evaluation>

The compounds of Example 8 (NCD25), Example 19 (NCD41), and Example 21 (NCD38), which exhibited high LSD1 inhibitory activities and cell growth inhibitory activities, were evaluated for their growth suppression on human normal cells by the following procedure.

Normal bone marrow cells start to lose their growth activities from the moment of being taken out from the bone marrow, and hence it is difficult to perform evaluation in a liquid medium. In general, a semi-solid medium obtained by adding a cytokine involved in differentiation induction to a methylcellulose medium is used to evaluate a colony forming ability. Some of the bone marrow cells contain hematopoietic stem cells and precursor cells, which are sources of hematopoietic cells, and these cells can create a mass (called a colony) formed of several tens, several hundreds, and in some cases, several thousands of cells from a single cell on a semi-solid medium. The colony forming ability of the bone marrow cells may be evaluated by counting the number of the colonies. The colony forming ability in the semi-solid medium well reflects an actual supply ability and construction ability from the hematopoietic stem cells and precursor cells to the hematopoietic cells in vivo. That is, when a certain compound inhibits a colony forming ability at a certain concentration, bone marrow suppression is estimated to be caused at such concentration in an actual living body as well.

To 3 ml of MethoCult M3434 (methylcellulose-based semi-solid medium; StemCell Technologies; containing interleukin 3(IL-3), interleukin 6 (IL-6), erythropoietin (EPO), and stem cell factor (SCF)) were added 600,000 bone marrow cells of normal mice (suspended in 300 μl of IMDM medium), and the mixture was stirred well and plated at 1.1 ml per 3.5-cm culture dish. The cells were cultured under the conditions of 5% CO$_2$ and 37° C. for 10 days in an incubator. A mass in which the number of cells was 50 or more was defined as a colony, and the number of colonies formed on each dish was counted.

The results are shown in FIG. 1. In Examples 8 and 19, the colony forming ability was not inhibited at a concentration of up to 5 μM, but was remarkably inhibited at 10 μM. In addition, in Example 21, the colony forming ability was not inhibited even at 10 μM. On the other hand, the effect on murine leukemia was found to be a remarkable effect at up to 5 μM as shown in Table 6. Therefore, at such a concentration that such medicament can exhibit an effect on murine leukemia, the influence on normal murine bone marrow cells is determined to be small. Particularly in Example 21, it is predicted that a wide margin of safety can be ensured, and hence the potential of clinical application in the future is considered to be expanded.

The invention claimed is:

1. A compound represented by the following formula (I) or a pharmaceutically acceptable salt thereof:

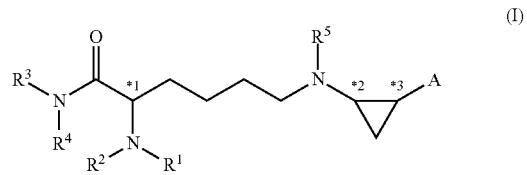

where:

R$^1$ and R$^2$ are identical to or different from each other, and each represent a hydrogen atom, an alkyl group that may have a substituent, a cycloalkyl group that may have a substituent, an alkylcarbonyl group that may have a substituent, a cycloalkylcarbonyl group that may have a substituent, an arylcarbonyl group that may have a substituent, a heteroarylcarbonyl group that may have a substituent, an aralkylcarbonyl group that may have a substituent, an alkyloxycarbonyl group that may have a substituent, a cycloalkyloxycarbonyl group that may have a substituent, an aryloxycarbonyl group that may have a substituent, or a heteroaryloxycarbonyl group that may have a substituent;

R$^3$ and R$^4$ are identical to or different from each other, and each represent a hydrogen atom, an alkyl group that may have a substituent, a cycloalkyl group that may have a substituent, an aryl group that may have a substituent, a heteroaryl group that may have a substituent, or an aralkyl group that may have a substituent, or R$^3$ and R$^4$ may form a nitrogen-containing heterocycle together with a nitrogen atom to which R$^3$ and R$^4$ are bonded, provided that R$^3$ and R$^4$ do not simultaneously represent a hydrogen atom;

R$^5$ represents a hydrogen atom, an alkyl group that may have a substituent, a cycloalkyl group that may have a substituent, an aryl group that may have a substituent, a heteroaryl group that may have a substituent, or an aralkyl group that may have a substituent;

A represents an aryl group that may have a substituent or a heteroaryl group that may have a substituent; and

*1 to *3 each represent asymmetric carbon.

2. The compound or a pharmaceutically acceptable salt thereof according to claim 1, wherein the compound is represented by the following formula (II):

(II)

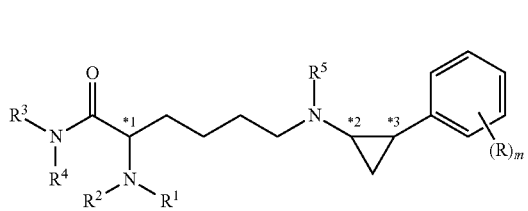

where:
- R¹ and R² are identical to or different from each other, and each represent a hydrogen atom, an alkyl group that may have a substituent, a cycloalkyl group that may have a substituent, an alkylcarbonyl group that may have a substituent, a cycloalkylcarbonyl group that may have a substituent, an arylcarbonyl group that may have a substituent, a heteroarylcarbonyl group that may have a substituent, an aralkylcarbonyl group that may have a substituent, an alkyloxycarbonyl group that may have a substituent, a cycloalkyloxycarbonyl group that may have a substituent, an aryloxycarbonyl group that may have a substituent, or a heteroaryloxycarbonyl group that may have a substituent;
- R³ and R⁴ are identical to or different from each other, and each represent a hydrogen atom, an alkyl group that may have a substituent, a cycloalkyl group that may have a substituent, an aryl group that may have a substituent, a heteroaryl group that may have a substituent, or an aralkyl group that may have a substituent, or R³ and R⁴ may form a nitrogen-containing heterocycle together with a nitrogen atom to which R³ and R⁴ are bonded, provided that R³ and R⁴ do not simultaneously represent a hydrogen atom;
- R⁵ represents a hydrogen atom, an alkyl group that may have a substituent, a cycloalkyl group that may have a substituent, an aryl group that may have a substituent, a heteroaryl group that may have a substituent, or an aralkyl group that may have a substituent;
- R represents a hydrogen atom or a substituent;
- m represents an integer of from 0 to 5; and
- *1 to *3 each represent asymmetric carbon.

3. The compound or a pharmaceutically acceptable salt thereof according to claim 1, wherein the compound is represented by any one of the following formulae (III) to (VI):

(III)

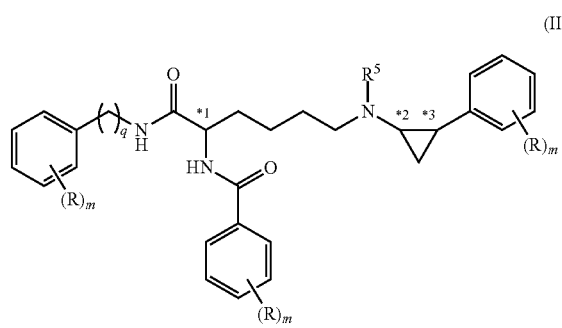

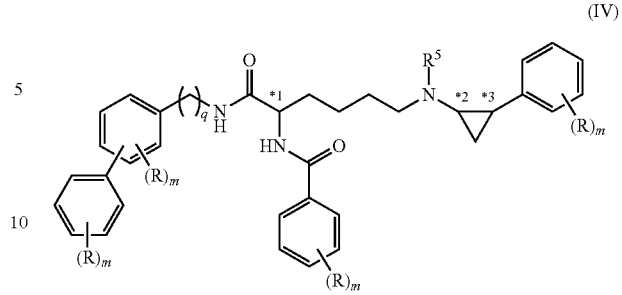

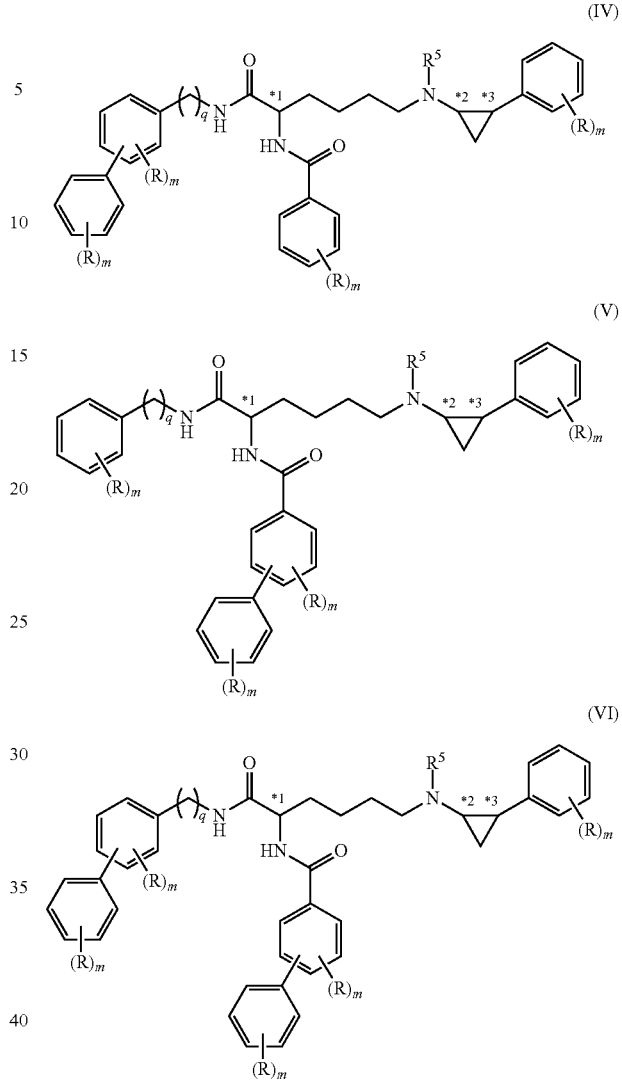

where:
- R⁵ represents a hydrogen atom, an alkyl group that may have a substituent, a cycloalkyl group that may have a substituent, an aryl group that may have a substituent, a heteroaryl group that may have a substituent, or an aralkyl group that may have a substituent;
- R's each represent a hydrogen atom or a substituent;
- m's are identical to or different from each other, and each represent an integer of from 0 to 5;
- q represent an integer of from 0 to 5;
- R's are identical to or different from each other, and each represent a hydrogen atom or a substituent; and
- *1 to *3 each represent asymmetric carbon.

4. The compound or a pharmaceutically acceptable salt thereof according to claim 1, wherein the compound is any one of the following compounds:
- 2-(N-benzenecarbonyl)amino-6-(trans-2-phenylcyclopropan-1-amino)-N-benzylhexanamide;
- 2-(N-tert-butoxycarbonyl)amino-6-(trans-2-phenylcyclopropan-1-amino)-N-benzylhexanamide;
- 2-amino-6-(trans-2-phenylcyclopropan-1-amino)-N-benzylhexanamide;
- 2-[N-(4-methylbenzenecarbonyl)]amino-6-(trans-2-phenylcyclopropan-1-amino)-N-benzylhexanamide;

2-[N-(4-tert-butylbenzenecarbonyl)]amino-6-(trans-2-phenylcyclopropan-1-amino)-N-benzylhexanamide;

2-[N-(4-chlorobenzenecarbonyl)]amino-6-(trans-2-phenylcyclopropan-1-amino)-N-benzylhexanamide;

2-[N-(4-fluorobenzenecarbonyl)]amino-6-(trans-2-phenylcyclopropan-1-amino)-N-benzylhexanamide;

2-[N-(4-phenylbenzenecarbonyl)]amino-6-(trans-2-phenylcyclopropan-1-amino)-N-benzylhexanamide;

2-[N-(4-trifluoromethylbenzenecarbonyl)]amino-6-(trans-2-phenylcyclopropan-1-amino)-N-benzylhexanamide;

2-{3-[(2-amino)ethylcarbamoyl]benzenecarbonylamino}-6-(trans-2-phenylcyclopropan-1-amino)-N-benzylhexanamide;

2-[3-(piperazine-1-carbonyl)benzenecarbonylamino]-6-(trans-2-phenylcyclopropan-1-amino)-N-benzylhexanamide;

2-[N-(4-phenylbenzenecarbonyl)]amino-6-(trans-2-phenylcyclopropan-1-amino)-N-(4-methylbenzyl)hexanamide;

2-[N-(4-phenylbenzenecarbonyl)]amino-6-(trans-2-phenylcyclopropan-1-amino)-N-(4-fluorobenzyl)hexanamide;

2-[N-(4-phenylbenzenecarbonyl)]amino-6-(trans-2-phenylcyclopropan-1-amino)-N-(4-phenylbenzyl)hexanamide;

2-[N-(4-phenylbenzenecarbonyl)]amino-6-(trans-2-phenylcyclopropan-1-amino)-N-(4-tert-butylbenzyl)hexanamide;

2-[N-(4-phenylbenzenecarbonyl)]amino-6-(trans-2-phenylcyclopropan-1-amino)-N-(3-methylbenzyl)hexanamide;

2-[N-(4-phenylbenzenecarbonyl)]amino-6-(trans-2-phenylcyclopropan-1-amino)-N-(3-fluorobenzyl)hexanamide;

2-[N-(4-phenylbenzenecarbonyl)]amino-6-(trans-2-phenylcyclopropan-1-amino)-N-(3-phenylbenzyl)hexanamide;

2-[N-(4-phenylbenzenecarbonyl)]amino-6-(trans-2-phenylcyclopropan-1-amino)-N-(3-trifluoromethylbenzyl)hexanamide;

2-[N-(4-phenylbenzenecarbonyl)]amino-6-(trans-2-phenylcyclopropan-1-amino)-N-(4-chlorobenzyl)hexanamide; and 2-[N-(4-phenylbenzenecarbonyl)]amino-6-(trans-2-phenylcyclopropan-1-amino)-N-(3-chlorobenzyl)hexanamide.

5. A pharmaceutical composition, comprising the compound or the pharmaceutically acceptable salt thereof according to claim 1.

6. An anticancer agent, comprising as an active ingredient the compound or the pharmaceutically acceptable salt thereof according to claim 1.

7. An antiviral drug, comprising as an active ingredient the compound or the pharmaceutically acceptable salt thereof according to claim 1.

8. A therapeutic drug for hemoglobinopathy, comprising as an active ingredient the compound or the pharmaceutically acceptable salt thereof according to claim 1.

9. A lysine-specific demethylase 1 (LSD1) inhibitor, comprising as an active ingredient the compound or the pharmaceutically acceptable salt thereof according to claim 1.

* * * * *